US007226577B2

(12) United States Patent
Cappelletti et al.

(10) Patent No.: US 7,226,577 B2
(45) Date of Patent: Jun. 5, 2007

(54) GASTRIN RELEASING PEPTIDE COMPOUNDS

(75) Inventors: Enrico Cappelletti, Sergno (IT); Luciano Lattuada, Bussero (IT); Karen E. Linder, Kingston, NJ (US); Edmund R. Marinelli, Lawrenceville, NJ (US); Palaniappa Nanjappan, Princeton, NJ (US); Natarajan Raju, Kendall Park, NJ (US); Rolf E. Swenson, Princeton, NJ (US); Michael Tweedle, Princeton, NJ (US)

(73) Assignee: Bracco Imaging, S. p. A., Milan (IT)

( * ) Notice: Subject to any disclaimer, the term of this patent is extended or adjusted under 35 U.S.C. 154(b) by 362 days.

(21) Appl. No.: 10/341,577

(22) Filed: Jan. 13, 2003

(65) Prior Publication Data

US 2004/0136906 A1 Jul. 15, 2004

(51) Int. Cl.
*A61K 49/00* (2006.01)
(52) U.S. Cl. .................... 424/9.1; 424/1.11; 424/1.65; 424/1.69; 514/2
(58) Field of Classification Search .............. 424/1.11, 424/1.65, 1.69, 9.1, 9.2, 9.3, 9.4, 9.5, 9.6, 424/9.7, 9.8; 514/2, 9; 530/300, 327; 534/7, 534/10–16
See application file for complete search history.

(56) References Cited

U.S. PATENT DOCUMENTS

| 4,885,363 | A | 12/1989 | Tweedle |
| 4,988,496 | A | 1/1991 | Srinivasan et al. |
| 5,068,222 | A | 11/1991 | Camble et al. |
| 5,217,955 | A | 6/1993 | Bogden et al. |
| 5,219,556 | A | 6/1993 | Wolfangel |
| 5,244,883 | A | 9/1993 | Cai et al. |
| 5,369,094 | A | 11/1994 | Schally et al. |
| 5,393,512 | A | 2/1995 | Vanderheyden et al. |
| 5,410,018 | A | 4/1995 | Spindel et al. |
| 5,428,018 | A | 6/1995 | Edwards et al. |
| 5,428,019 | A | 6/1995 | Edwards et al. |
| 5,534,497 | A | 7/1996 | Verbruggen |
| 5,620,955 | A | 4/1997 | Knight et al. |
| 5,620,959 | A | 4/1997 | Leban et al. |
| 5,649,537 | A | 7/1997 | Anelli et al. |
| 5,686,410 | A | 11/1997 | Albert et al. |
| 5,834,433 | A | 11/1998 | Krstenansky |
| 5,965,695 | A | 10/1999 | Simon et al. |
| 6,075,121 | A | 6/2000 | Simon et al. |
| 6,200,546 | B1 | 3/2001 | Hoffman et al. |
| 6,461,588 | B1 | 10/2002 | Anelli et al. |
| 6,803,030 | B2* | 10/2004 | De Haen et al. ......... 424/9.323 |
| 2002/0054855 | A1 | 5/2002 | Hoffman et al. |
| 2003/0224998 | A1 | 12/2003 | Reubi et al. |
| 2004/0253225 | A1* | 12/2004 | Cappelleti et al. ....... 424/94.63 |

FOREIGN PATENT DOCUMENTS

| WO | WO91/01144 | 2/1991 |
| WO | WO96/03427 | 2/1996 |

OTHER PUBLICATIONS

Giblin et al. (1998), Proc. Natl. Aca. Sci., USA, vol. 95, pp. 12814-12818.
Walsh et al., Western Journal of Medicine, vol. 155, pp. 152-163, 1991.
Heppeler et al., Receptor Targeting for Tumor Localization and Therapy with Radiopeptides. Current Medicinal Chemistry 2000, 7:971-994.
Sethi et al., Growth of small cell lung cancer cells: stimulation by multiple neuropeptides and inhibition by broad spectrum antagonists in vitro and in vivo, Cancer Res. May 1, 1992;52(9 Suppl):2737s-2742s.
Halmos, T., Wittliff, J.L., and Schally, A.V., Characterization of bombesin/gastrin releasing peptide receptors on human breast cancer and their Relationship to steroid receptor expression, Cancer Research 55:280-287, 1995.
Kelly, K., Kane, M.A., and Bunn, P.A., "Growth factors in lung cancer: Possible etiologic role and clinical target", Medical and Pediatric Oncology 19:449-458, 1991.
Reile, H., Armatis, P.E., and Schally, A.V., Characterization of high-affinity receptors for bombesin/gastrin releasing peptide on the human prostate cancer cell lines PC-3 and DU-145: internalization of receptor bound 125I-(Tyr4) bombesin by tumor cells, Prostate, Jul. 1994;25(1):29-38.
Schutte, J., and Seeber, S., "Bombesin antagonists: Experimental and clinical results", Recent Results in Cancer Research 129:115-129, 1993.
Walsh, J.H., Karnes, W.E., Cuttitta, F., and Walker, A., "Autocrine growth factors and solid tumor malignancy", Western Journal of Medicine 155: 152-163, 1991.
Leban, et al., Potent gastrin-releasing peptide (GRP) antagonsits derived from GRP (19-27) with a C-terminal DPro psi [CH2NH]Phe-NH2 and N-terminal aromatic residues, J Med Chem. Feb. 18, 1994;37(4):439-45.
Li, et al.; In-Vivo and In-Vitro Characterization of a Rh-105-Tetrathiamacrocycle Conjugate of a Bombesin Analogue, Proceedings of the 43rd Annual Meeting, vol. 37, No. 5, May 1996 Supplement, p. 61.
Zhu, et al.; Binding, internalization, and processing of bombesin by rat pancreatic acini, Bombesin Binding and Internalization, 1991, pp. G57-G64.

(Continued)

*Primary Examiner*—Dameron L. Jones
(74) *Attorney, Agent, or Firm*—Kramer Levin Naftali & Frankel LLP

(57) ABSTRACT

New and improved compounds for use in radiodiagnostic imaging or radiotherapy having the formula M-N-O-P-G, wherein M is the metal chelator (in the form complexed with a metal radionuclide or not), N-O-P is the linker, and G is the GRP receptor targeting peptide. Methods for imaging a patient and/or providing radiotherapy to a patient using the compounds of the invention are also provided. A method for preparing a diagnostic imaging agent from the compound is further provided. A method for preparing a radiotherapeutic agent is further provided.

24 Claims, 41 Drawing Sheets

OTHER PUBLICATIONS

Moody, et al.; BW1023U90: A new GRP Receptor Antagonist for Small-Cell Lung Cancer Cells, Peptides vol. 17, No. 8, pp. 1337-1343, 1996.

Moody, et al.; A GRP Receptor Antagonist Which Inhibits Small-Cell Lung Cancer Growth; Life Sciences, vol. 56, No. 7, pp. 521-529, 1995.

Seifert, et al.; No Carrier Added Preparations of '3+1' Mixed-ligand 99mTc Complexes, Appl. Radiat. Isot. vol. 49, Nos. 1-2, pp. 5-11, 1998.

Smith, et al.; In Vivo and In Vitro Characterization of Novel Water-Soluble Dithio-Bisphosphine 99mTc Complexes, Nuclear Medicine & Biology, vol. 24, pp. 685-691, 1977.

Coy et al, "Short Chain Pseudopeptide bombesin receptor antagonists with enhanced binding affinities for pancreatic Acinar and swiss 3T3 cells display strong Antimitotic activity" J. Biol. Chem., vol. 264, No. 25, pp. 14691-14697, 1989.

Thomas et al., Antitumoral Activity of Bombesin Analogues on Small Cell Lung Cancer Xenografts: Relationship with Bombesin Receptor Expression, Cancer Res. Sep. 15, 1992;52(18):4872-7.

Radulovic et al., Inhibitory effects of antagonists of bombesin/gastrin releasing peptide (GRP) and somatostatin analog (RC-160) on growth of HT-29 human colon cancers in nude mice, Acta Oncol. 1994;33(6):693-701

Qin, et al., Inhibitory effect of bombesin receptor antagonist RC-3095 on the growth of human pancreatic cancer cells in vivo and in vitro, Cancer Res. Feb. 15, 1994;54(4):1035-41.

Qin, et al., Antagonists of bombesin/gastrin-releasing peptide inhibit growth of SW-1990 human pancreatic adenocarcinoma and production of cyclic AMP, Int J Cancer. Oct. 9, 1995;63(2):257-62.

Cai et al., Potent Bombesin antagonists with C-Terminal Leu-(CH2-N)-Tac-NH2 or its Derivatives, (1994) Proc. Natl. Acad. Sci., 91:12664-12668.

Radulovic, et al., Biological effects and receptor binding affinities of new pseudononapeptide bombesin/GRP receptor antagonists with N-terminal D-Trp or D-Tpi, Int J Pept Protein Res. Dec. 1991;38(6):593-600.

Staley, et al., [Des-Met14]bombesin analogues function as small cell lung cancer bombesin receptor antagonists, Peptides. Jan.-Feb. 1991;12(1):145-9.

Wang et al., Desmethionine alkylamide bombesin analogues: a new class of bombesin receptor antagonists with potent antisecretory activity in pancreatic acini and antimitotic activity in Swiss 3T3 cells, Biochemistry. Jan. 23, 1990;29(3):616-22.

Wang, Knezetic, Schally, Pour, Adrian; Bombesin May Stimulate Proliferation of Human Pancreatic Cancer Cells Through An Autocrine Pathway, Int. J. Cancer: 68, 528-534 (1996).

Yano, Pinski, Groot, Schally, Stimulation by bombesin and inhibition by bombesin/gastrin-releasing peptide antagonist RC-3095 of growth of human breast cancer cell lines, Cancer Res. Aug. 15, 1992;52(16):4545-7.

Kane, Auguayo, Portanova, Ross, Holley, Kelly, Miller, Isolation of the bombesin/gastrin-releasing peptide receptor from human small cell lung carcinoma NCI-H345 cells, J Biol Chem. May 25, 1991;266(15):9486-93.

Schuller, Receptor-mediated mitogenic signals and lung cancer, Caner Cells. Dec. 1991;3(12):496-503.

Halmos et al., Characterization of bombesin/gastrin-releasing peptide receptors in human breast cancer and their relationship to steroid receptor expression, Cancer Res. Jan. 15, 1995;55(2):280-7.

Hajri et al., Gastrin-releasing peptide: in vivo and in vitro growth effects on an acinar pancreatic carcinoma, Cancer Res. Jul. 1, 1992;52(13):3726-32.

Fritzberg, et al., Radiolabeling of Antibodies for Targeted Diagnostics, Handbook of Targeted Delivery of Imaging Agents (ed) V.P. Torchilin, CRC Press, Boca Raton, Florida, Chapter 6, pp. 83-101, 1995.

Radulovic, et al., The Binding of Bombesin and Somatostatin and Their Analogs to Human Colon Cancers, 1992.

John E. Taylor, Identification and Characterization Somatostatin (SRIF), Gastrin Releasing Peptide (GRP), and Neuromedin B (NMB) Receptors on Established Tumors and Tumor Cell Lines, 1993.

Benya, et al., Gastrin-releasing peptide receptor-induced internalization, down-regulation, desensitization, and growth: possible role for cyclic AMP, Mol Pharmacol. Aug. 1994;46(2):235-45.

Yano, et al., Inhibitory effect of bombesin/gastrin-releasing peptide antagonist RC-3095 and luteinizing hormone-releasing hormone antagonist SB-75 on the growth of MCF-7 MIII human breast cancer xenografts in athymic nude mice, Cancer. Feb. 15, 1994;73(4):1229-38.

Kull, Jr., et al., Conveyance of partial agonism/antagonism to bombesin/gastrin-releasing peptide analogues on Swiss 3T3 cells by a carboxyl-terminal leucine insertion, J Biol Chem. Oct. 15, 1992;267(29):21132-8

Heinz-Erian, et al., [D-Phe12]bombesin analogues: a new class of bombesin receptor antagonists, Am J Physiol. Mar. 1987;252(3 Pt 1):G439-42.

Halmos, et al., Characterization of bombesin/gastrin-releasing peptide receptors in membranes of MKN45 human gastric cancer, Cancer Lett. Sep. 30, 1994;85(1):111-8.

Coy, et al., Short-chain pseudopeptide bombesin receptor antagonists with enhanced binding affinities for pancreatic acinar and Swiss 3T3 cells display strong antimitotic activity, J Biol Chem. Sep. 5, 1989;264(25):14691-7.

Woll, et al., [D-Arg1,D-Phe5,D-Trp7,9,Leu11]substance P, a potent bombesin antagonsit in murine Swiss 3T3 cells, inhibits the growth of human small cell lung cancer cells in vitro, Proc Natl Acad Sci U S A. Mar. 1988;85(6):1859-63.

Wang, et al., des-Met carboxyl-terminally modified analogues of bombesin function as potent bombesin receptor antagonists, partial agonists, or agonists, J Biol Chem. Sep. 15, 1990;265(26):15695-703.

Von Schrenck, et al., "Potent Bombesin Receptor Antagonists distinguish Receptor Subtypes", Amer. J. Physiol., vol. 259, pp. G468-G473, 1990.

Singh, et al., A novel bombesin receptor antagonist (2258U89), potently inhibits bombesin evoked release of gastrointestinal hormones from rats and dogs, in vitro and in vivo, Regul Pept. Jul. 2, 1992;40(1):75-86.

Leban, et al., Development of Potent Bombesin/Gastrin-Releasing Peptide antagonists Having a D-Pro-(CH2NH)-Phe-NH2 C Terminus, Proc Natl Acad Sci U S A. Mar. 1, 1993;90(5):1922-6.

Mahmoud, et al., "[Psi 13, 14] Bombesin Analogues Inhibit Growth of Small Cell Lung Cancer in Vitro and in Vivo", Cancer Res. Apr. 1, 1991;51(7):1798-802.

Troutner, David E., Chemical and Physical Properties of Radionuclides, Nucl. Med. Biol. vol. 14, No. 3, pp. 171-176, 1987.

Vallabhajosula, et al., Preclinical evaluation of technetium-99m-labeled somatostatin receptor-binding peptides, J Nucl Med. Jun. 1996;37(6):1016-22.

Gali, et al., Synthesis, characterization, and labeling with 99mTc/188Re of peptide conjugates containing a dithia-bisphosphine chelating agent, Bioconjugate Chem. May-Jun. 2001;12(3):354-63.

Bijsterbosch, MK; Selective Drug Delivery by Means of Receptor-Mediated Endocytosis, The Quarterly Journal of Nuclear Medicine, vol. 39, No. 1, pp. 4-19, Mar. 1995.

Parker, David; Tumor Targeting with Radiolabelled Macrocycle-Antibody Conjugates, Chemical Society Reviews, vol. 19, No. 3, Sep. 1990, pp. 271-291.

Wilbur, D. Scott; Radiohalogenation of Proteins: An Overview of Radionuclides, Labeling Methods, and Reagents for Conjugate Labeling, Bioconjugate Chem. Nov.-Dec. 1992;3(6)433-70.

Smythe, et al.; The Mechanism of Receptor-Mediated Endocytosis; Eur. J. Biochem. 202, pp. 689-699, 1991.

Wong, et al.; Rhenium(V), and Technetium(V) Oxo Complexes of an N2N's Peptide Chelator: Evidence of Inter-conversion between the Syn and Anti Conformations; Inorg. Chem., 1997, 36, pp. 5799-5808.

Schumbiger, et al.; Vehicles, Chelators, and Radionuclides: Choosing the "Building Blocks" of an Effective Therapeutic Radioimmunoconjugate; Bioconjugate Chemistry, vol. 7, No. 2, pp. 165-179, Mar./Apr. 1996.

Li, et al.; Comparisons of Rh(III) Chloride Complexation with [14]aneNS, [14]aneN2S2 and [14]aneN4 Macrocycles in Aqueous Solution, Radiochemica Acta 75, pp. 83-95 (1996).

Lamberts, S.W.J., Reubi, J.C., Krenning, E.P.; Somatostatin and the Concept of Peptide Receptor Scintigraphy in Oncology, Seminars in Oncology, vol. 21, No. 5, Suppl. 13 (Oct. 1994), pp. 1-5.

Hermanson; Bioconjugate Techniques, Academic Press, Functional Targets, Chapter 1, pp. 3-136 (1996).

Hoffken, K.; Peptides in Oncology II, Somatostatin Analogues and Bombesin Antagonists (1993), Springer-Verlag, Berlin-Heidelberg, pp. 87-112.

Krenning, et al.; Essentials of Peptide Receptor Scintigraphy with Emphasis on the Somatostatin Analog Octreotide, Seminars in Oncology, vol. 21, No. 5, Suppl. 13 (Oct. 1994), pp. 6-14.

Eckelman, William C., Gibson, Raymond E., (1993) The Design of Site-Directed Radiopharmaceuticals for use in Drug Discovery, Nuclear Imaging in Drug Discovery, Development, and Approval (eds) H.D. Burns et al., Birkauser Publ. Inc., Boston, Ma.

Fischman, et al.; A ticket to ride: peptide radiopharmaceuticals, J Nucl Med. Dec. 1993;34(12):2253-63.

Duncan et al.; Indium-111-Diethylenetriaminepentaacetic Acid-Octreoide is Delivered in Vivo to Pancreatic, Tumor Cell, Renal, and Hepatocyte Lysosomes, Cancer Res. Feb. 15, 1997;57(4):659-71.

Eckelman, William c.; Radiolabeling with technetium-99m to study high-capacity and lo-capacity biochemical systems, Eur J Nucl Med. Mar. 1995;22(3):249-63.

Davis, et al.; Metabolic Stability and Tumor Inhibition of Bombesin/GRP Receptor Antagonists, Peptides. Mar.-Apr. 1992;13(2):401-7.

De Jong et al.; Yttrium-90 and indium-111 labeling, receptor binding and biodistribution of [DOTA0, d-Phel,Tyr3]octreotide, a promising somatostatin analogue for radionuclide therapy, Eur J Nucl Med. Apr. 1997;24(4):368-71.

Fritzberg et al.; Targeted proteins for diagnostic imaging: does chemistry make a difference?; J Nucl Med. Mar. 1992;33(3):394-7.

Cai et al.; Pseudononapeptide Bombesin Antagonists Containing C-Terminal Trp or Tpi, Peptides, Mar.-Apr. 1992;13(2):267-71.

Coy et al.; Probing peptide backbone function in bombesin. A reduced peptide bond analogue with potent and specific receptor antagonist activity, J Biol Chem. Apr. 15, 1988;263(11):5056-60.

Donald J. Buchsbaum; Cancer Therapy with Radiolabelled Antibodies; Pharmacokinetics of Antibodies and their Radiolabels; Experimental Radioimmunotherapy and Methods to Increase Therapeutic Efficacy; CRC Press, Boca Raton, Chapter 10, pp. 115-140, 1995).

Zhu et al.; Binding, internalization, and processing of bombesin by rat pancreatic acini, Am J Physiol. Jul. 1991;261(1 Pt 1):G57-64.

Mulshine et al.; Autocrine growth factors as therapeutic targets in lung cancer, Chest. Jul. 1989;96(1 Suppl):31S-34S. Review.

Hoffken, K.; Peptides in Oncology II, Somatostatin Analogues: Mechanisms of Action, (1994), Springer-Verlag, Berlin-Heidelberg, pp. 1-136.

Gali, et al.; In Vitro and in Vivo Evaluation of 111In_Labeled DOTA_8_Aoc_BBN[7_14]NH2 Conjugate for Specific Targeting of Tumors Expressing Gastrin Releasing Peptide (GRP) Receptors, 47th Annual Meeting—Society of Nuclear Medicine, St. Louis, MO, J. Nucl. Med., 41(5), 119P, #471, 2000.

Gali, et al.; Influence of the Radiometal on the In Vivo Pharmacokinetic Properties of a Radiometal-labeled DOTA-Conjugated Peptide, 222nd American Chemical Society National Meeting, Chicago, Il, Aug. 2001 (Accepted).

Hoffman, et al.; Development and Characterization of a Receptor-Avid 111In-Labeled Peptide for Site Specific Targeting of Colon Cancer, 92nd Annual Meeting of the American Association for Cancer Research, New Orleans, LA, Proceedings of the American Association for Cancer Research, vol. 42, 139, #746, Mar. 2001.

Hoffman, et al.; Rh-105 Bombesin Analogs: Selective In Vivo Targeting of Prostate Cancer with a therapeutic Radionuclide, 45th Annual Meeting-Society of Nuclear Medicine, Jun. 1998;J.Nucl. Med., 39(5), #982, 222P.

Hoffman, et al.; Uptake in retention of a Rh-105 Labeled Bombesin Analogue in GRP Receptor Expressing Neoplasms: An In-Vitro Study, 44th Annual Meeting—Society of Nuclear Medicine, Jun. 1997;J.Nucl. Med., 38(5), #808, 188P, 1997.

Hoffman, et al.; Synthesis and Characterization of Rh-105 Labeled Bombesin Analogues: Enhancement of GRP Receptor Binding Affinity Utilizing Aliphatic Carbon Chain Linkers, 12th International Symposium on Radiopharmaceutical Chemistry, Jun. 1997.

Hoffman, et al.; Specific Uptake and retention of Rh-105 Labeled Bombesin Analogues in GRP-Receptor Expressing Cells, European Society of Nuclear Medicine, Aug. 1997; Eur. J. Nucl. Med., 24(8), 901, 1997.

Hoffman et al.; Radiometallated receptor-avid peptide conjugates for specific in vivo targeting of cancer cells, Nucl Med Biol. Jul. 2001;28(5):527-39.

Hoffman et al.; Targeting Small Cell Lung Cancer Using Iodinated Peptide Analogs, 11th International Symposium on Radiopharmaceutical Chemistry, Aug. 1995; J. Label. Comp'd Radiopharm., 37:321-323, 1995.

Hoffman et al.; Iodinated Bombesin Analogs: Effect of N-Terminal Chain Iodine Attachment on BBN/GRP Receptor Binding, 43rd Annual Meeting—Society of Nuclear Medicine, May 1996; J. Nucl. Med., 37(5), p. 185P, #850, 1996.

Hoffman et al.; Accumulation and Retention of 99mTc-RP591 by GRP Receptor Expressing Tumors in SCID Mice, Congress of the European Association of Nuclear Medicine, Barcelona, Spain, Eur. J. Nucl. Med., 26(9), 1157, #PS-416, Sep. 1999.

Hoffman et al.; Accumulation and Retention of 99mTc-RP527 by GRP Receptor Expressing Tumors in SCID Mice, 46th Annual Meting—Society of Nuclear Medicine, Jun. 9, 1999, Los Angeles, CA, J. Nucl. Med., 40(5), 104P, #419, 1999.

Hoffman et al.; 111In/90Y Radiolabelled Peptides for Targeting Prostate Cancer; A Matched Pair Gastrin Releasing Peptide (GRP) Receptor Localizing Radiopharmaceutical, 48th Annual Meting—Society of Nuclear Medicine, #1149, Toronto, Ontario, Canada, Jun. 2001. (Accepted).

Hoffman et al.; Vitro and in Vivo Evaluation of 111In/90Y Radiolabelled Peptides for Specific Targeting of Tumors Expressing Gastrin Releasing Peptide (GRP) Receptors, 92nd Annual Meting of the American Association for Cancer Research, New Orleans, LA. Proceedings of the American Association for Cancer Research, vol. 42, 773, #4148, Mar. 2001.

Hoffman et al.; Development of a Diagnostic Radiopharmaceutical for Visualization of Primary and Metastic Breast Cancer, 48th Annual Meting—Society of Nuclear Medicine, #1149, Toronto, Ontario, Canada, Jun. 2001, J. Nucl. Med., 45(5):245P, #1067.

Hoffman et al.; Targeting Gastrin Releasing Peptide (GRP-R) Expression in Prostate and Pancreatic Cancer Using Radiolabelled GRP Agonist Peptide Vectors, American Association for Cancer Research Annual Meeting, San Francisco, CA, Proceedings of the American Association for Cancer Research, vol. 41, 529, #3374, Apr. 2000.

Hoffman T.J., Smith, C.J., Simpson, S.D., Siekman, G., Higginbotham, C., Jiminez, H., Eshima, D., Thornback, J.R. and Volkert, W.A.; Optimizing Pharmacokinetics of Tc-99m-GRP Receptor Targeting Peptides Using Multi-Amino Acid Linking groups, 47th Annual Meting—Society of Nuclear Medicine, St. Louis, MO, J. Nucl. Med., 41(5), 228), #1013, 2000.

Jurrison, S., Cutler, C., Hu, F., Hoffman, T.J., Volkert, W.A.; DOTA Bombesin Complexes with Sm-153 and NCA PM-149, The International Chemical Congress of Pacific Basin Societies, Pacifichem 2000, Honolulu, HI, Dec. 2000.

Kara, S.R., Schibli, R., Gali, H., Katti, K.V., Hoffman, T.J., Higginbotham, C., Siekman, G., Volkert, W.A.; 99mTc-labeling and in vivo studies of a bombesin analogue with a novel water-soluble dithiadiphosphine-based bifunctional chelating agent, Bioconjug Chem. Mar.-Apr. 1999;10(2):254-60.

Katti, K.V., Gali, H., Schibli, R., Hoffman. T.J., and Volkert, W.A.; 99mTc/Re Coordination Chemistry and Biomolecule Conjugation Strategy of a Novel Water Soluble Phosphine-Based Bifunctional Chelating Agent, In Technetium, Rhenium and Other Metals in Chemistry and Nuclear Medicine (5), Ed by M. Nicolini and U. Mazzi, Servizi Grafici Editoriali, Padova, pp. 93-100, 1999.

Kothari, K.K. Katti, K.V., Prabhu, K.R., Gali, H., Pillarsetty, N.K., Hoffman, T.J., Owen, N.K., and Volkert, W.A.; Development of a Diamido-Diphosphine (N2P2)-BFCA for Labeling Cancer Seeking Peptides via the 99mTc(1)(CO)3(H2O)3 Intermediate, 47th Annual Meeting—Society of Nuclear Medicine, St. Louis, MO, J. Nucl. Med., 41(5), 244P, #1079, 2000.

Li, et al.; Development of an in vitro model for assessing the in vivo stability of lanthanide chelates, Nucl Med Biol. Feb. 2001;28(2):145-54.

Qin, et al.; Bombesin antagonists inhibit in vitro and in vivo growth of human gastric cancer and binding of bombesin to its receptors, J Cancer Res Clin Oncol., 1994; 120(9):519-28.

Schibli, R., Karra, S.R., Gali, H., Katti, K.V., Higginbotham, C., Smith, C.J., Hoffman, T.J., and Volkert, W.A.; Conjugation of Small Biomolecules and Peptides with Water-Soluble Dithio-Bis-Hydroxymethylphosphine Ligands, Center Radiological Research, University of Missouri, Columbia, MO, USA. Book of Abstracts, 215th ACS National Meeting, Dallas, Mar. 29-Apr. 2, 1998, NUCL-062.

Schibli, R., Karra, S.R., Katti, K.V., Gali, H., Higginbotham, C., Siekman, G., Hoffman, T.J., and Volkert, W.A.; A Tc-99m-Dithia-Di(Bis-Hydroxy-methylene) Phosphine Conjugate of Bombesin: In Vitro and In Vivo Studies, 45th Annual Meeting—Society of Nuclear Medicine, May 1998; J. Nucl. Med., 39(5), 225P, #997.

Smith, C.J., Hoffman, T.J., Gali, H., Hayes, D.L., Owen, N.K., Siekman, G.L. and Volkert, W.A.; Radiochemical investigations of 177Lu-DOTA-8-Aoc-BBN[7-14]NH2: A New Gastrin Releasing Peptide Receptor (GRPr) Targeting Radiopharmaceutical, J. Labeled Compounds and Radiopharmaceutical, J. Labeled Cpd. Radipharm., 44 (51):5706-5708, 2001.

Volkert, W.A.; Rh-105 Bombesin Analogs: Selective In Vivo Targeting of Prostate Cancer with a Therapeutic Radionuclide, 45th Annual Meeting—Society of Nuclear Medicine, Jun. 1998; J. Nucl. Med., 39(5):222P, #59, 1998.

Volkert, W.A., and Hoffman, T.J., Design and Development of Receptor-avid Peptide Conjugates for In Vivo Targeting of Cancer, Part of the SPIE Conference of Molecular Imaging: Reporters-Dyes, Markers and Instrumentation, SPIE vol. 3600:86-98, Jan. 1999.

Volkert, W.A., Gali, H., Hoffman, T.J., Owen, N.K., Sieman, G.L., and Smith, C.J.; In-111/90Y Labeled GRP Analogs: A Structure-Activity Relationship, The International Chemical Congress of Pacific Basin Societies, Pacifichem 2000, Honolulu, HI, Dec. 2000.

Foster, B., and Volkert, W.A.; In-111/90Y Radiolabelled Peptides for targeting Prostate Cancer; A Matched Pair Gastrin releasing Peptide (GRP) Receptor Localizing Radiopharmaceutical, 48th Annual Meeting—Society of Nuclear Medicine, Toronto, Ontario, Canada, Jun. 2001. (Accepted).

* cited by examiner

L62

1. Morpholine (50% in DMA)
2. Fmoc-4-aminobenzoic acid, HATU, DMA
3. Morpholine (50% in DMA)
4. Fmoc-Gly-OH, DIC, HOBt, DMA
5. Morpholine (50% in DMA)
6. DOTA tri-t-butyl ester, DIC, HOBt, DIEA, DMA
7. Reagent B

L70

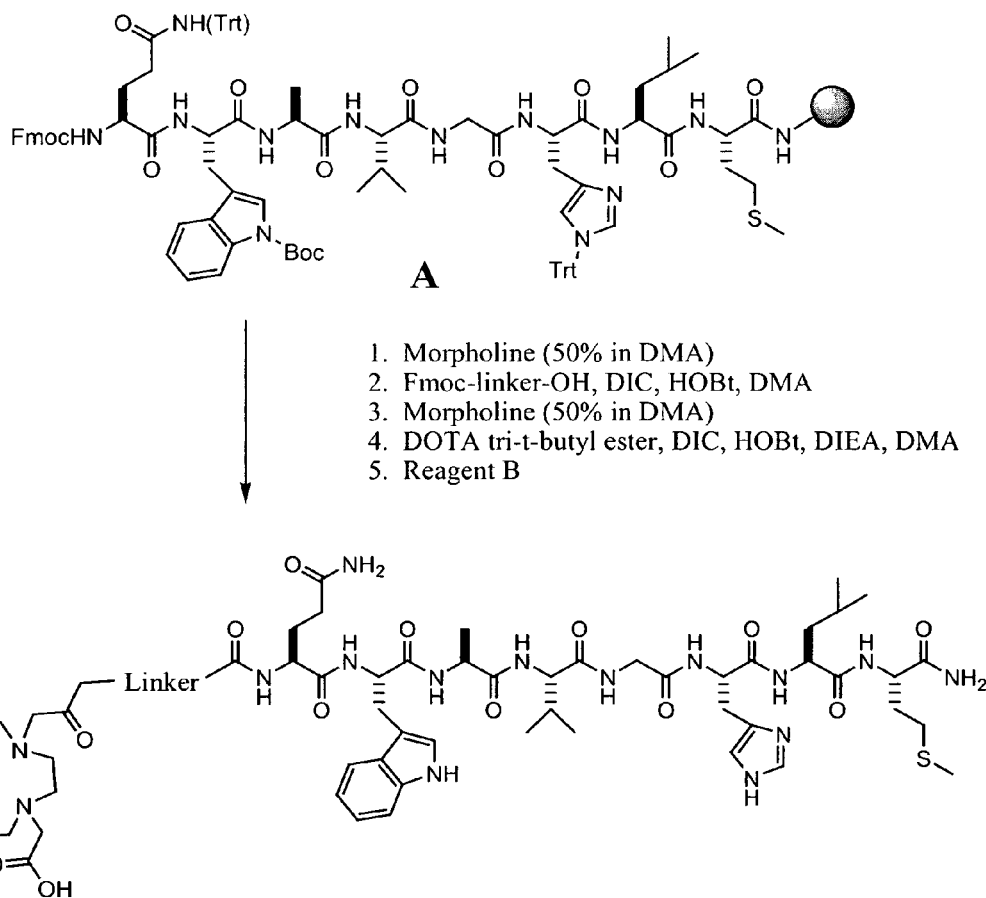
FIG. 2B
LINKERS:
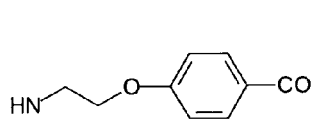 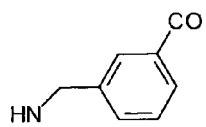 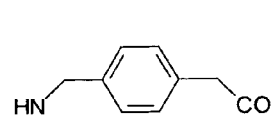
L73          L115          L116
FIG. 2C     FIG. 2D     FIG. 2E

L74

B

C

L67

L63

L64

2b

3a

3b

L63

L64

L71

L72

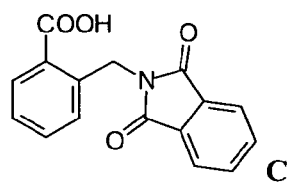
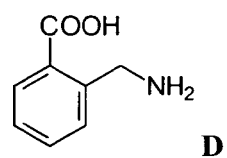
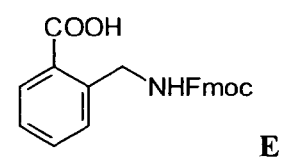
FIG. 6E          FIG. 6F          FIG. 6G
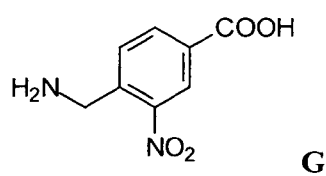
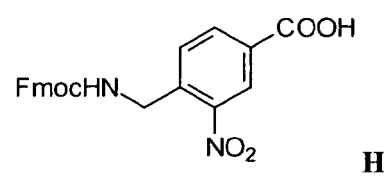
FIG. 6H          FIG. 6I

L75

L76

1. Morpholine (50% in DMA)
2. E, DIC, HOBt, DMA
3. Morpholine (50% in DMA)
4. DOTA tri-t-butyl ester, DIC, HOBt, DIEA, DMA
5. Reagent B

L124

B

C

E

L124

1. Morpholine (50% in DMA)
2. E, DIC, HOBt, DMA
3. Morpholine (50% in DMA)
4. DOTA tri-t-butyl ester, DIC, HOBt, DIEA, DMA
5. Reagent B

L125

L125

L66

L70

L114

L144

L69

L146

Chart 1

A

X = H, Tmob, Xan, Trt
U = →O or null
Y = Trt, Bum, Boc, Cbz
P = Fmoc, Boc, Aloc, H, Cbz

B

X' = H, t-Bu, Bz, 2-Cl-Trt, Me, Et
Y' = CHO, Boc, H, 9-PhF, CBz
Z = H, Xan, Tmob, Trt
P' = Fmoc, Boc, Aloc, H, Cbz

C1

P" = Fmoc, Boc, Aloc, H, Cbz

C2

P''' = Fmoc, Boc, Aloc, H, Cbz

D

X" = t-Bu, Me, Bz, H

SEQUENCE LISTING

<160> NUMBER OF SEQ ID NOS: 1

<210> SEQ ID NO 1
<211> LENGTH: 8
<212> TYPE: PRT
<213> ORGANISM: Artificial
<220> FEATURE:
<223> OTHER INFORMATION: Description of Artificial Sequence: This
      peptide is the receptor binding site of
      bombesin and is also known as BBN[7-14]

<400> SEQUENCE: 1

Gln Trp Ala Val Gly His Leu Met
1               5

GASTRIN RELEASING PEPTIDE COMPOUNDS

FIELD OF THE INVENTION

This invention relates to novel radionuclide-labeled gastrin releasing peptide (GRP) compounds which are useful as diagnostic imaging agents or radiotherapeutic agents. These GRP compounds include the use of novel linkers between a metal chelator and the targeting peptide, which provides for improved pharmacokinetics.

BACKGROUND OF THE INVENTION

The use of radiopharmaceuticals (e.g., diagnostic imaging agents, radiotherapeutic agents) to detect and treat cancer is well known. In more recent years, the discovery of site-directed radiopharmaceuticals for cancer detection and/or treatment has gained popularity and continues to grow as the medical profession better appreciates the specificity, efficacy and utility of such compounds.

These newer radiopharmaceutical agents typically consist of a targeting agent connected to a metal chelator, which can be chelated to (e.g., complexed with) a diagnostic metal radionuclide such as, for example, technetium or indium, or a therapeutic metal radionuclide such as, for example, lutetium, yttrium, or rhenium. The role of the metal chelator is to hold (i.e., chelate) the metal radionuclide as the radiopharmaceutical agent is delivered to the desired site. A metal chelator which does not bind strongly to the metal radionuclide would render the radiopharmaceutical agent ineffective for its desired use since the metal radionuclide would therefore not reach its desired site. Thus, further research and development led to the discovery of metal chelators, such as that reported in U.S. Pat. No. 5,662,885 to Pollak et. al., hereby incorporated by reference, which exhibited strong binding affinity for metal radionuclides and the ability to conjugate with the targeting agent. Subsequently, the concept of using a "spacer" to create a physical separation between the metal chelator and the targeting agent was further introduced, for example in U.S. Pat. No. 5,976,495 to Pollak et. al., hereby incorporated by reference.

The role of the targeting agent, by virtue of its affinity for certain binding sites, is to direct the radiopharmaceutical agent containing the metal radionuclide to the desired site for detection or treatment. Typically, the targeting agent may include a protein, a peptide, or other macromolecule which exhibits a specific affinity for a given receptor. Other known targeting agents include monoclonal antibodies (MAbs), antibody fragments ($F_{ab}$'s and $(Fab)_2$'s), and receptor-avid peptides. Donald J. Buchsbaum, "Cancer Therapy with Radiolabeled Antibodies; Pharmacokinetics of Antibodies and Their Radiolabels; Experimental Radioimmunotherapy and Methods to Increase Therapeutic Efficacy," CRC Press, Boca Raton, Chapter 10, pp. 115–140, (1995); Fischman, et al. "A Ticket to Ride: Peptide Radiopharmaceuticals," The Journal of Nuclear Medicine, vol. 34, No. 12, (December 1993).

In recent years, it has been learned that some cancer cells contain gastrin releasing peptide (GRP) receptors (GRP-R) of which there are a number of subtypes. In particular, it has been shown that several types of cancer cells have over-expressed or uniquely expressed GRP receptors. For this reason, much research and study have been done on GRP and GRP analogues which bind to the GRP receptor family. One such analogue is bombesin (BBN), a 14 amino acid peptide (i.e., tetradecapeptide) isolated from frog skin which is an analogue of human GRP and which binds to GRP receptors with high specificity and with an affinity similar to GRP.

Bombesin and GRP analogues may take the form of agonists or antagonists. Binding of GRP or BBN agonists to the GRP receptor increases the rate of cell division of these cancer cells and such agonists are internalized by the cell, while binding of GRP or BBN antagonists generally does not result in either internalization by the cell or increased rates of cell division. Such antagonists are designed to competitively inhibit endogenous GRP binding to GRP receptors and reduce the rate of cancer cell proliferation. See, e.g., Hoffken, K.; Peptides in Oncology II, Somatostatin Analogues and Bombesin Antagonists (1993), pp. 87–112. For this reason, a great deal of work has been, and is being pursued to develop BBN or GRP analogues that are antagonists. E.g., Davis et al., Metabolic Stability and Tumor Inhibition of Bombesin/GRP Receptor Antagonists, Peptides, vol. 13, pp. 401–407, 1992.

In designing an effective radiopharmaceutical compound for use as a diagnostic or therapeutic agent for cancer, it is important that the drug have appropriate in vivo targeting and pharmacokinetic properties. For example, it is preferable that the radiolabeled peptide have high specific uptake by the cancer cells (e.g., via GRP receptors). In addition, it is also preferred that once the radionuclide localizes at a cancer site, it remains there for a desired amount of time to deliver a highly localized radiation dose to the site.

Moreover, developing radiolabeled peptides that are cleared efficiently from normal tissues is also an important factor for radiopharmaceutical agents. When biomolecules (e.g., MAb, $F_{ab}$ or peptides) labeled with metallic radionuclides (via a chelate conjugation), are administered to an animal such as a human, a large percentage of the metallic radionuclide (in some chemical form) can become "trapped" in either the kidney or liver parenchyma (i.e., is not excreted into the urine or bile). Duncan et al.; Indium-111-Diethyl-enetriaminepentaacetic Acid-Octreotide Is Delivered in Vivo to Pancreatic, Tumor Cell, Renal, and Hepatocyte Lysosomes, Cancer Research 57, pp. 659–671, (Feb. 15, 1997). For the smaller radiolabeled biomolecules (i.e., peptides or $F_{ab}$), the major route of clearance of activity is through the kidneys which can also retain high levels of the radioactive metal (i.e., normally >10–15% of the injected dose). Retention of metal radionuclides in the kidney or liver is clearly undesirable. Conversely, clearance of the radiopharmaceutical from the blood stream too quickly by the kidney is also undesirable if longer diagnostic imaging or high tumor uptake for radiotherapy is needed.

Subsequent work, such as that in U.S. Pat. No. 6,200,546 and 2002/0054855 to Hoffman, et. al, hereby incorporated by reference, has attempted to overcome this problem by forming a compound having the general formula X-Y-B wherein X is a group capable of complexing a metal, Y is a covalent bond on a spacer group and B is a bombesin agonist binding moiety. Such compounds were reported to have high binding affinities to GRP receptors, and the radioactivity was retained inside of the cells for extended time periods. In addition, in vivo studies in normal mice have shown that retention of the radioactive metal in the kidneys was lower than that known in the art, with the majority of the radioactivity excreted into the urine.

New and improved radiopharmaceutical compounds which have improved pharmacokinetics and improved kidney excretion (i.e., lower retention of the radioactive metal in the kidney) have now been found for diagnostic imaging and therapeutic uses. For diagnostic imaging, rapid renal excretion and low retained levels of radioactivity are critical for improved images. For radiotherapeutic use, slower blood clearance to allow for higher tumor uptake and better tumor targeting with low kidney retention are critical.

SUMMARY OF THE INVENTION

In an embodiment of the present invention, there is provided new and improved compounds for use in radiodiagnostic imaging or radiotherapy. The compounds include a chemical moiety capable of complexing a medically useful metal ion or radionuclide (metal chelator) attached to a GRP receptor targeting peptide by a linker or spacer group.

In general, compounds of the present invention may have the formula:

M-N-O-P-G wherein M is the metal chelator (in the form complexed with a metal radionuclide or not), N-O-P is the linker, and G is the GRP receptor targeting peptide.

The metal chelator M may be any of the metal chelators known in the art for complexing with a medically useful metal ion or radionuclide. Preferred chelators include DTPA, DOTA, DO3A, HP-DO3A, EDTA, TETA, EHPG, HBED, NOTA, DOTMA, TETMA, PDTA, TTHA, LICAM, MECAM, or peptide chelators, such as, for example, those discussed herein. The metal chelator may or may not be complexed with a metal radionuclide, and may include an optional spacer such as a single amino acid. Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au and $^{199}$Au. The choice of metal will be determined based on the desired therapeutic or diagnostic application. For example, for diagnostic purposes the preferred radionuclides include $^{64}$Cu, $^{67}$Ga, $^{68}$Ga, $^{99m}$Tc, and $^{111}$In, with $^{99m}$Tc, and $^{111}$In being particularly preferred. For therapeutic purposes, the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$Yb, $^{177}$Lu, $^{186/188}$Re, and $^{199}$Au, with $^{177}$Lu and $^{90}$Y being particularly preferred. A most preferred chelator used in compounds of the invention is 1-substituted 4,7,10-tricarboxymethyl 1,4,7,10 tetraazacyclododecane triacetic acid (DO3A).

In one embodiment, the linker N-O-P contains at least one non-alpha amino acid.

In another embodiment, the linker N-O-P contains at least one substituted bile acid.

In yet another embodiment, the linker N-O-P contains at least one non-alpha amino acid with a cyclic group.

The GRP receptor targeting peptide may be GRP, bombesin or any derivatives or analogues thereof. In a preferred embodiment, the GRP receptor targeting peptide is a GRP or bombesin analogue which acts as an agonist. In a particularly preferred embodiment, the GRP receptor targeting peptide is a bombesin agonist binding moiety disclosed in U.S. Pat. No. 6,200,546 and 2002/0054855, incorporated herein by reference.

There is also provided a novel method of imaging using the compounds of the present invention.

There is further provided a novel method for preparing a diagnostic imaging agent comprising the step of adding to an injectable imaging medium a substance containing the compounds of the present invention.

A novel method of radiotherapy using the compounds of the invention is also provided, as is a novel method for preparing a radiotherapeutic agent comprising the step of adding to an injectable therapeutic medium a substance comprising a compound of the invention.

BRIEF DESCRIPTION OF THE DRAWINGS

FIG. 2B is a general graphical representation of the sequential reaction for the synthesis of N-[4-[2-[[[4,7,10-Tris(carboxymethyl)-1,4,7,10-tetraazacyclododec-1-yl] acetyl]amino]ethoxy]benzoyl]-L-glutaminyl-L-tryptophyl-L-alanyl-L-valyl-glycyl-L-histidyl-L-leucyl-L-methioninamide (L73), N-[3-[[[[4,7,10-Tris (carboxymethyl)-1,4,7,10-tetraazacyclododec-1-yl]acetyl] amino]methyl]benzoyl]-L-glutaminyl-L-tryptophyl-L-alanyl-L-valyl-glycyl-L-histidyl-L-leucyl-L-methioninamide (L115), and N-[4-[[[[4,7,10-Tris (carboxymethyl)-1,4,7,10-tetraazacyclododec-1-yl]acetyl] amino]methyl]phenylacetyl]-L-glutaminyl-L-tryptophyl-L-alanyl-L-valyl-glycyl-L-histidyl-L-leucyl-L-methioninamide (L116), as described in Example II;

FIG. 2C is a chemical structure of the linker used in the synthesis reaction of FIG. 2B for synthesis of N-[4-[2-[[[4,7,10-Tris(carboxymethyl)-1,4,7,10-tetraazacyclododec-1-yl]acetyl]amino]ethoxy]benzoyl]-L-glutaminyl-L-tryptophyl-L-alanyl-L-valyl-glycyl-L-histidyl-L-leucyl-L-methioninamide (L73), as described in Example II;

FIG. 2D is a chemical structure of the linker used in the synthesis reaction of FIG. 2B for synthesis of N-[3-[[[[4,7,10-Tris(carboxymethyl)-1,4,7,10-tetraazacyclododec-1-yl] acetyl]amino]methyl]benzoyl]-L-glutaminyl-L-tryptophyl-L-alanyl-L-valyl-glycyl-L-histidyl-L-leucyl-L-methioninamide (L115), as described in Example II;

FIG. 2E is a chemical structure of the linker used in the synthesis reaction of FIG. 2B for synthesis of N-[4-[[[[4,7,10-Tris(carboxymethyl)-1,4,7,10-tetraazacyclododec-1-yl] acetyl]amino]methyl]phenylacetyl]-L-glutaminyl-L-tryptophyl-L-alanyl-L-valyl-glycyl-L-histidyl-L-leucyl-L-methioninamide (L116), as described in Example II;

FIG. 6E is a chemical structure of 2-[(1,3-Dihydro-1,3-dioxo-2H-isoindol-2-yl)methyl]benzoic acid (C), as described in Example VI;

FIG. 6F is a chemical structure of 2-(aminomethyl)benzoic acid (D), as described in Example VI;

FIG. 6G is a chemical structure of 2-[[[9H-Fluoren-9-ylmethoxy)carbonyl]amino]methyl]benzoic acid (E), as described in Example VI;

FIG. 6H is a chemical structure of 4-(aminomethyl)-3-nitrobenzoic acid (G), as described in Example VI;

FIG. 6I is a chemical structure of 4-[[[9H-Fluoren-9-ylmethoxy)carbonyl]amino]methyl]-3-nitrobenzoic acid (H), as described in Example VI;

DETAILED DESCRIPTION OF THE INVENTION

Figure 1A:
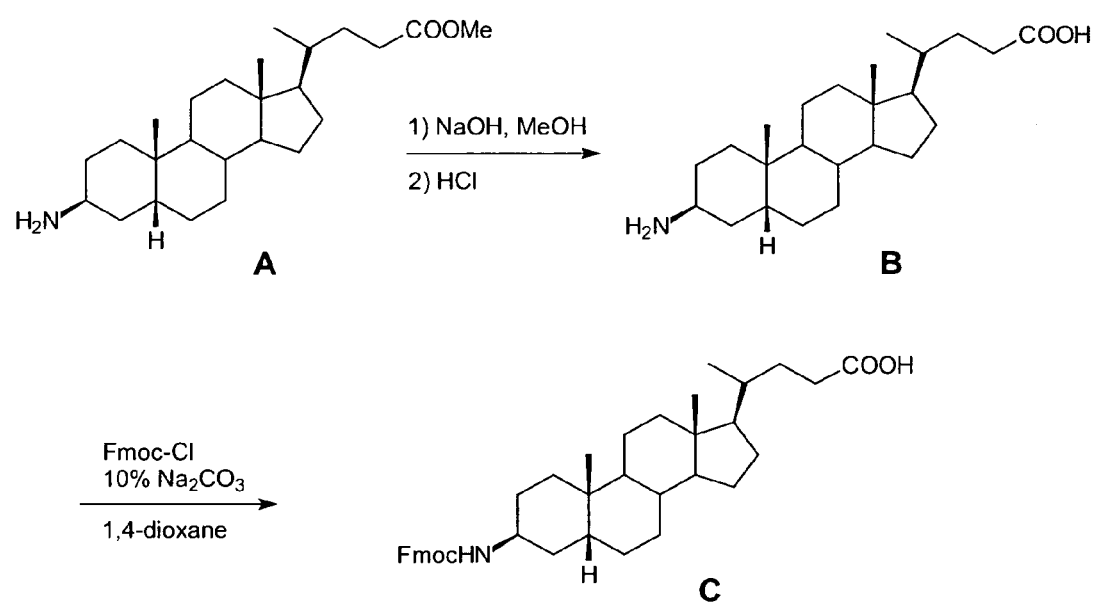
FIG. 1A is a graphical representation of a series of chemical reactions for the synthesis of intermediate C ((3β,5β)-3-(9H-Fluoren-9-ylmethoxy)aminocholan-24-oic acid), from A (Methyl-(3β,5β)-3-aminocholan-24-ate) and B ((3β,5β)-3-aminocholan-24-oic acid), as described in Example I.

In the following description, various aspects of the present invention will be further elaborated. For purposes of explanation, specific configurations and details are set forth in order to provide a thorough understanding of the present invention. However, it will also be apparent to one skilled in the art that the present invention may be practiced without the specific details. Furthermore, well known features may be omitted or simplified in order not to obscure the present invention.

In an embodiment of the present invention, there is provided a new and improved compound for use in radio-diagnostic imaging or radiotherapy. The compound includes a chemical moiety capable of complexing a medically useful metal ion or radionuclide (metal chelator) attached to a GRP receptor targeting peptide by a linker or spacer group.

In general, compounds of the present invention may have the formula:

M-N-O-P-G wherein M is the metal chelator (in the form complexed with a metal radionuclide or not), N-O-P is the linker, and G is the GRP receptor targeting peptide. Each of the metal chelator, linker, and GRP receptor targeting peptide is described in the discussion that follow.

In another embodiment of the present invention, there is provided a new and improved linker or spacer group which is capable of linking a metal chelator to a GRP receptor targeting peptide. In general, linkers of the present invention may have the formula:

N-O-P wherein each of N, O and P are defined throughout the specification.

Compounds meeting the criteria defined herein were discovered to have improved pharmacokinetic properties compared to other radiolabeled GRP receptor targeting peptide conjugates known in the art. For example, compounds containing the linkers of the present invention were retained in the bloodstream longer, and thus had a longer half life than prior known compounds. The longer half life was medically beneficial because it permitted better tumor targeting which is useful for diagnostic imaging, and especially for therapeutic uses, where the cancerous cells and tumors receive greater amounts of the radiolabeled peptides.

1. Metal Chelator

The term "metal chelator" refers to a molecule that forms a complex with a metal atom, wherein said complex is stable under physiological conditions. That is, the metal will remain complexed to the chelator backbone in vivo. More particularly, a metal chelator is a molecule that complexes to a radionuclide metal to form a metal complex that is stable under physiological conditions and which also has at least one reactive functional group for conjugation with the linker N-O-P. The metal chelator M may be any of the metal chelators known in the art for complexing a medically useful metal ion or radionuclide. The metal chelator may or may not be complexed with a metal radionuclide. Furthermore, the metal chelator can include an optional spacer such as a single amino acid (e.g., Gly) which does not complex with the metal, but which creates a physical separation between the metal chelator and the linker.

The metal chelators of the invention may include, for example, linear, macrocyclic, terpyridine, and $N_3S$, $N_2S_2$, or $N_4$ chelators (see also, U.S. Pat. Nos. 5,367,080, 5,364,613, 5,021,556, 5,075,099, 5,886,142, the disclosures of which are incorporated by reference herein in their entirety), and other chelators known in the art including, but not limited to, HYNIC, DTPA, EDTA, DOTA, TETA, and bisamino bisthiol (BAT) chelators (see also U.S. Pat. No. 5,720,934). For example, $N_4$ chelators are described in U.S. Pat. Nos. 6,143,274; 6,093,382; 5,608,110; 5,665,329; 5,656,254; and 5,688,487, the disclosures of which are incorporated by reference herein in their entirety. Certain $N_3S$ chelators are described in PCT/CA94/00395, PCT/CA94/00479, PCT/CA95/00249 and in U.S. Pat. Nos. 5,662,885; 5,976,495; and 5,780,006, the disclosures of which are incorporated by reference herein in their entirety. The chelator may also include derivatives of the chelating ligand mercapto-acetyl-glycyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in Liu and Edwards, *Chem Rev.* 1999, 99, 2235–2268 and references therein, the disclosures of which are incorporated by reference herein in their entirety.

The metal chelator may also include complexes containing ligand atoms that are not donated to the metal in a tetradentate array. These include the boronic acid adducts of technetium and rhenium dioximes, such as those described in U.S. Pat. Nos. 5,183,653; 5,387,409; and 5,118,797, the disclosures of which are incorporated by reference herein, in their entirety.

Examples of preferred chelators include, but are not limited to, diethylenetriamine pentaacetic acid (DTPA), 1,4,7,10-tetraazacyclotetradecane-1,4,7,10-tetraacetic acid (DOTA), 1-substituted 1,4,7,-tricarboxymethyl 1,4,7,10 tetraazacyclododecane triacetic acid (DO3A), ethylenediaminetetraacetic acid (EDTA), and 1,4,8,11-tetraazacyclotetradecane-1,4,8,11-tetraacetic acid (TETA). Additional chelating ligands are ethylenebis-(2-hydroxy-phenylglycine) (EHPG), and derivatives thereof, including 5-Cl-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl-DTPA; bis-2(hydroxybenzyl)-ethylene-diaminediacetic acid (HBED) and derivatives thereof; the class of macrocyclic compounds which contain at least 3 carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N"-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylenediaminetetraacetic acid (PDTA) and triethylenetetraaminehexaacetic acid (TTHA); derivatives of 1,5,10-N,N',N"-tris(2,3-dihydroxybenzoyl)-tricatecholate (LICAM) and 1,3,5-N,N',N"-tris(2,3-dihydroxybenzoyl) aminomethylbenzene (MECAM). Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143,274, each of which is hereby incorporated by reference in its entirety.

Particularly preferred metal chelators include those of Formula 1, 2 and 3 (for $^{111}$In and radioactive lanthanides, such as, for example $^{177}$Lu, $^{90}$Y, $^{153}$Sm, and $^{166}$Ho) and those of Formula 4, 5 and 6 (for radioactive $^{99m}$Tc, $^{186}$Re, and $^{188}$Re) set forth below. These and other metal chelating groups are described in U.S. Pat. Nos. 6,093,382 and 5,608,110, which are incorporated by reference herein in their entirety. Additionally, the chelating group of formula 3 is described in, for example, U.S. Pat. No. 6,143,274; the chelating group of formula 5 is described in, for example, U.S. Pat. Nos. 5,627,286 and 6,093,382, and the chelating group of formula 6 is described in, for example, U.S. Pat. Nos. 5,662,885; 5,780,006; and 5,976,495, all of which are incorporated by reference. Specific metal chelators of formula 6 include N,N-dimethylGly-Ser-Cys; N,N-dimethylGly-Thr-Cys; N,N-diethylGly-Ser-Cys; N,N-dibenzylGly-Ser-Cys; and other variations thereof. For example, spacers which do not actually complex with the metal radionuclide such as an extra single amino acid Gly, may be attached to these metal chelators (e.g., N,N-dimethylGly-Ser-Cys-Gly; N,N-dimethylGly-Thr-Cys-Gly; N,N-diethylGly-Ser-Cys-Gly; N,N-dibenzylGly-Ser-Cys-Gly). Other useful metal chelators such as all of those disclosed in U.S. Pat. No. 6,334,996, also incorporated by reference (e.g., Dimethylgly-L-t-Butylgly-L-Cys-Gly; Dimethylgly-D-t-Butylgly-L-Cys-Gly; Dimethylgly-L-t-Butylgly-L-Cys, etc.)

Furthermore, sulfur protecting groups such as Acm (acetamidomethyl), trityl or other known alkyl, aryl, acyl, alkanoyl, aryloyl, mercaptoacyl and organothiol groups may be attached to the cysteine amino acid of these metal chelators.

Additionally, other useful metal chelators include:
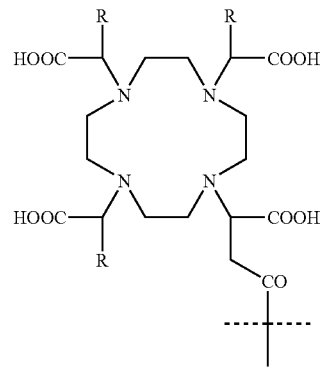 (1)
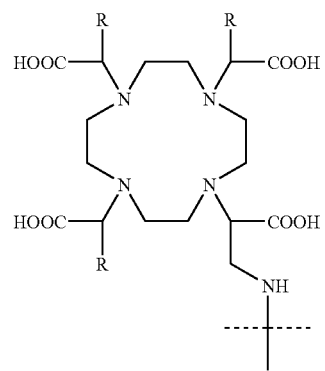 (2)
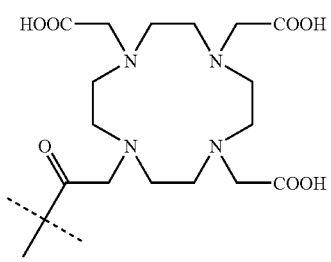 (3)
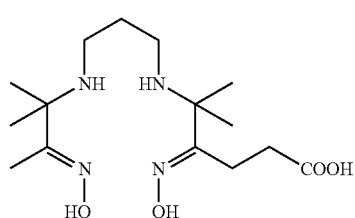 (4a)
-continued
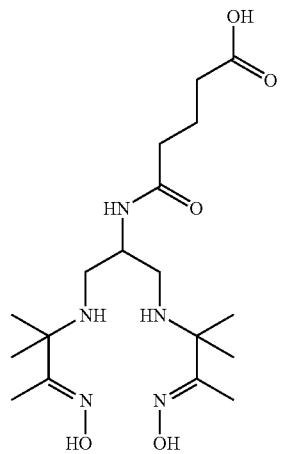 (4b)
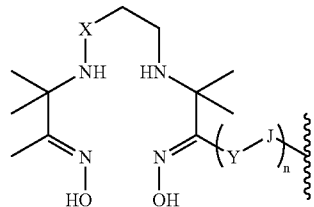 (5a)
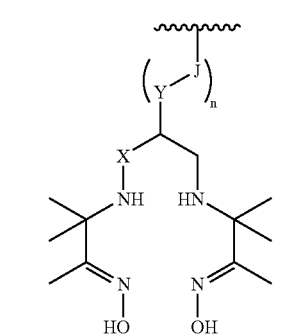 (5b)
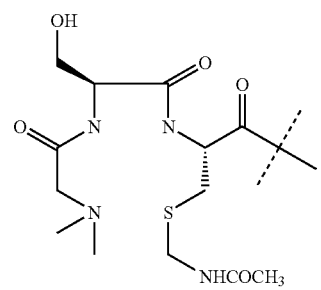 (6)
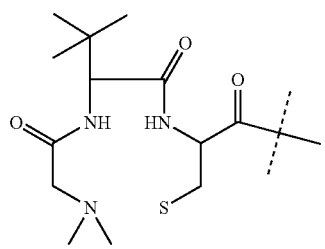 (7)

In the above Formulas 1 and 2, R is alkyl, preferably methyl. In the above Formula 5, X is either $CH_2$ or O, Y is either $C_1$–$C_{10}$ branched or unbranched alkyl; Y is aryl, aryloxy, arylamino, arylaminoacyl; Y is arylalkyl—where the alkyl group or groups attached to the aryl group are $C_1$–$C_{10}$ branched or unbranched alkyl groups, $C_1$–$C_{10}$ branched or unbranched hydroxy or polyhydroxyalkyl groups or polyalkoxyalkyl or polyhydroxy-polyalkoxyalkyl groups, J is C(=O)—, OC(=O)—, $SO_2$—, NC(=O)—, NC(=S)—, N(Y), NC(=NCH$_3$)—, NC(=NH)—, N=N—, homopolyamides or heteropolyamines derived from synthetic or naturally occurring amino acids; all where n is 1–100. J may also be absent. Other variants of these structures are described, for example, in U.S. Pat. No. 6,093,382. In Formula 6, the group S—NHCOCH$_3$ may be replaced with SH or S-Z wherein Z is any of the known sulfur protecting groups such as those described above. Formula 7 illustrates one embodiment of t-butyl compounds useful as a metal chelator. The disclosures of each of the foregoing patents, applications and references are incorporated by reference herein, in their entirety.

In a preferred embodiment, the metal chelator includes cyclic or acyclic polyaminocarboxylic acids such as DOTA (1,4,7,10-tetraazacyclododecane-1,4,7,10-tetraacetic acid), DTPA (diethylenetriaminepentaacetic acid), DTPA-bism-ethylamide, DTPA-bismorpholineamide, DO3A N-[[4,7,10-Tris(carboxymethyl)-1,4,7,10-tetraazacyclododec-1-yl] acetyl, HP-DO3A, DO3A-monoamide and derivatives thereof.

Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au and $^{199}$Au and oxides or nitrides thereof. The choice of metal will be determined based on the desired therapeutic or diagnostic application. For example, for diagnostic purposes (e.g., to diagnose and monitor therapeutic progress in primary tumors and metastases), the preferred radionuclides include $^{64}$Cu, $^{67}$Ga, $^{68}$Ga, $^{99m}$Tc, and $^{111}$In, with $^{99m}$Tc and $^{111}$In being especially preferred. For therapeutic purposes (e.g., to provide radiotherapy for primary tumors and metastasis related to cancers of the prostate, breast, lung, etc.), the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$Yb, $^{177}$Lu, $^{186/188}$Re, and $^{199}$Au, with $^{177}$Lu and $^{90}$Y being particularly preferred. $^{99m}$Tc is particularly useful and is a preferred for diagnostic radionuclide because of its low cost, availability, imaging properties, and high specific activity. The nuclear and radioactive properties of $^{99m}$Tc make this isotope an ideal scintigraphic imaging agent. This isotope has a single photon energy of 140 keV and a radioactive half-life of about 6 hours, and is readily available from a $^{99}$Mo-$^{99m}$Tc generator. For example, the $^{99m}$Tc labeled peptide can be used to diagnose and monitor therapeutic progress in primary tumors and metastases. Peptides labeled with $^{177}$Lu, $^{90}$Y or other therapeutic radionuclides can be used to provide radiotherapy for primary tumors and metastasis related to cancers of the prostate, breast, lung, etc.

2A. Linkers Containing at Least One Non-alpha Amino Acid

In one embodiment of the invention, the linker N-O-P contains at least one non-alpha amino acid. Thus, in this embodiment of the linker N-O-P, N is 0 (where 0 means it is absent), an alpha or non-alpha amino acid or other linking group;

O is an alpha or non-alpha amino acid; and

P is 0, an alpha or non-alpha amino acid or other linking group, wherein at least one of N, O or P is a non-alpha amino acid. Thus, in one example, N=Gly, O=a non-alpha amino acid, and P=0.

Alpha amino acids are well known in the art, and include naturally occurring and synthetic amino acids.

Non-alpha amino acids also include those which are naturally occurring or synthetic. Preferred non-alpha amino acids include:

8-amino-3,6-dioxaoctanoic acid;

N-4-aminoethyl-N-1-acetic acid; and polyethylene glycol derivatives having the formula $NH_2$—$(CH_2CH_2O)n$-$CH_2CO_2H$ or $NH_2$—$(CH_2CH_2O)$n-$CH_2CH_2CO_2H$ where n=2 to 100.

Examples of compounds having the formula M-N-O-P-G which contain linkers with at least one non-alpha amino acid are listed in Table 1.

TABLE 1

Compounds Containing Linkers With At Least One Non-alpha Amino Acid

| Compound | HPLC method[1] | HPLC RT[2] | MS[3] | IC50[5] | M | N | O | P | G* |
|---|---|---|---|---|---|---|---|---|---|
| L1 | 10–40% B | 5.43 | 1616.6 | 5 | N,N-dimethylglycine-Ser-Cys(Acm)-Gly | Lys | 8-amino-3,6-dioxaoctanoic acid | none | BBN(7-14) |
| L2 | 10–40% B | 5.47 | 1644.7 | 3 | N,N-dimethylglycine-Ser-Cys(Acm)-Gly | Arg | 8-amino-3,6-dioxaoctanoic acid | none | BBN(7-14) |
| L3 | 10–40% B | 5.97 | 1604.6 | >50 | N,N-dimethylglycine-Ser-Cys(Acm)-Gly | Asp | 8-amino-3,6-dioxaoctanoic acid | none | BBN(7-14) |
| L4 | 10–40% B | 5.92 | 1575.5 | 4 | N,N-dimethylglycine-Ser-Cys(Acm)-Gly | Ser | 8-amino-3,6-dioxaoctanoic acid | none | BBN(7-14) |
| L5 | 10–40% B | 5.94 | 1545.5 | 9 | N,N-dimethylglycine-Ser-Cys(Acm)-Gly | Gly | 8-amino-3,6-dioxaoctanoic acid | none | BBN(7-14) |
| L6 | 10–30% B | 7.82 | 1639 (M + Na) | >50 | N,N-dimethyl-glycine-Ser-Cys(Acm)-Gly | Glu | 8-amino-3,6-dioxaoctanoic acid | none | BBN(7-14) |

TABLE 1-continued

Compounds Containing Linkers With At Least One Non-alpha Amino Acid

| Compound | HPLC method[1] | HPLC RT[2] | MS[3] | IC50[5] | M | N | O | P | G* |
|---|---|---|---|---|---|---|---|---|---|
| L7 | 10–30% B | 8.47 | 1581 (M + Na) | 7 | N,N-dimethylglycine-Ser-Cys(Acm)-Gly | Dala | 8-amino-3,6-dioxaoctanoic acid | none | BBN(7-14) |
| L8 | 10–30% B | 6.72 | 1639 (M + Na) | 4 | N,N-dimethylglycine-Ser-Cys(Acm)-Gly | 8-amino-3,6-dioxaoctanoic acid | Lys | none | BBN(7-14) |
| L9 | 10–30% B | 7.28 | 823.3 (M + 2/2) | 6 | N,N-dimethylglycine-Ser-Cys(Acm)-Gly | 8-amino-3,6-dioxaoctanoic acid | Arg | none | BBN(7-14) |
| L10 | 10–30% B | 7.94 | 1625.6 (M + Na) | >50 | N,N-dimethylglycine-Ser-Cys(Acm)-Gly | 8-amino-3,6-dioxaoctanoic acid | Asp | none | BBN(7-14) |
| L11 | 10–30% B | 7.59 | 1575.6 | 36 | N,N-dimethylglycine-Ser-Cys(Acm)-Gly | 8-amino-3,6-dioxaoctanoic acid | Ser | none | BBN(7-14) |
| L12 | 10–30% B | 7.65 | 1567.5 (M + Na) | >50 | N,N-dimethylglycine-Ser-Cys(Acm)-Gly | 8-amino-3,6-dioxaoctanoic acid | Gly | none | BBN(7-14) |
| L13 | 10–30% B | 7.86 | 1617.7 | >50 | N,N-dimethylglycine-Ser-Cys(Acm)-Gly | 8-amino-3,6-dioxaoctanoic acid | Glu | none | BBN(7-14) |
| L14 | 10–30% B | 7.9 | 1581.7 (M + Na) | 11 | N,N-dimethylglycine-Ser-Cys(Acm)-Gly | 8-amino-3,6-dioxaoctanoic acid | Dala | none | BBN(7-14) |
| L15 | 10–30% B | 7.84 | 1656.8 (M + Na) | 11.5 | N,N-dimethylglycine-Ser-Cys(Acm)-Gly | 8-amino-3,6-dioxaoctanoic acid | 8-amino-3,6-dioxaoctanoic acid | none | BBN(7-14) |
| L16 | 10–30% B | 6.65 | 1597.4 (M + Na) | 17 | N,N-dimethylglycine-Ser-Cys(Acm)-Gly | 8-amino-3,6-dioxaoctanoic acid | 2,3-diaminopropionic acid | none | BBN(7-14) |
| L17 | 10–30% B | 7.6 | 1488.6 | 8 | N,N-dimethylglycine-Ser-Cys(Acm)-Gly | none | 8-amino-3,6-dioxaoctanoic acid | none | BBN(7-14) |
| L18 | 10–30% B | 7.03 | 1574.6 | 7.8 | N,N-dimethylglycine-Ser-Cys(Acm)-Gly | 2,3-diaminopropionic acid | 8-amino-3,6-dioxaoctanoic acid | none | BBN(7-14) |
| L19 | 10–35% B | 5.13 | 1603.6 | >50 | N,N-dimethylglycine-Ser-Cys(Acm)-Gly | Asp | 8-amino-3,6-dioxaoctanoic acid | Gly | BBN(7-14) |
| L20 | 10–35% B | 5.19 | 1603.6 | 37 | N,N-dimethylglycine-Ser-Cys(Acm)-Gly | 8-amino-3,6-dioxaoctanoic acid | Asp | Gly | BBN(7-14) |
| L21 | 10–35% B | 5.04 | 1575.7 | 46 | N,N-dimethylglycine-Ser-Cys(Acm)-Gly | 8-amino-3,6-dioxaoctanoic acid | Ser | Gly | BBN(7-14) |
| L22 | 10–35% B | 4.37 | 1644.7 | 36 | N,N-dimethylglycine-Ser-Cys(Acm)-Gly | 8-amino-3,6-dioxaoctanoic acid | Arg | Gly | BBN(7-14) |
| L23 | 10–35% B | 5.32 | 1633.7 | >50 | N,N-dimethylglycine- | 8-amino- | 8-amino-3,6-dioxaoctanoic | Gly | BBN(7-14) |

TABLE 1-continued

Compounds Containing Linkers With At Least One Non-alpha Amino Acid

| Compound | HPLC method[1] | HPLC RT[2] | MS[3] | IC50[5] | M | N | O | P | G* |
|---|---|---|---|---|---|---|---|---|---|
| | | | | | Ser-Cys(Acm)-Gly | 3,6-dioxaoctanoic acid | acid | | |
| L24 | 10–35% B | 4.18 | 1574.6 | 38 | N,N-dimethylglycine-Ser-Cys(Acm)-Gly | 8-amino-3,6-dioxaoctanoic acid | 2,3-diaminopropionic acid | Gly | BBN(7-14) |
| L25 | 10–35% B | 4.24 | 1616.6 | 26 | N,N-dimethylglycine-Ser-Cys(Acm)-Gly | 8-amino-3,6-dioxaoctanoic acid | Lys | Gly | BBN(7-14) |
| L26 | 10–35% B | 4.45 | 1574.6 | 30 | N,N-dimethylglycine-Ser-Cys(Acm)-Gly | 2,3-diaminopropionic acid | 8-amino-3,6-dioxaoctanoic acid | Gly | BBN(7-14) |
| L27 | 10–35% B | 4.38 | 1627.3 | >50 | N,N-dimethylglycine-Ser-Cys(Acm)-Gly | N-4-aminoethyl-N-1-piperazineacetic acid | Asp | none | BBN(7-14) |
| L28 | 10–35% B | 4.1 | 1600.3 | 25 | N,N-dimethylglycine-Ser-Cys(Acm)-Gly | N-4-aminoethyl-N-1-piperazineacetic acid | Ser | none | BBN(7-14) |
| L29 | 10–35% B | 3.71 | 1669.4 | 36 | N,N-dimethylglycine-Ser-Cys(Acm)-Gly | N-4-aminoethyl-N-1-piperazineacetic acid | Arg | none | BBN(7-14) |
| L30 | 10–35% B | 4.57 | 1657.2 | 36 | N,N-dimethylglycine-Ser-Cys(Acm)-Gly | N-4-aminoethyl-N-1-piperazineacetic acid | 8-amino-3,6-dioxaoctanoic acid | none | BBN(7-14) |
| L31 | 10–35% B | 3.69 | 1598.3 | >50 | N,N-dimethylglycine-Ser-Cys(Acm)-Gly | N-4-aminoethyl-N-1-piperazineacetic acid | 2,3-diaminopropionic acid | none | BBN(7-14) |
| L32 | 10–35% B | 3.51 | 1640.3 | 34 | N,N-dimethylglycine-Ser-Cys(Acm)-Gly | N-4-aminoethyl-N-1-piperazineacetic acid | Lys | none | BBN(7-14) |
| L33 | 10–35% B | 4.29 | 1584.5 | >50 | N,N-dimethylglycine-Ser-Cys(Acm)-Gly | N-1-piperazineacetic acid | Asp | none | BBN(7-14) |
| L34 | 10–35% B | 4.07 | 1578.7 (M + Na) | 38 | N,N-dimethylglycine-Ser-Cys(Acm)-Gly | N-1-piperazineacetic acid | Ser | none | BBN(7-14) |
| L35 | 10–35% B | 3.65 | 1625.6 | 26 | N,N-dimethylglycine-Ser-Cys(Acm)-Gly | N-1-piperazineacetic acid | Arg | none | BBN(7-14) |
| L36 | 10–35% B | 4.43 | 1636.6 | 7 | N,N-dimethylglycine-Ser-Cys(Acm)-Gly | N-1-piperazineacetic acid | 8-amino-3,6-dioxaoctanoic acid | none | BBN(7-14) |
| L37 | 10–35% B | 3.66 | 1555.7 | 23 | N,N-dimethylglycine-Ser-Cys(Acm)-Gly | N-1-piperazineacetic acid | 2,3-diaminopropionic acid | none | BBN(7-14) |
| L38 | 10–35% B | 3.44 | 1619.6 | 7 | N,N-dimethylglycine-Ser-Cys(Acm)-Gly | N-1-piperazineacetic acid | Lys | none | BBN(7-14) |
| L42 | 30–50% B | 5.65 | 1601.6 | 25 | N,N-dimethylglycine-Ser-Cys(Acm)-Gly | 4-Hydroxyproline | 8-amino-3,6-dioxaoctanoic acid | none | BBN(7-14) |

TABLE 1-continued

Compounds Containing Linkers With At Least One Non-alpha Amino Acid

| Compound | HPLC method[1] | HPLC RT[2] | MS[3] | IC50[5] | M | N | O | P | G* |
|---|---|---|---|---|---|---|---|---|---|
| L48 | 30–50% B | 4.47 | 1600.5 | 40 | N,N-dimethylglycine-Ser-Cys(Acm)-Gly | 4-aminoproline | 8-amino-3,6-dioxaoctanoic acid | none | BBN(7-14) |
| L51 | 15–35% B | 5.14 | 1673.7 | 49 | N,N-dimethylglycine-Ser-Cys(Acm)-Gly | Lys | 8-amino-3,6-dioxaoctanoic acid | Gly | BBN(7-14) |
| L52 | 15–35% B | 6.08 | 1701.6 | 14 | N,N-dimethylglycine-Ser-Cys(Acm)-Gly | Arg | 8-amino-3,6-dioxaoctanoic acid | Gly | BBN(7-14) |
| L53 | 15–35% B | 4.16 | 1632.6 | 10 | N,N-dimethylglycine-Ser-Cys(Acm)-Gly | Ser | 8-amino-3,6-dioxaoctanoic acid | Gly | BBN(7-14) |
| L54 | 15–35% B | 4.88 | 1661.6 | >50 | N,N-dimethylglycine-Ser-Cys(Acm)-Gly | Asp | 8-amino-3,6-dioxaoctanoic acid | Gly | BBN(7-14) |
| L55 | 15–35% B | 4.83 | 1683.4 (M + Na) | 43 | N,N-dimethylglycine-Ser-Cys(Acm)-Gly | 8-amino-3,6-dioxaoctanoic acid | Asp | Gly | BBN(7-14) |
| L56 | 15–35% B | 4.65 | 1655.7 (M + Na) | 4 | N,N-dimethylglycine-Ser-Cys(Acm)-Gly | 8-amino-3,6-dioxaoctanoic acid | Ser | Gly | BBN(7-14) |
| L57 | 15–35% B | 4.9 | 1701.8 | 50 | N,N-dimethylglycine-Ser-Cys(Acm)-Gly | 8-amino-3,6-dioxaoctanoic acid | Arg | Gly | BBN(7-14) |
| L58 | 15–35% B | 4.22 | 846.4 (M + H/2) | >50 | N,N-dimethylglycine-Ser-Cys(Acm)-Gly | 8-amino-3,6-dioxaoctanoic acid | 8-amino-3,6-dioxaoctanoic acid | Gly | BBN(7-14) |
| L59 | 15–35% B | 4.03 | 1635.5 | 42 | N,N-dimethylglycine-Ser-Cys(Acm)-Gly | 8-amino-3,6-dioxaoctanoic acid | 2,3-diaminopropionic acid | Gly | BBN(7-14) |
| L60 | 15–35% B | 4.11 | 1696.6 (M + Na) | 20 | N,N-dimethylglycine-Ser-Cys(Acm)-Gly | 8-amino-3,6-dioxaoctanoic acid | Lys | Gly | BBN(7-14) |
| L61 | 15–35% B | 4.32 | 1631.4 | 43 | N,N-dimethylglycine-Ser-Cys(Acm)-Gly | 2,3-diaminopropionic acid | 8-amino-3,6-dioxaoctanoic acid | Gly | BBN(7-14) |
| L78 | 20–40% B | 6.13 | 1691.4 (M + Na) | 35 | DO3A-monoamide | 8-amino-3,6-dioxaoctanoic acid | Diaminopropionic acid | none | BBN(7-14) |
| L79 | 20–40% B | 7.72 | 1716.8 (M + Na) | 42 | DO3A-monoamide | 8-amino-3,6-dioxaoctanoic acid | Biphenylalanine | none | BBN(7-14) |
| L80 | 20–40% B | 7.78 | 1695.9 | >50 | DO3A-monoamide | 8-amino-3,6-dioxaoctanoic acid | Diphenylalanine | none | BBN(7-14) |
| L81 | 20–40% B | 7.57 | 1513.6 | 37.5 | DO3A-monoamide | 8-amino-3,6-dioxaoctanoic acid | 4-Benzoylphenylalanine | none | BBN(7-14) |
| L92 | 15–30% B | 5.63 | 1571.6 | 5 | DO3A-monoamide | 5-aminopentanoic acid | 8-amino-3,6-dioxaoctanoic acid | none | BBN(7-14) |
| L94 | 20–36% B | 4.19 | 1640.8 (M + Na) | 6.2 | DO3A-monoamide | 8-amino-3,6-dioxaoctanoic acid | D-Phenylalanine | none | BBN(7-14) |

TABLE 1-continued

Compounds Containing Linkers With At Least One Non-alpha Amino Acid

| Compound | HPLC method[1] | HPLC RT[2] | MS[3] | IC50[5] | M | N | O | P | G* |
|---|---|---|---|---|---|---|---|---|---|
| L110 | 15–45% B | 5.06 | 1612.7 | 36 | DO3A-monoamide | dioxaoctanoic acid 8-aminooctanoic acid | 8-amino-3,6-dioxaoctanoic acid | none | BBN(7-14) |

*BBN(7-14) is [SEQ ID NO: 1]
[1]HPLC method refers to the 10 minute time for the HPLC gradient.
[2]HPLC RT refers to the retention time of the compound in the HPLC.
[3]MS refers to mass spectra where molecular weight is calculated from mass/unit charge (m/e).
[4]$IC_{50}$ refers to the concentration of compound to inhibit 50% binding of iodinated bombesin to a GRP receptor on cells.

2B. Linkers Containing at Least One Substituted Bile Acid

In another embodiment of the present invention, the linker N-O-P contains at least one substituted bile acid. Thus, in this embodiment of the linker N-O-P, N is 0 (where 0 means it is absent), an alpha amino acid, a substituted bile acid or other linking group;
O is an alpha amino acid or a substituted bile acid; and
P is 0, an alpha amino acid, a substituted bile acid or other linking group,
wherein at least one of N, O or P is a substituted acid.

Bile acids are found in bile (a secretion of the liver) and are steroids having a hydroxyl group and a five carbon atom side chain terminating in a carboxyl group. In substituted bile acids, at least one atom such as a hydrogen atom of the bile acid is substituted with another atom, molecule or chemical group. For example, substituted bile acids include those having a 3-amino, 24-carboxyl function optionally substituted at positions 7 and 12 with hydrogen, hydroxyl or keto functionality.

Other useful substituted bile acids in the present invention include substituted cholic acids and derivatives thereof. Specific substituted cholic acid derivatives include:
(3β,5β)-3-aminocholan-24-oic acid;
(3β,5β,12α)-3-amino-12-hydroxycholan-24-oic acid;
(3β,5β,7α,12α)-3-amino-7,12-dihydroxycholan-24-oic acid;
Lys-(3,6,9)-trioxaundecane-1,11-dicarbonyl-3,7-dideoxy-3-aminocholic acid);
(3β,5β,7α)-3-amino-7-hydroxy-12-oxocholan-24-oic acid; and
(3β,5β,7α)-3-amino-7-hydroxycholan-24-oic acid.

Examples of compounds having the formula M-N-O-P-G which contain linkers with at least one substituted bile acid are listed in Table 2.

TABLE 2

Compounds Containing Linkers With At Least One Substituted Bile Acid

| Compound | HPLC method[1] | HPLC RT[2] | MS[3] | IC50[5] | M | N | O | P | G* |
|---|---|---|---|---|---|---|---|---|---|
| L62 | 20–80% B | 3.79 | 1741.2 | >50 | DO3A-monoamide | Gly | (3β,5β)-3-aminocholan-24-oic acid | none | BBN(7-14) |
| L63 | 20–80% B | 3.47 | 1757.0 | 23 | DO3A-monoamide | Gly | (3β,5β,12α)-3-amino-12-hydroxycholan-24-oic acid | none | BBN(7-14) |
| L64 | 20–50% B | 5.31 | 1773.7 | 8.5 | DO3A-monoamide | Gly | (3β,5β,7α,12α)-3-amino-7,12-dihydroxycholan-24-oic acid | none | BBN(7-14) |
| L65 | 20–80% B | 3.57 | 2246.2 | >50 | DO3A-monoamide | Gly | Lys-(3,6,9-trioxaundecane-1,11-dicarbonyl-3,7-dideoxy-3-aminocholic acid) | Arg | BBN(7-14) |
| L66 | 20–80% | 3.79 | 2245.8 | >50 | (3β,5β,7α,12α)-3-amino-7,12-dihydroxycholan-24-oic acid-3,6,9-trioxaundecane-1,11-dicarbonyl | | Lys(DO3A-monoamide-Gly) | Arg | BBN(7-14) |
| L67 | 20–80% | 3.25 | 1756.9 | 4.5 | DO3A-monoamide | Gly | (3β,5β,7α,12α)-3-amino-12- | none | BBN(7-14) |

TABLE 2-continued

Compounds Containing Linkers With At Least One Substituted Bile Acid

| Compound | HPLC method[1] | HPLC RT[2] | MS[3] | IC50[5] M | N | O | P | G* |
|---|---|---|---|---|---|---|---|---|
| L69 | 20–80% | 3.25 | 1861.27 | not tested | DO3A-monoamide | 1-amino-3,6-dioxaoctanoic acid | oxacholan-24-oic acid (3β,5β,7α,12α)-3-amino-7,12-dihydroxycholan-24-oic acid | none | BBN(7-14) |

*BBN(7-14) is [SEQ ID NO: 1]
[1]HPLC method refers to the 10 minute time for the HPLC gradient.
[2]HPLC RT refers to the retention time of the compound in the HPLC.
[3]MS refers to mass spectra where molecular weight is calculated from mass/unit charge (m/e).
[4]IC$_{50}$ refers to the concentration of compound to inhibit 50% binding of iodinated bombesin to a GRP receptor on cells.

2C. Linkers Containing at Least One Non-Alpha Amino Acid with a Cyclic Group In yet another embodiment of the present invention, the linker N-O-P contains at least one non-alpha amino acid with a cyclic group. Thus, in this embodiment of the linker N-O-P, N is 0 (where 0 means it is absent), an alpha amino acid, a non-alpha amino acid with a cyclic group or other linking group;

O is an alpha amino acid or a non-alpha amino acid with a cyclic group; and

P is 0, an alpha amino acid, a non-alpha amino acid with a cyclic group, or other linking group, wherein at least one of N, O or P is a non-alpha amino acid with a cyclic group.

Non-alpha amino acids with a cyclic group include substituted phenyl, biphenyl, cyclohexyl or other amine and carboxyl containing cyclic aliphatic or heterocyclic moieties. Examples of such include:

4-aminobenzoic acid
4-aminomethyl benzoic acid
trans-4-aminomethylcyclohexane carboxylic acid
4-(2-aminoethoxy)benzoic acid
isonipecotic acid
2-aminomethylbenzoic acid
4-amino-3-nitrobenzoic acid
4-(3-carboxymethyl-2-keto-1-benzimidazolyl-piperidine
6-(piperazin-1-yl)-4-(3H)-quinazolinone-3-acetic acid
(2S,5S)-5-amino-1,2,4,5,6,7-hexahydro-azepino[3,21-hi]indole-4-one-2-carboxylic acid
(4S,7R)-4-amino-6-aza-5-oxo-9-thiabicyclo[4.3.0]nonane-7-carboxylic acid
3-carboxymethyl-1-phenyl-1,3,8-triazaspiro[4.5]decan-4-one
N1-piperazineacetic acid
N-4-aminoethyl-N-1-piperazineacetic acid
(3S)-3-amino-1-carboxymethylcaprolactam
(2S,6S,9)-6-amino-2-carboxymethyl-3,8-diazabicyclo-[4,3,0]-nonane-1,4-dione Examples of compounds having the formula M-N-O-P-G which contain linkers with at least one alpha amino acid with a cyclic group are listed in Table 3.

TABLE 3

Compounds Containing Linkers Related To Amino-(Phenyl, Biphenyl, Cycloalkyl Or Heterocyclic) Carboxylates

| Compound | HPLC method[1] | HPLC RT[2] | MS[3] | IC50[5] M | N | O | P | G* |
|---|---|---|---|---|---|---|---|---|
| L70 | 10–40% B | 6.15 | 1502.6 | 5 | DO3A-monoamide | Gly | 4-aminobenzoic acid | none | BBN(7-14) |
| L71 | | | 1482.2 (M + Na) | 7 | DO3A-monoamide | none | 4-aminomethyl benzoic acid | none | BBN(7-14) |
| L72 | | | 1504.0 (M + K) | 8 | DO3A-monoamide | none | trans-4-aminomethylcyclohexyl carboxylic acid | none | BBN(7-14) |
| L73 | 5–35% | 7.01 | 1489.8 | 5 | DO3A-monoamide | none | 4-(2-aminoethoxy)benzoic acid | none | BBN(7-14) |
| L74 | 5–35% | 6.49 | 1494.8 | 7 | DO3A-monoamide | Gly | isonipecotic acid | none | BBN(7-14) |
| L75 | 5–35% | 6.96 | 1458.0 | 23 | DO3A-monoamide | none | 2-aminomethylbenzoic acid | none | BBN(7-14) |
| L76 | 5–35% | 7.20] | 1502.7 | 4 | DO3A-monoamide | none | 4-aminomethyl-3-nitrobenzoic acid | none | BBN(7-14) |
| L77 | 20–40% B | 6.17 | 1691.8 (M + Na) | 17.5 | DO3A-monoamide | 8-amino-3,6-dioxa-octanoic acid | 1-Naphthylalanine | none | BBN(7-14) |

TABLE 3-continued

Compounds Containing Linkers Related To Amino-(Phenyl, Biphenyl, Cycloalkyl Or Heterocyclic) Carboxylates

| Compound | HPLC method[1] | HPLC RT[2] | MS[3] | IC50[5] | M | N | O | P | G* |
|---|---|---|---|---|---|---|---|---|---|
| L82 | 20–40% B | 6.18 | 1584.6 | 8 | DO3A-monoamide | none | 4-(3-carboxymethyl-2-keto-1-benzimidazolyl-piperidine | none | BBN(7-14) |
| L83 | 20–40% B | 5.66 | 1597.5 | >50 | DO3A-monoamide | none | 6-(piperazin-1-yl)-4-(3H)-quinazolinone-3-acetic acid | none | BBN(7-14) |
| L84 | 20–40% B | 6.31 | 1555.5 | >50 | DO3A-monoamide | none | (2S,5S)-5-amino-1,2,4,5,6,7-hexahydro-azepino[3,21-hi]indole-4-one-2-carboxylic acid | none | BBN(7-14) |
| L85 | 20–40% B | 5.92 | 1525.5 | >50 | DO3A-monoamide | none | (4S,7R)-4-amino-6-aza-5-oxo-9-thiabicyclo[4.3.0]nonane-7-carboxylic acid | none | BBN(7-14) |
| L87 | 20–40% B | 5.47 | 1593.8 (M + Na) | >50 | DO3A-monoamide | none | 3-carboxymethyl-1-phenyl-1,3,8-triazaspiro[4.5]decan-4-one | none | BBN(7-14) |
| L88 | 20–40% B | 3.84 | 1452.7 | >50 | DO3A-monoamide | none | N1-piperazineacetic acid | none | BBN(7-14) |
| L89 | 20–40% B | 5.68 | 1518.5 (M + Na) | 23 | DO3A-monoamide | none | N-4-aminoethyl-N-1-piperazineacetic acid | none | BBN(7-14) |
| L90 | 20–40% B | 7.95 | 1495.4 | 50 | DO3A-monoamide | none | (3S)-3-amino-1-carboxymethylcaprolactam | none | BBN(7-14) |
| L91 | 20–40% B | 3.97 | 1535.7 | >50 | DO3A-monoamide | none | (2S,6S,9)-6-amino-2-carboxymethyl-3,8-diazabicyclo-[4,3,0]-nonane-1,4-dione | none | BBN(7-14) |
| L93 | 15–30% B | 7.57 | 1564.7 | 5.8 | DO3A-monoamide | 5-aminopentanoic acid | trans-4-aminomethylcyclohexane-1-carboxylic acid | none | BBN(7-14) |
| L95 | 15–35% B | 5.41 | 1604.6 | 14 | DO3A-monoamide | trans-4-aminomethylcyclohexane-1-carboxylic acid | D-Phenylalanine | none | BBN(7-14) |
| L96 | 20–36% B | 4.75 | 1612.7 | 35 | DO3A-monoamide | 4-amino-methylbenzoic acid | 8-amino-3,6-dioxaoctanoic acid | none | BBN(7-14) |
| L97 | 15–35% B | 5.86 | 1598.8 | 4.5 | DO3A-monoamide | 4-benzoyl-(L)-phenylalanine | trans-4-aminomethylcyclohexane-1-carboxylic acid | none | BBN(7-14) |
| L98 | 15–35% B | 4.26 | 1622.7 | 16 | DO3A-monoamide | trans-4-aminomethylcyclohexane-1-carboxylic acid | Arg | none | BBN(7-14) |
| L99 | 15–35% B | 4.1 | 1594.7 | 22 | DO3A-monoamide | trans-4-aminomethylcyclohexane-1-carboxylic acid | Lys | none | BBN(7-14) |
| L100 | 15–35% B | 4.18 | 1613.6 | 10 | DO3A-monoamide | trans-4-aminomethylcyclohexane-1-carboxylic acid | Diphenylalanine | none | BBN(7-14) |

TABLE 3-continued

Compounds Containing Linkers Related To Amino-(Phenyl, Biphenyl, Cycloalkyl Or Heterocyclic) Carboxylates

| Compound | HPLC method[1] | HPLC RT[2] | MS[3] | IC50[5] | M | N | O | P | G* |
|---|---|---|---|---|---|---|---|---|---|
| L101 | 15–35% B | 5.25 | 1536.7 | 25 | DO3A-monoamide | trans-4-aminomethylcyclohexane-1-carboxylic acid | 1-Naphthylalanine | none | BBN(7-14) |
| L102 | 15–35% B | 5.28 | 1610.8 | 9.5 | DO3A-monoamide | trans-4-aminomethylcyclohexane-1-carboxylic acid | 8-amino-3,6-dioxaoctanoic acid | none | BBN(7-14) |
| L103 | 15–35% B | 4.75 | 1552.7 | 24 | DO3A-monoamide | trans-4-aminomethylcyclohexane-1-carboxylic acid | Ser | none | BBN(7-14) |
| L104 | 15–35% B | 3.91 | 1551.7 | 32 | DO3A-monoamide | trans-4-aminomethylcyclohexane-1-carboxylic acid | 2,3-diaminopropionic acid | none | BBN(7-14) |
| L105 | 20–45% B | 7.68 | 1689.7 | 3.5 | DO3A-monoamide | trans-4-aminomethylcyclohexane-1-carboxylic acid | Biphenylalanine | none | BBN(7-14) |
| L106 | 20–45% B | 6.97 | 1662.7 | 3.8 | DO3A-monoamide | trans-4-aminomethylcyclohexane-1-carboxylic acid | (2S,5S)-5-amino-1,2,4,5,6,7-hexahydro-azepino[3,21-hi]indole-4-one-2-carboxylic acid | none | BBN(7-14) |
| L107 | 15–35% B | 5.79 | 1604.7 | 5 | DO3A-monoamide | trans-4-aminomethylcyclohexane-1-carboxylic acid | trans-4-aminomethylcyclohexane-1-carboxylic acid | none | BBN(7-14) |
| L108 | 15–45% B | 6.38 | 1618.7 | 10 | DO3A-monoamide | 8-amino-3,6-dioxaoctanoic acid | Phenylalanine | none | BBN(7-14) |
| L109 | 15–45% B | 6.85 | 1612.7 | 6 | DO3A-monoamide | trans-4-aminomethylcyclohexane-1-carboxylic acid | Phenylalanine | none | BBN(7-14) |
| L111 | 20–45% B | 3.75 | 1628.6 | 8 | DO3A-monoamide | 8-aminooctanoic acid | trans-4-aminomethylcyclohexane-1-carboxylic acid | none | BBN(7-14) |
| L112 | 20–47% B in 9 min | 3.6 | 1536.5 | 4.5 | DO3A-monoamide | none | 4'-aminomethylbiphenyl-1-carboxylic acid | none | BBN(7-14) |
| L113 | 20–47% B in 9 min | 3.88 | 1558.6 (M + Na) | 5 | DO3A-monamide | none | 3'-aminomethylbiphenyl-3-carboxylic acid | none | BBN(7-14) |
| L114 | 10–40% B | 5.47 | 1582.8 | 4.5 | CMDOTA | Gly | 4-aminobenzoic acid | none | BBN(7-14) |
| L124 | 5–35% B | 7.04 | 1489.9 | 8.0 | DO3A-monoamide | none | 4-aminomethylphenoxyacetic acid | none | BBN(7-14) |
| L143 | 5–35% B | 6.85 | 1516.8 | NT** | DO3A-monoamide | Gly | 4-aminophenylacetic acid | none | BBN(7-14) |
| L144 | 5–35% B | 6.85 | 1462.7 | NT | HPDO3A | none | 4-phenoxy | none | BBN(7-14) |
| L145 | 20–80% B | 1.58 | 1459.8 | 5 | DO3A-monoamide | none | 3-aminomethylbenzoic acid | none | BBN(7-14) |

TABLE 3-continued

Compounds Containing Linkers Related To Amino-(Phenyl, Biphenyl, Cycloalkyl Or Heterocyclic) Carboxylates

| Compound | HPLC method[1] | HPLC RT[2] | MS[3] | IC50[5] | M | N | O | P | G* |
|---|---|---|---|---|---|---|---|---|---|
| L146 | 20–80% B | 1.53 | 1473.7 | 9 | DO3A-monoamide | none | 4-aminomethylphenylacetic acid | none | BBN(7-14) |
| L147 | 20–80% B | 1.68 | 1489.7 | NT | DO3A-monoamide | none | 4-aminomethyl-3-methoxybenzoic acid | none | BBN(7-14) |

*BBN(7-14) is [SEQ ID NO: 1]
**NT is defined as "not tested."
[1]HPLC method refers to the 10 minute time for the HPLC gradient.
[2]HPLC RT refers to the retention time of the compound in the HPLC.
[3]MS refers to mass spectra where molecular weight is calculated from mass/unit charge (m/e).
[4]IC$_{50}$ refers to the concentration of compound to inhibit 50% binding of iodinated bombesin to a GRP receptor on cells.

2D. Other Linking Groups

Other linking groups which may be used within the linker N-O-P include a chemical group that serves to couple the GRP receptor targeting peptide to the metal chelator while not adversely affecting either the targeting function of the GRP receptor targeting peptide or the metal complexing function of the metal chelator. Suitable other linking groups include peptides (i.e., amino acids linked together) alone, a non-peptide group (e.g., hydrocarbon chain) or a combination of an amino acid sequence and a non-peptide spacer.

In one embodiment, other linking groups for use within the linker N-O-P include L-glutamine and hydrocarbon chain, or a combination thereof.

In another embodiment, other linking groups for use within the linker N-O-P include a pure peptide linking group consisting of a series of amino acids (e.g., diglycine, triglycine, gly-gly-glu, gly-ser-gly, etc.), in which the total number of atoms between the N-terminal residue of the GRP receptor targeting peptide and the metal chelator in the polymeric chain is ≦12 atoms.

In yet a further embodiment, other linking groups for use within the linker N-O-P can also include a hydrocarbon chain [i.e., $R_1$—$(CH_2)_n$—$R_2$] wherein n is 0–10, preferably n=3 to 9, $R_1$ is a group (e.g., $H_2N$—, HS—, —COOH) that can be used as a site for covalently linking the ligand backbone or the preformed metal chelator or metal complexing backbone; and $R_2$ is a group that is used for covalent coupling to the N-terminal $NH_2$-group of the GRP receptor targeting peptide (e.g., $R_2$ is an activated COOH group). Several chemical methods for conjugating ligands (i.e., chelators) or preferred metal chelates to biomolecules have been well described in the literature [Wilbur, 1992; Parker, 1990; Hermanson, 1996; Frizberg et al., 1995]. One or more of these methods could be used to link either the uncomplexed ligand (chelator) or the radiometal chelate to the linker or to link the linker to the GRP receptor targeting peptides. These methods include the formation of acid anhydrides, aldehydes, arylisothiocyanates, activated esters, or N-hydroxysuccinimides [Wilbur, 1992; Parker, 1990; Hermanson, 1996; Frizberg et al., 1995].

In a preferred embodiment, other linking groups for use within the linker N-O-P may be formed from linker precursors having electrophiles or nucleophiles as set forth below:

LP1: a linker precursor having on at least two locations of the linker the same electrophile E1 or the same nucleophile Nu1;

LP2: a linker precursor having an electrophile E1 and on another location of the linker a different electrophile E2;

LP3: a linker precursor having a nucleophile Nu1 and on another location of the linker a different nucleophile Nu2; or LP4: a linker precursor having one end functionalized with an electrophile E1 and the other with a nucleophile Nu1.

The preferred nucleophiles Nu1/Nu2 include —OH, —NH, —NR, —SH, —HN—$NH_2$, —RN—$NH_2$, and —RN—NHR', in which R' and R are independently selected from the definitions for R given above, but for R' is not H.

The preferred electrophiles E1/E2 include —COOH, —CH═O (aldehyde), —CR═OR' (ketone), —RN—C═S, —RN—C═O, —S—S-2-pyridyl, —$SO_2$—Y, —$CH_2$C(═O)Y, and

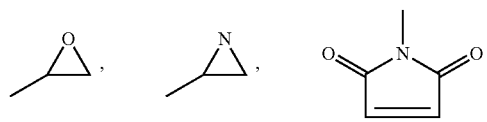

wherein Y can be selected from the following groups:

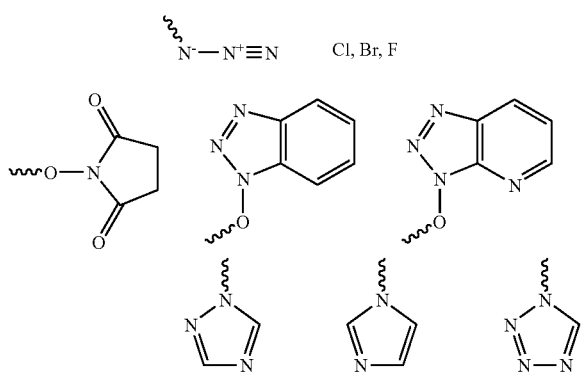

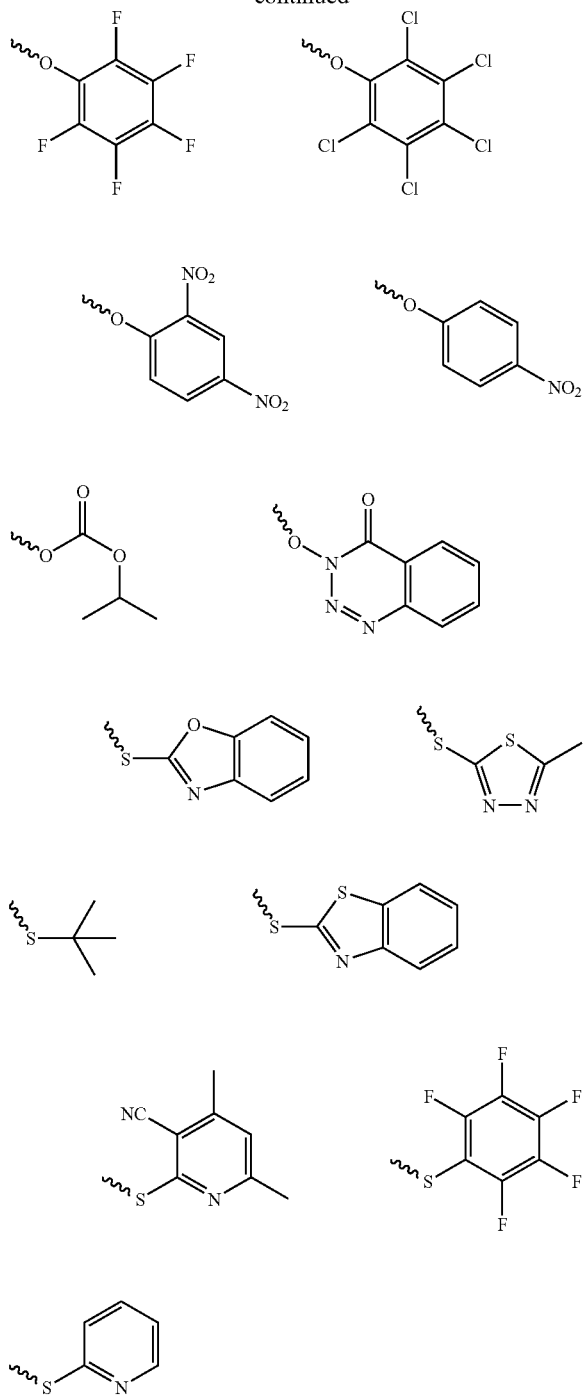

3. GRP Receptor Targeting Peptide

The GRP receptor targeting peptide (i.e., G in the formula M-N-O-P-G) is any peptide, equivalent, derivative or analogue thereof which has a binding affinity for the GRP receptor family.

The GRP receptor targeting peptide may take the form of an agonist or an antagonist. A GRP receptor targeting peptide agonist is known to "activate" the cell following binding with high affinity and may be internalized by the cell. Conversely, GRP receptor targeting peptide antagonists are known to bind only to the GRP receptor on the cell without being internalized by the cell and without "activating" the cell. In a preferred embodiment, the GRP receptor targeting peptide is an agonist.

In a more preferred embodiment of the present invention, the GRP agonist is a bombesin (BBN) analogue and/or a derivative thereof. The BBN derivative or analog thereof preferably contains either the same primary structure of the BBN binding region (i.e., BBN(7-14) [SEQ ID NO:1]) or similar primary structures, with specific amino acid substitutions that will specifically bind to GRP receptors with better or similar binding affinities as BBN alone (i.e., Kd<25 nM). Suitable compounds include peptides, peptidomimetics and analogues and derivatives thereof. The presence of L-methionine (Met) at position BBN-14 will generally confer agonistic properties while the absence of this residue at BBN-14 generally confers antagonistic properties [Hoffken, 1994].

It is well documented in the art that there are a few and selective number of specific amino acid substitutions in the BBN (8-14) binding region (e.g., D-Ala$^{11}$ for L-Gly$^{11}$ or D-Trp$^8$ for L-Trp$^8$), which can be made without decreasing binding affinity [Leban et al., 1994; Qin et al., 1994; Jensen et al., 1993]. In addition, attachment of some amino acid chains or other groups to the N-terminal amine group at position BBN-8 (i.e., the Trp$^8$ residue) can dramatically decrease the binding affinity of BBN analogues to GRP receptors [Davis et al., 1992; Hoffken, 1994; Moody et al., 1996; Coy, et al., 1988; Cai et al., 1994]. In a few cases, it is possible to append additional amino acids or chemical moieties without decreasing binding affinity.

Analogues of BBN receptor targeting peptides include molecules that target the GRP receptors with avidity that is greater than or equal to BBN, as well as muteins, retropeptides and retro-inverso-peptides of GRP or BBN. One of ordinary skill will appreciate that these analogues may also contain modifications which include substitutions, and/or deletions and/or additions of one or several amino acids, insofar that these modifications do not negatively alter the biological activity of the peptides described therein. These substitutions may be carried out by replacing one or more amino acids by their synonymous amino acids. Synonymous amino acids within a group are defined as amino acids that have sufficient physicochemical properties to allow substitution between members of a group in order to preserve the biological function of the molecule. Synonymous amino acids as used herein include synthetic derivatives of these amino acids and may include those listed in the following Table. In the chart and throughout this application amino acids are abbreviated interchangeably either by their three letter or single letter abbreviations, which are well known to the skilled artisan. Thus, for example, T or Thr stands for threonine, K or Lys stands for lysine, P or Pro stands for proline and R or Arg stands for arginine.

| Amino Acids | Synonymous Group |
|---|---|
| Arg | His, Lys, Glu, Gln |
| Pro | Ala, Thr, Gly, N-methyl Ala, pipecolic acid, azetidine carboxylic acid |
| Thr | 3-hydroxy proline, 4-hydroxy proline, Ser, Ala, Gly, His, Gln |
| Lys | Lys, ornithine, Arg, diaminopropionic acid, HArg, His |

Deletions or insertions of amino acids may also be introduced into the defined sequences provided they do not alter the biological functions of said sequences. Preferentially such insertions or deletions should be limited to 1, 2, 3, 4 or 5 amino acids and should not remove or physically disturb or displace amino acids which are critical to the functional conformation. Muteins of the GRP receptor targeting peptides described herein may have a sequence homologous to the sequence disclosed in the present specification in which amino acid substitutions, deletions, or insertions are present at one or more amino acid positions. Muteins may have a biological activity that is at least 40%, preferably at least 50%, more preferably 60–70%, most preferably 80–90% of the peptides described herein. However, they may also have a biological activity greater than the peptides specifically exemplified, and thus do not necessarily have to be identical to the biological function of the exemplified peptides. Analogues of GRP receptor targeting peptides also include peptidomimetics or pseudopeptides incorporating changes to the amide bonds of the, peptide backbone, including thioamides, methylene amines, and E-olefins. Also peptides based on the structure of GRP, BBN or their peptide analogues with amino acids replaced by N-substituted hydrazine carbonyl compounds (also known as aza amino acids) are included in the term analogues as used herein.

The GRP receptor targeting peptide can be prepared by various methods depending upon the selected chelator. The peptide can generally be most conveniently prepared by techniques generally established and known in the art of peptide synthesis, such as the solid-phase peptide synthesis (SPPS) approach. Solid-phase peptide synthesis (SPPS) involves the stepwise addition of amino acid residues to a growing peptide chain that is linked to an insoluble support or matrix, such as polystyrene. The C-terminal residue of the peptide is first anchored to a commercially available support with its amino group protected with an N-protecting agent such as a t-butyloxycarbonyl group (Boc) or a fluorenylmethoxycarbonyl (Fmoc) group. The amino protecting group is removed with suitable deprotecting agents such as TFA in the case of Boc or piperidine for Fmoc and the next amino acid residue (in N-protected form) is added with a coupling agent such as N,N'-dicyclohexylcarbodiimide (DCC), or N,N'-diisopropylcarbodiimide (DIC) or 2-(1H-benzotriazol-1-yl)-1,1,3,3-tetramethyluronium hexafluorophosphate (HBTU). Upon formation of a peptide bond, the reagents are washed from the support. After addition of the final residue, the peptide is cleaved from the support with a suitable reagent such as trifluoroacetic acid (TFA) or hydrogen fluoride (HF).

The linker may then be coupled to form a conjugate by reacting the free amino group of the $Trp^8$ residue of the GRP receptor targeting peptide with an appropriate functional group of the linker. The entire construct of chelator, linker and targeting moiety discussed above may also be assembled on resin and then cleaved by agency of suitable reagents such as trifluoroacetic acid or HF, as well.

4. Labeling and Administration of Compounds

Incorporation of the metal within the conjugate can be achieved by various methods commonly known in the art of coordination chemistry. When the metal is $^{99m}Tc$, a preferred radionuclide for diagnostic imaging, the following general procedure can be used to form a technetium complex. A peptide-chelator conjugate solution is formed by initially dissolving the conjugate in water, dilute acid, or in an aqueous solution of an alcohol such as ethanol. The solution is then optionally degassed to remove dissolved oxygen. When an -SH group is present in the peptide, a thiol protecting group such as Acm (acetamidomethyl), trityl or other thiol protecting group may optionally be used to protect the thiol from oxidation. The thiol protecting group(s) are removed with a suitable reagent, for example with sodium hydroxide, and are then neutralized with an organic acid such as acetic acid (pH 6.0–6.5). Alternatively, the thiol protecting group can be removed in situ during technetium chelation. In the labeling step, sodium pertechnetate obtained from a molybdenum generator is added to a solution of the conjugate with a sufficient amount of a reducing agent, such as stannous chloride, to reduce technetium and is either allowed to stand at room temperature or is heated. The labeled conjugate can be separated from the contaminants $^{99m}TcO_4^-$ and colloidal $^{99m}TcO_2$ chromatographically, for example with a C-18 Sep Pak cartridge [Millipore Corporation, Waters Chromatography Division, 34 Maple Street, Milford, Mass. 01757] or by HPLC using methods known to those skilled in the art.

In an alternative method, the labeling can be accomplished by a transchelation reaction. In this method, the technetium source is a solution of technetium that is reduced and complexed with labile ligands prior to reaction with the selected chelator, thus facilitating ligand exchange with the selected chelator. Examples of suitable ligands for transchelation includes tartrate, citrate, gluconate, and heptagluconate. It will be appreciated that the conjugate can be labeled using the techniques described above, or alternatively, the chelator itself may be labeled and subsequently coupled to the peptide to form the conjugate; a process referred to as the "prelabeled chelate" method. Re and Tc are both in row VIIB of the Periodic Table and they are chemical congeners. Thus, for the most part, the complexation chemistry of these two metals with ligand frameworks that exhibit high in vitro and in vivo stabilities are the same [Eckelman, 1995] and similar chelators and procedures can be used to label with Re. Many $^{99m}Tc$ or $^{186/188}Re$ complexes, which are employed to form stable radiometal complexes with peptides and proteins, chelate these metals in their +5 oxidation state [Lister-James et al., 1997]. This oxidation state makes it possible to selectively place $^{99m}Tc$- or $^{186/188}Re$ into ligand frameworks already conjugated to the biomolecule, constructed from a variety of $^{99m}Tc(V)$ and/or $^{186/188}Re(V)$ weak chelates (e.g., $^{99m}Tc$-glucoheptonate, citrate, gluconate, etc.) [Eckelman, 1995; Lister-James et al., 1997; Pollak et al., 1996].

5. Diagnostic and Therapeutic Uses

When labeled with diagnostically and/or therapeutically useful metals, compounds of the present invention can be used to treat and/or detect cancers, including tumors, by procedures established in the art of radiodiagnostics and radiotherapeutics. [Bushbaum, 1995; Fischman et al., 1993; Schubiger et al., 1996; Lowbertz et al., 1994; Krenning et al., 1994].

The compounds of the invention, which, as explained in more detail in the Examples, show higher uptake in tumors in vivo than compounds without the novel linkers disclosed herein, exhibit an improved ability to target GRP receptor-expressing tumors and thus to image or deliver radiotherapy to these tissues. Indeed, as shown in the Examples, radiotherapy is more effective (and survival time increased) using compounds of the invention.

The diagnostic application of these compounds can be as a first line diagnostic screen for the presence of neoplastic cells using scintigraphic imaging, as an agent for targeting neoplastic tissue using hand-held radiation detection instrumentation in the field of radioimmuno guided surgery (RIGS), as a means to obtain dosimetry data prior to administration of the matched pair radiotherapeutic compound, and as a means to assess GRP receptor population as a function of treatment over time.

The therapeutic application of these compounds can be defined either as an agent that will be used as a first line therapy in the treatment of cancer, as combination therapy where these radiolabeled agents could be utilized in conjunction with adjuvant chemotherapy, and as the matched pair therapeutic agent. The matched pair concept refers to a single unmetallated compound which can serve as both a diagnostic and a therapeutic agent depending on the radiometal that has been selected for binding to the appropriate chelate. If the chelator cannot accommodate the desired metals appropriate substitutions can be made to accommodaste the different metal whilst maintaining the pharmacology such that the behaviour of the diagnostic compound in vivo can be used to predict the behaviour of the radiotherapeutic compound.

A conjugate labeled with a radionuclide metal, such as $^{99m}$Tc, can be administered to a mammal, including human patients or subjects, by intravenous, subcutaneous or intraperitoneal injection in a pharmaceutically acceptable carrier and/or solution such as salt solutions like isotonic saline. Radiolabeled scintigraphic imaging agents provided by the present invention are provided having a suitable amount of radioactivity. In forming $^{99m}$Tc radioactive complexes, it is generally preferred to form radioactive complexes in solutions containing radioactivity at concentrations of from about 0.01 millicurie (mCi) to 100 mCi per mL. Generally, the unit dose to be administered has a radioactivity of about 0.01 mCi to about 100 mCi, preferably 1 mCi to 30 mCi. The solution to be injected at unit dosage is from about 0.01 mL to about 10 mL. The amount of labeled conjugate appropriate for administration is dependent upon the distribution profile of the chosen conjugate in the sense that a rapidly cleared conjugate may need to be administered in higher doses than one that clears less rapidly. In vivo distribution and localization can be tracked by standard scintigraphic techniques at an appropriate time subsequent to administration; typically between thirty minutes and 180 minutes depending upon the rate of accumulation at the target site with respect to the rate of clearance at non-target tissue. For example, after injection of the diagnostic radionuclide-labeled compounds of the invention into the patient, a gamma camera calibrated for the gamma ray energy of the nuclide incorporated in the imaging agent can be used to image areas of uptake of the agent and quantify the amount of radioactivity present in the site. Imaging of the site in vivo can take place in a few minutes. However, imaging can take place, if desired, hours or even longer, after the radiolabeled peptide is injected into a patient. In most instances, a sufficient amount of the administered dose will accumulate in the area to be imaged within about 0.1 hour to permit the taking of scintiphotos.

The compounds of the present invention can be administered to a patient alone or as part of a composition that contains other components such as excipients, diluents, radical scavengers, stabilizers, and carriers, all of which are well-known in the art. The compounds can be administered to patients either intravenously or intraperitoneally.

There are numerous advantages associated with the present invention. The compounds made in accordance with the present invention form stable, well-defined $^{99m}$Tc or $^{186/188}$Re labeled compounds. Similar compounds of the invention can also be made by using appropriate chelator frameworks for the respective radiometals, to form stable, well-defined products labeled with $^{153}$Sm, $^{90}$Y, $^{166}$Ho, $^{105}$Rh, $^{199}$Au, $^{149}$Pm, $^{177}$Lu, $^{111}$In or other radiometal. The radiolabeled GRP receptor targeting peptides selectively bind to neoplastic cells expressing GRP receptors, and if an agonist is used, become internalized, and are retained in the tumor cells for extended time periods. The radioactive material that does not reach (i.e., does not bind) the cancer cells is preferentially excreted efficiently into the urine with minimal retention of the radiometal in the kidneys.

6. Radiotherapy

Radioisotope therapy involves the administration of a radiolabeled compound in sufficient quantity to damage or destroy the targeted tissue. After administration of the compound (by e.g., intravenous, subcutaneous, or intraperitonal injection), the radiolabeled pharmaceutical localizes preferentially at the disease site (in this instance, tumor tissue that expresses the GRP receptor). Once localized, the radiolabeled compound then damages or destroys the diseased tissue with the energy that is released during the radioactive decay of the isotope that is administered.

The design of a successful radiotherapeutic involves several critical factors:

1. selection of an appropriate targeting group to deliver the radioactivity to the disease site;

2. selection of an appropriate radionuclide that releases sufficient energy to damage that disease site, without substantially damaging adjacent normal tissues; and 3. selection of an appropriate combination of the targeting group and the radionuclide without adversely affecting the ability of this conjugate to localize at the disease site. For radiometals, this often involves a chelating group that coordinates tightly to the radionuclide, combined with a linker that couples said chelate to the targeting group, and that affects the overall biodistribution of the compound to maximize uptake in target tissues and minimize uptake in normal, non-target organs.

The present invention provides radiotherapeutic agents that satisfy all three of the above criteria, through proper selection of targeting group, radionuclide, metal chelate and linker.

Radiotherapeutic agents may contain a chelated 3+ metal ion from the class of elements known as the lanthanides (elements of atomic number 57–71) and their analogs (i.e. $M^{3+}$ metals such as yttrium and indium). Typical radioactive metals in this class include the isotopes 90-Yttrium, 111-Indium, 149-Promethium, 153-Samarium, 166-Dysprosium, 166-Holmium, 175-Ytterbium, and 177-Lutetium. All of these metals (and others in the lanthanide series) have very similar chemistries, in that they remain in the +3 oxidation state, and prefer to chelate to ligands that bear hard (oxygen/nitrogen) donor atoms, as typified by derivatives of the well known chelate DTPA (diethylenetriaminepentaacetic acid) and polyaza-polycarboxylate macrocycles such as DOTA (1,4,7,10-tetrazacyclododecane-N,N',N'',N'''-tetraacetic acid and its close analogs. The structures of these chelating ligands, in their fully deprotonated form are shown below.

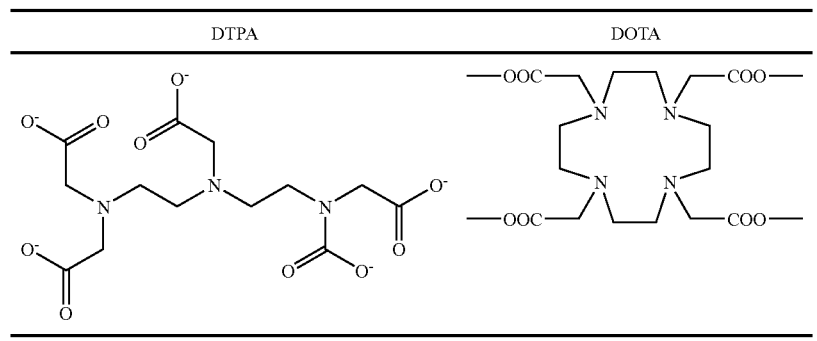

These chelating ligands encapsulate the radiometal by binding to it via multiple nitrogen and oxygen atoms, thus preventing the release of free (unbound) radiometal into the body. This is important, as in vivo dissociation of $3^+$ radiometals from their chelate can result in uptake of the radiometal in the liver, bone and spleen [Brechbiel M W, Gansow O A, "Backbone-substituted DTPA ligands for $^{90}$Y radioimmunotherapy", Bioconj. Chem. 1991; 2: 187–194; Li, W P, Ma D S, Higginbotham C, Hoffman, T, Ketring A R, Cutler C S, Jurisson, S S, "Development of an in vitro model for assessing the in vivo stability of lanthanide chelates." Nucl. Med. Biol. 2001; 28(2): 145–154; Kasokat T, Urich K. Arzneim.-Forsch, "Quantification of dechelation of gadopentetate dimeglumine in rats". 1992; 42(6): 869–76]. Unless one is specifically targeting these organs, such non-specific uptake is highly undesirable, as it leads to non-specific irradiation of non-target tissues, which can lead to such problems as hematopoietic suppression due to irradiation of bone marrow.

For radiotherapy applications any of the chelators for therapeutic radionuclides disclosed herein may be used. However, forms of the DOTA chelate [Tweedle M F, Gaughan G T, Hagan J T, "1-Substituted-1,4,7-triscarboxymethyl-1,4,7,10-tetraazacyclododecane and analogs." U.S. Pat. No. 4,885,363, Dec. 5, 1989] are particularly preferred, as the DOTA chelate is expected to de-chelate less in the body than DTPA or other linear chelates.

General methods for coupling DOTA-type macrocycles to targeting groups through a linker (e.g. by activation of one of the carboxylates of the DOTA to form an active ester, which is then reacted with an amino group on the linker to form a stable amide bond), are known to those skilled in the art. (See e.g. Tweedle et al. U.S. Pat. No. 4,885,363). Coupling can also be performed on DOTA-type macrocycles that are modified on the backbone of the polyaza ring.

The selection of a proper nuclide for use in a particular radiotherapeutic application depends on many factors, including:

a. Physical half-life—This should be long enough to allow synthesis and purification of the radiotherapeutic construct from radiometal and conjugate, and delivery of said construct to the site of injection, without significant radioactive decay prior to injection. Preferably, the radionuclide should have a physical half-life between about 0.5 and 8 days.

b. Energy of the emission(s) from the radionuclide—Radionuclides that are particle emitters (such as alpha emitters, beta emitters and Auger electron emitters) are particularly useful, as they emit highly energetic particles that deposit their energy over short distances, thereby producing highly localized damage. Beta emitting radionuclides are particularly preferred, as the energy from beta particle emissions from these isotopes is deposited within 5 to about 150 cell diameters. Radiotherapeutic agents prepared from these nuclides are capable of killing diseased cells that are relatively close to their site of localization, but cannot travel long distances to damage adjacent normal tissue such as bone marrow.

c. Specific activity (i.e. radioactivity per mass of the radionuclide)—Radionuclides that have high specific activity (e.g. generator produced 90-Y, 111-In, 177-Lu) are particularly preferred. The specific activity of a radionuclide is determined by its method of production, the particular target that is used to produce it, and the properties of the isotope in question.

Many of the lanthanides and lanthanoids include radioisotopes that have nuclear properties that make them suitable for use as radiotherapeutic agents, as they emit beta particles. Some of these are listed in the table below.

| Isotope | Half-Life (days) | Max b-energy (MeV) | Gamma energy (keV) | Approximate range of b-particle (cell diameters) |
|---|---|---|---|---|
| $^{149}$-Pm | 2.21 | 1.1 | 286 | 60 |
| $^{153}$-Sm | 1.93 | 0.69 | 103 | 30 |
| $^{166}$-Dy | 3.40 | 0.40 | 82.5 | 15 |
| $^{166}$-Ho | 1.12 | 1.8 | 80.6 | 117 |
| $^{175}$-Yb | 4.19 | 0.47 | 396 | 17 |
| $^{177}$-Lu | 6.71 | 0.50 | 208 | 20 |
| $^{90}$-Y | 2.67 | 2.28 | — | 150 |
| $^{111}$-In | 2.810 | Auger electron emitter | 173, 247 | <5 µm |

Pm: Promethium,
Sm: Samarium,
Dy: Dysprosium,
Ho: Holmium,
Yb: Ytterbium,
Lu: Lutetium,
Y: Yttrium, In: Indium Methods for the preparation of radiometals such as beta-emitting lanthanide radioisotopes are known to those skilled in the art, and have been described elsewhere [e.g. Cutler C S, Smith C J, Ehrhardt G J.; Tyler T T, Jurisson S S, Deutsch E. "Current and potential therapeutic uses of lanthanide radioisotopes." Cancer Biother. Radiopharm. 2000; 15(6): 531–545]. Many of these isotopes can be produced in high yield for relatively low cost, and many (e.g. $^{90}$-Y, $^{49}$-Pm, $^{177}$-Lu) can be produced at close to carrier-free specific activities (i.e. the vast majority of atoms are radioactive). Since non-radioactive atoms can compete with their radioactive analogs for binding to receptors on the target tissue, the use of high specific activity radioisotope is important, to allow delivery of as high a dose of radioactivity to the target tissue as possible.

Radiotherapeutic derivatives of the invention containing beta-emitting isotopes of rhenium ($^{186}$-Re and $^{188}$-Re) are also particularly preferred.

7. Dosages and Additives

Proper dose schedules for the radiopharmaceutical compounds of the present invention are known to those skilled in the art. The compounds can be administered using many methods which include, but are not limited to, a single or multiple IV or IP injections, using a quantity of radioactivity that is sufficient to permit imaging or, in the case of radiotherapy, to cause damage or ablation of the targeted GRP-R bearing tissue, but not so much that substantive damage is caused to non-target (normal tissue). The quantity and dose required for scintigraphic imaging is discussed supra. The quantity and dose required for radiotherapy is also different for different constructs, depending on the energy and half-life of the isotope used, the degree of uptake and clearance of the agent from the body and the mass of the tumor. In general, doses can range from a single dose of about 30–50 mCi to a cumulative dose of up to about 3 Curies.

The radiopharmaceutical compositions of the invention can include physiologically acceptable buffers, and can require radiation stabilizers to prevent radiolytic damage to the compound prior to injection. Radiation stabilizers are known to those skilled in the art, and may include, for example, para-aminobenzoic acid, ascorbic acid, gentistic acid and the like.

A single, or multi-vial kit that contains all of the components needed to prepare the radiopharmaceuticals of this invention, other than the radionuclide, is an integral part of this invention.

A single-vial kit preferably contains a chelator/linker/targeting peptide conjugate of the formula M-N-O-P-G, a source of stannous salt (if reduction is required, e.g., when using technetium), or other pharmaceutically acceptable reducing agent, and is appropriately buffered with pharmaceutically acceptable acid or base to adjust the pH to a value of about 3 to about 9. The quantity and type of reducing agent used will depend highly on the nature of the exchange complex to be formed. The proper conditions are well known to those that are skilled in the art. It is preferred that the kit contents be in lyophilized form. Such a single vial kit may optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or α, β, or γ-cyclodextrin that serve to improve the radiochemical purity and stability of the final product. The kit may also contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial may contain all of the ingredients that are required to form a labile Tc(V) complex on addition of pertechnetate (e.g. the stannous source or other reducing agent). Pertechnetate is added to this vial, and after waiting an appropriate period of time, the contents of this vial are added to a second vial that contains the chelator and targeting peptide, as well as buffers appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. may be present in either or both vials.

General Preparation of Compounds

The compounds of the present invention can be prepared by various methods depending upon the selected chelator. The peptide portion of the compound can be most conveniently prepared by techniques generally established and known in the art of peptide synthesis, such as the solid-phase peptide synthesis (SPPS) approach. Because it is amenable to solid phase synthesis, employing alternating FMOC protection and deprotection is the preferred method of making short peptides. Recombinant DNA technology is preferred for producing proteins and long fragments thereof.

Solid-phase peptide synthesis (SPPS) involves the stepwise addition of amino acid residues to a growing peptide chain that is linked to an insoluble support or matrix, such as polystyrene. The C-terminal residue of the peptide is first anchored to a commercially available support with its amino group protected with an N-protecting agent such as a t-butyloxycarbonyl group (Boc) or a fluorenylmethoxycarbonyl (Fmoc) group. The amino protecting group is removed with suitable deprotecting agents such as TFA in the case of Boc or piperidine for Fmoc and the next amino acid residue (in N-protected form) is added with a coupling agent such as diisopropylcarbodiimide (DIC). Upon formation of a peptide bond, the reagents are washed from the support. After addition of the final residue, the peptide is cleaved from the support with a suitable reagent such as trifluoroacetic acid (TFA) or hydrogen fluoride (HF).

Alternative Preparation of the Compounds via Segment Coupling

The compounds of the invention may also be prepared by the process known in the art as segment coupling or fragment condensation (Barlos, K. and Gatos, D.; 2002"Convergent Peptide Synthesis" in *Fmoc Solid Phase Synthesis—A Practical Approach*; Eds. Chan, W. C. and White, P. D.; Oxford University Press, New York; Chap. 9, pp 215–228). In this method segments of the peptide usually in side-chain protected form, are prepared separately by either solution phase synthesis or solid phase synthesis or a combination of the two methods. The choice of segments is crucial and is made using a division strategy that can provide a manageable number of segments whose C-terminal residues and N-terminal residues are projected to provide the cleanest coupling in peptide synthesis. The C-terminal residues of the best segments are either devoid of chiral alpha carbons (glycine or other moieties achiral at the carbon α to the carboxyl group to be activated in the coupling step) or are compromised of amino acids whose propensity to racemization during activation and coupling is lowest of the possible choices. The choice of N-terminal amino acid for each segment is based on the ease of coupling of an activated acyl intermediate to the amino group. Once the division strategy is selected the method of coupling of each of the segments is chosen based on the synthetic accessibility of the required intermediates and the relative ease of manipulation and purification of the resulting products (if needed). The segments are then coupled together, both in solution, or one on solid phase and the other in solution to prepare the final structure in fully or partially protected form.

The protected target compound is then subjected to removal of protecting groups, purified and isolated to give the final desired compound. Advantages of the segment coupling approach are that each segment can be purified separately, allowing the removal of side products such as deletion sequences resulting from incomplete couplings or those derived from reactions such as side-chain amide dehydration during coupling steps, or internal cyclization of side-chains (such as that of Gln) to the alpha amino group during deprotection of Fmoc groups. Such side products would all be present in the final product of a conventional resin-based 'straight through' peptide chain assembly whereas removal of these materials can be performed, if needed, at many stages in a segment coupling strategy. Another important advantage of the segment coupling strategy is that different solvents, reagents and conditions can be applied to optimize the synthesis of each of the segments to high purity and yield resulting in improved purity and yield of the final product. Other advantages realized are decreased consumption of reagents and lower costs.

EXAMPLES

The following examples are provided as examples of different methods which can be used to prepare various compounds of the present invention. Within each example, there are compounds identified in single bold capital letter (e.g., A, B, C), which correlate to the same labeled corresponding compounds in the drawings identified.

General Experimental

A. Definitions of Abbreviations Used

The following common abbreviations are used throughout this specification:
1,1-dimethylethoxycarbonyl (Boc or Boc);
9-fluorenylmethyloxycarbonyl (Fmoc);
1-hydroxybenozotriazole (HOBt);
N,N'-diisopropylcarbodiimide (DIC);
N-methylpyrrolidinone (NMP);
acetic anhydride ($Ac_2O$);
(4,4-dimethyl-2,6-dioxocyclohex-1-ylidene)-3-methylbutyl (iv-Dde);
trifluoroacetic acid (TFA);
Reagent B (TFA:$H_2O$:phenol:triisopropylsilane, 88:5:5:2);
diisopropylethylamine (DIEA);
O-(1H-benzotriazole-1-yl)-N,N,N',N'-tetramethyluronium hexafluorophosphate (HBTU);
O-(7-azabenzotriazol-1-yl)-1,1,3,3-tetramethyluronium hexafluorphosphate (HATU);
N-hydroxysuccinimide (NHS);
solid phase peptide synthesis (SPPS);
dimethylsulfoxide (DMSO);
dichloromethane (DCM);
dimethylformamide (DMF);
dimethylacetamide (DMA);
1,4,7,10-tetraazacyclotetradecane-1,4,7,10-tetraacetic acid (DOTA);
Triisopropylsilane (TIPS);
1,4,7,10-tetraazacyclotetradecane-1,4,7,10-tetraacetic acid (DOTA)
(1R)-1-[1,4,7,10-tetraaza-4,7,10-tris(carboxymethyl)cyclododecyl]ethane-1,2-dicarboxylic acid (CMDOTA);
fetal bovine serum (FBS);
human serum albumin (HSA);
human prostate cancer cell line (PC3);
isobutychloroformate (IBCF);
tributylamine (TBA);
radiochemical purity (RCP); and
high performance liquid chromatography (HPLC).

B. Materials

The Fmoc-protected amino acids used were purchased from Nova-Biochem (San Diego, Calif., USA), Advanced Chem Tech (Louisville, Ky., USA), Chem-Impex International (Wood Dale Ill., USA), and Multiple Peptide Systems (San Diego, Calif., USA). Other chemicals, reagents and adsorbents required for the syntheses were procured from Aldrich Chemical Co. (Milwaukee, Wis., USA) and VWR Scientific Products (Bridgeport, N.J., USA). Solvents for peptide synthesis were obtained from Pharmco Co. (Brookfield Conn., USA). Columns for HPLC analysis and purification were obtained from Waters Co. (Milford, Mass., USA). Experimental details are given below for those that were not commercially available.

C. Instrumentation for Peptide Synthesis

Peptides were prepared using an Advanced ChemTech 496 Ω□ MOS synthesizer, an Advanced ChemTech 357 FBS synthesizer and/or by manual peptide synthesis. However the protocols for iterative deprotection and chain extension employed were the same for all.

D. Instrumentation Employed for Analysis and Purification

Analytical HPLC was performed using a Shimadzu-LC-10A dual pump gradient analytical LC system employing Shimadzu-ClassVP software version 4.1 for system control, data acquisition, and post run processing. Mass spectra were acquired on a Hewlett-Packard Series 1100 MSD mass spectrometer interfaced with a Hewlett-Packard Series 1100 dual pump gradient HPLC system fitted with an Agilent Technologies 1100 series autosampler fitted for either direct flow injection or injection onto a Waters Associates XTerra MS C18 column (4.6 mm×50 mm, 5µ particle, 120 Å pore). The instrument was driven by a HP Kayak workstation using 'MSD Anyone' software for sample submission and HP Chemstation software for instrument control and data acquisition. In most cases the samples were introduced via direct injection using a 5 µL injection of sample solution at a concentration of 1 mg/mL and analyzed using positive ion electrospray to obtain m/e and m/z (multiply charged) ions for confirmation of structure. $^1$H-NMR spectra were obtained on a Varian Innova spectrometer at 500 MHz. $^{13}$C-NMR spectra were obtained on the same instrument at 125.73 MHz. Generally the residual $^1$H absorption, or in the case of $^{13}$C-NMR, the 13C absorption of the solvent employed, was used as an internal reference; in other cases tetramethylsilane (δ=0.00 ppm) was employed. Resonance values are given in δ units. Micro-analysis data was obtained from Quantitative Technologies Inc. Whitehouse N.J. Preparative HPLC was performed on a Shimadzu-LC-8A dual pump gradient preparative HPLC system employing Shimadzu-ClassVP software version 4.3 for system control, data acquisition, fraction collection and post run processing E. General Procedure for Peptide Synthesis:

Rink Amide-Novagel HL resin (0.6 mmol/g) was used as the solid support.

F. Coupling Procedure:

In a typical experiment, the first amino acid was loaded onto 0.1 g of the resin (0.06 mmol). The appropriate Fmoc-amino acid in NMP (0.25M solution; 0.960 mL was added to the resin followed by N-hydroxybenzotriazole (0.5M in NMP; 0.48 mL)) and the reaction block (in the case of automated peptide synthesis) or individual reaction vessel (in the case of manual peptide synthesis) was shaken for about 2 min. To the above mixture, diisopropylcarbodiimide (0.5M in NMP; 0.48 mL) was added and the reaction mixture was shaken for 4 h at ambient temperature. Then the reaction block or the individual reaction vessel was purged of reactants by application of a positive pressure of dry nitrogen.

G. Washing Procedure:

Each well of the reaction block was filled with 1.2 mL of NMP and the block was shaken for 5 min. The solution was drained under positive pressure of nitrogen. This procedure was repeated three times. The same procedure was used, with an appropriate volume of NMP, in the case of manual synthesis using individual vessels.

H. Removal of Fmoc Group:

The resin containing the Fmoc-protected amino acid was treated with 1.5 mL of 20% piperidine in DMF (v/v) and the reaction block or individual manual synthesis vessel was shaken for 15 min. The solution was drained from the resin. This procedure was repeated once and the resin was washed employing the washing procedure described above.

I. Final Coupling of Ligand (DOTA and CMDOTA):

The N-terminal amino group of the resin bound peptide linker construct was deblocked and the resin was washed. A 0.25M solution of the desired ligand and HBTU in NMP was made, and was treated with a two-fold equivalency of DIEA. The resulting solution of activated ligand was added to the the resin (1.972 mL; 0.48 mmol) and the reaction mixture was shaken at ambient temperature for 24–30 h. The solution was drained and the resin was washed. The final wash of the resin was conducted with 1.5 mL dichloromethane (3×).

J. Deprotection and Purification of the Final Peptide:

A solution of reagent B (2 mL; 88:5:5:2—TFA:Phenol:Water:TIPS) was added to the resin and the reaction block or individual vessel was shaken for 4.5 h at ambient temperature. The resulting solution containing the deprotected peptide was drained into a vial. This procedure was repeated two more times with 1 mL of reagent B. The combined filtrate was concentrated under reduced pressure using a Genevac HT-12 series II centrifugal concentrator. The residue in each vial was then triturated with 2 mL of $Et_2O$ and the supernatant was decanted. This procedure was repeated twice to provide the peptides as colorless solids. The crude peptides were dissolved in water/acetonitrile and purified using either a Waters XTerra MS C18 preparative HPLC column (50 mm×19 mm, 5 micron particle size, 120 Å pore size) or a Waters-YMC C18 ODS column (250 mm×30 mm i.d., 10 micron particle size. 120 Å pore size). The fractions with the products were collected and analyzed by HPLC. The fractions with >95% purity were pooled and the peptides isolated by lyophilization.

Conditions for Preparative HPLC (Waters XTerra Column):

Elution rate: 50 mL/min

Detection: UV, $\lambda$=220 nm

Eluent A: 0.1% aq. TFA; Solvent B: Acetonitrile (0.1% TFA). Conditions for HPLC Analysis:

Column: Waters XTerra (Waters Co.; 4.6×50 mm; MS C18; 5 micron particle, 120 Å pore).

Elution rate: 3 mL/min; Detection: UV, $\lambda$=220 nm.

Eluent A: 0.1% aq. TFA; Solvent B: Acetonitrile (0.1% TFA).

Example I

FIGS. 1A–B

Synthesis of L62

Figure 1B:
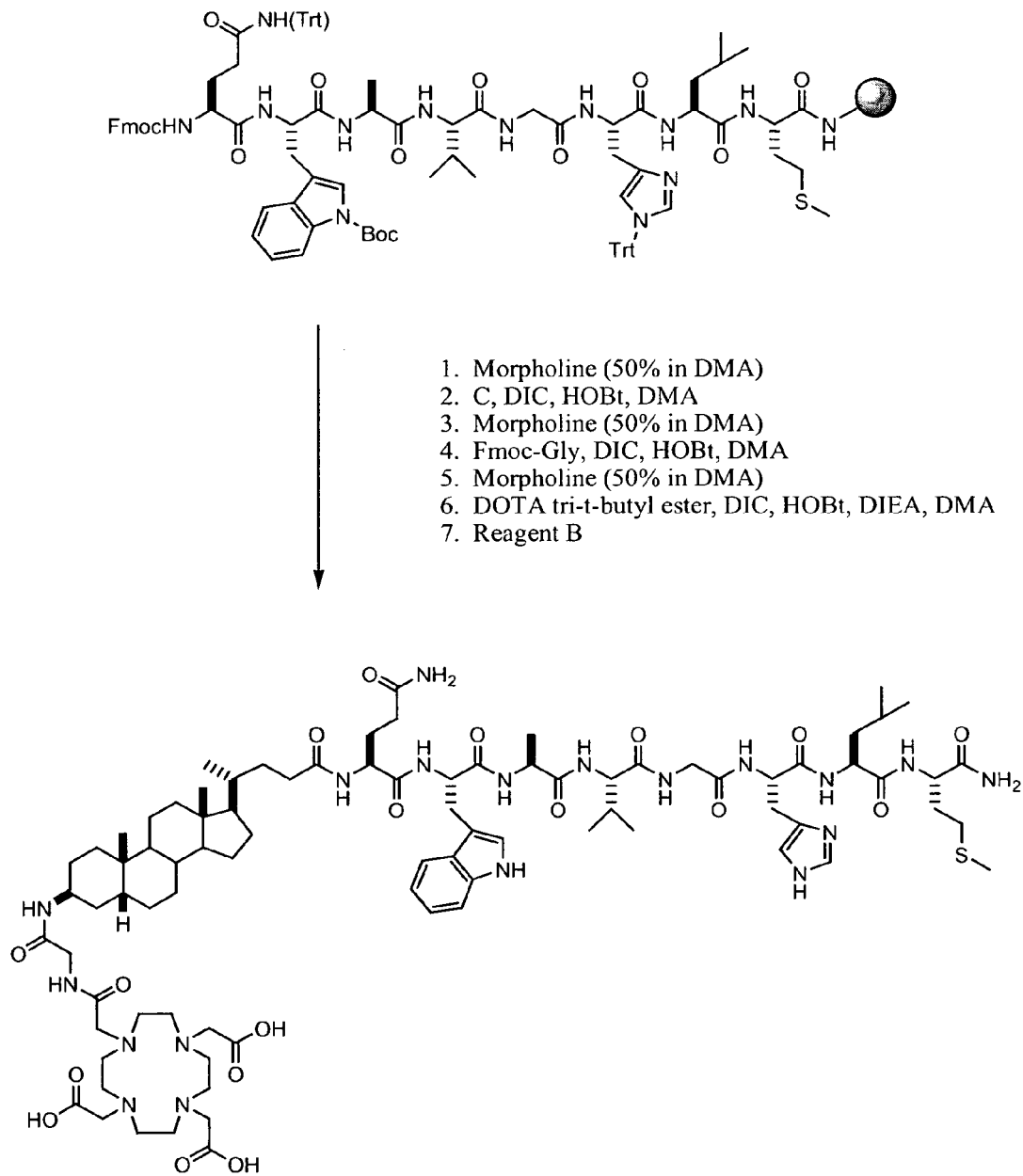
FIG. 1B is a graphical representation of the sequential reaction for the synthesis of N-[(3β,5β)-3-[[[[[4,7,10-Tris (carboxymethyl)-1,4,7,10-tetraazacyclododec-1-yl]acetyl] amino]acetyl]amino]cholan-24-yl]-L-glutaminyl-L-tryptophyl-L-alanyl-L-valyl-glycyl-L-histidyl-L-leucyl-L-methioninamide (L62), as described in Example I.
Figure 2A:
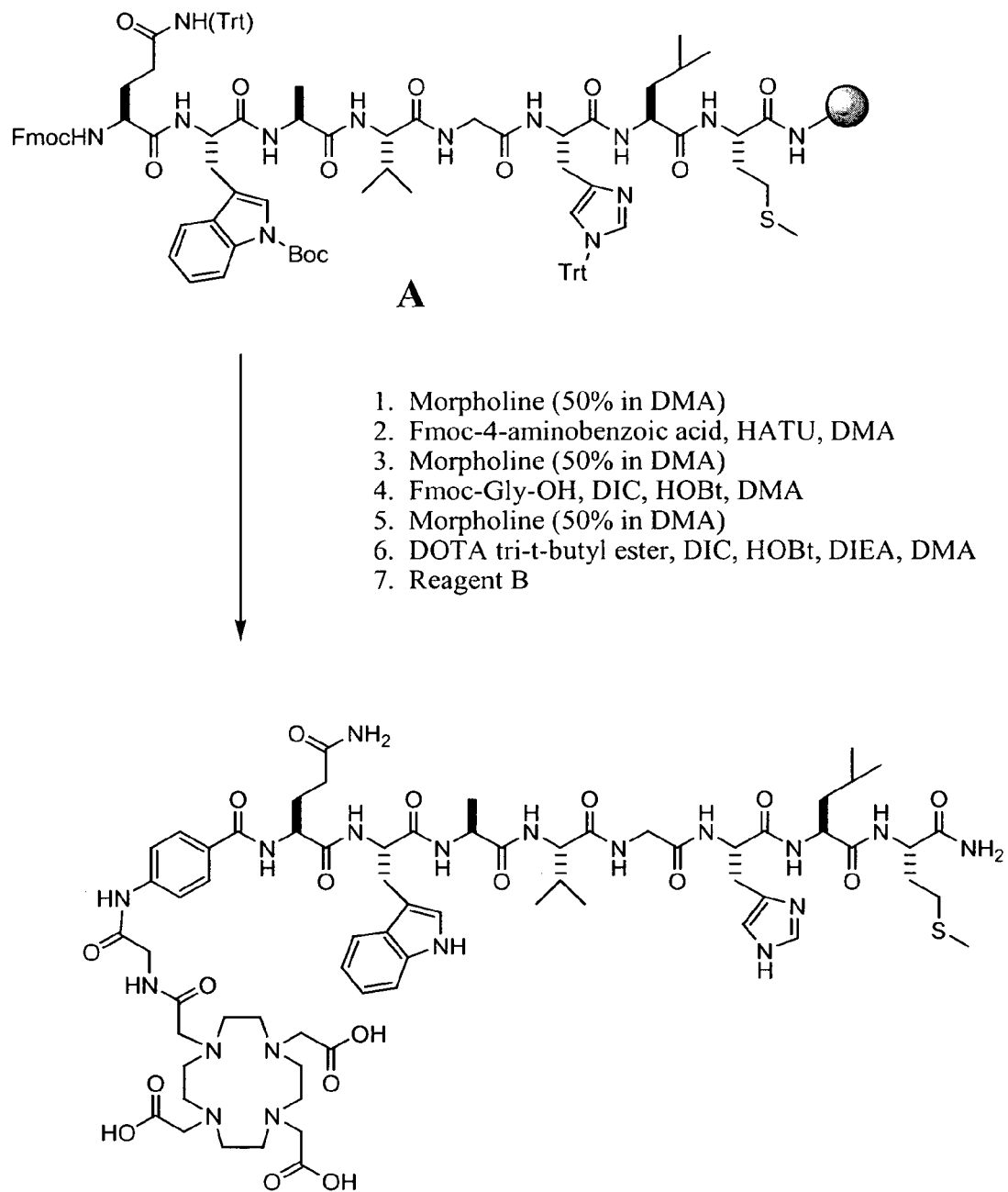
FIG. 2A is a graphical representation of the sequential reaction for the synthesis of N-[4-[[[[[4,7,10-Tris(carboxymethyl)-1,4,7,10-tetraazacyclododec-1-yl]acetyl] amino]acetyl]amino]benzoyl]-L-glutaminyl-L-tryptophyl-L-alanyl-L-valyl-glycyl-L-histidyl-L-leucyl-L-methioninamide (L70), as described in Example II.
Figure 2F:
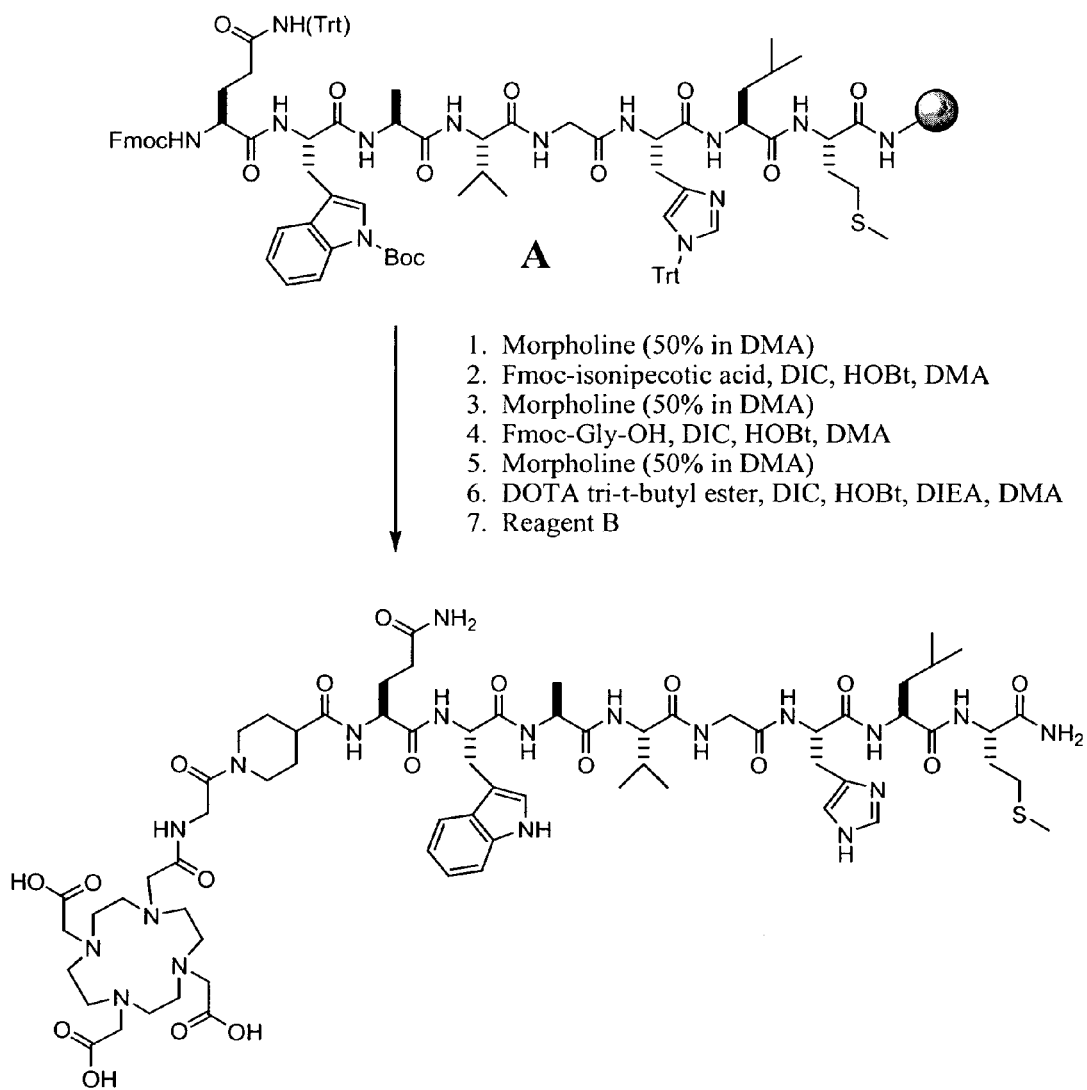
FIG. 2F is a graphical representation of the sequential reaction for the synthesis of N-[[4,7,10-Tris(carboxymethyl)-1,4,7,10-tetraazacyclododec-1-yl]acetyl]glycyl-4-piperidinecarbonyl-L-glutaminyl-L-tryptophyl-L-alanyl-L-valyl-glycyl-L-histidyl-L-leucyl-L-methioninamide (L74), as described in Example II.
Figure 3A:
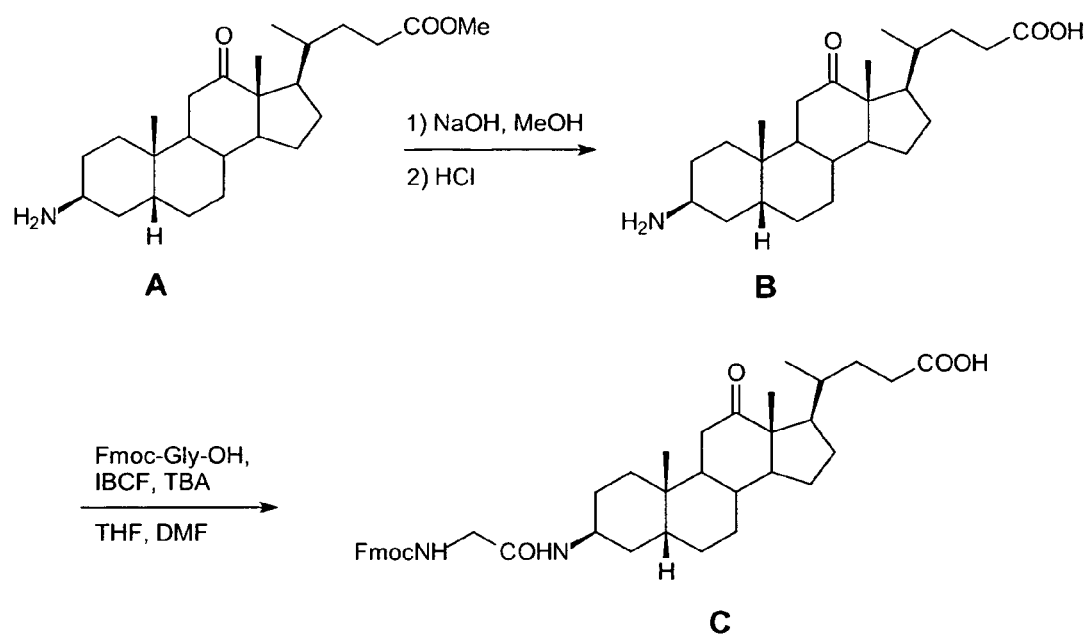
FIG. 3A is a graphical representation of a series of chemical reactions for the synthesis of intermediate (3β,5β)-3-[[[(9H-Fluoren-9-ylmethoxy)amino]acetyl]amino-12-oxo-cholan-24-oic acid (C), as described in Example III.
Figure 3B:
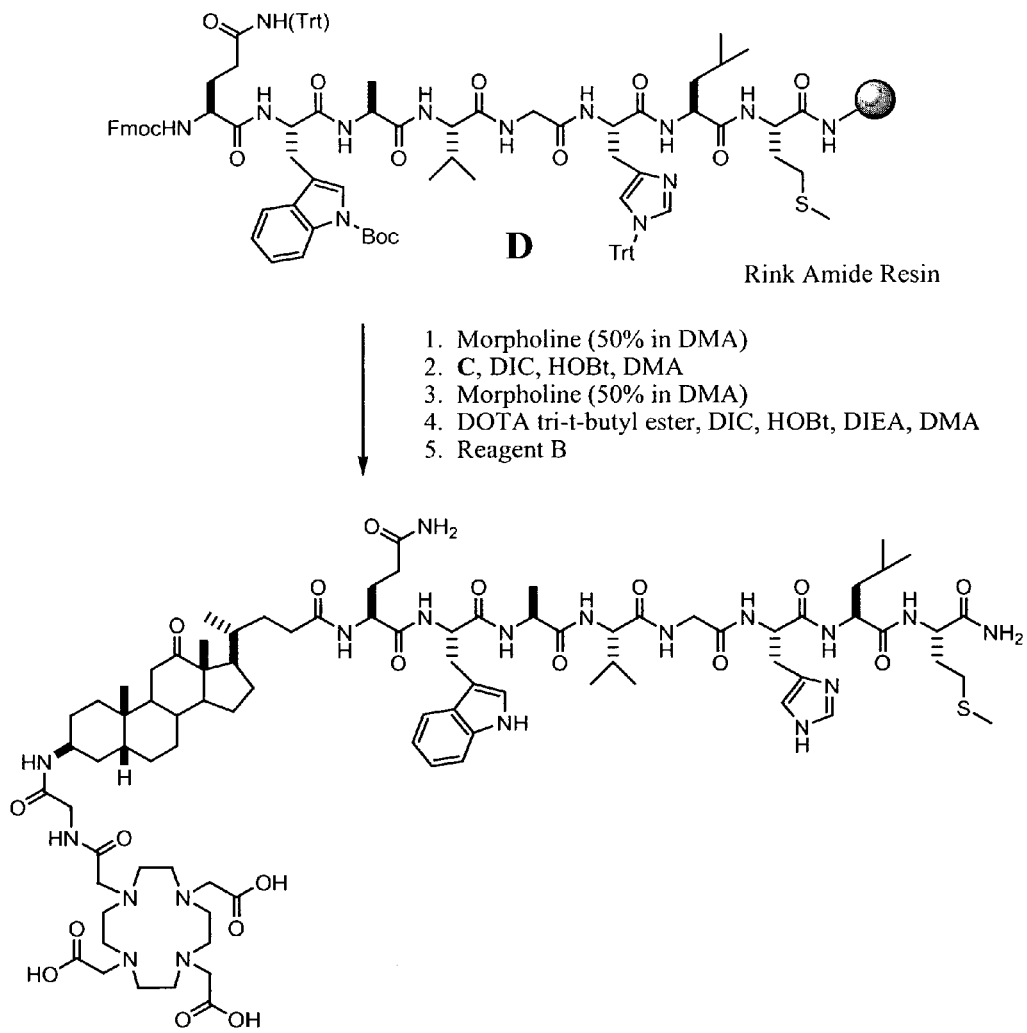
FIG. 3B is a graphical representation of the sequential reaction for the synthesis of N-[(3β,5β)-3-[[[[[4,7,10-Tris (carboxymethyl)-1,4,7,10-tetraazacyclododec-1-yl]acetyl] amino]acetyl]amino]-12,24-dioxocholan-24-yl]-L-glutaminyl-L-tryptophyl-L-alanyl -L-valyl-glycyl-L-histidyl-L-leucyl-L-methioninamide (L67), as described in Example III.
Figure 3C:
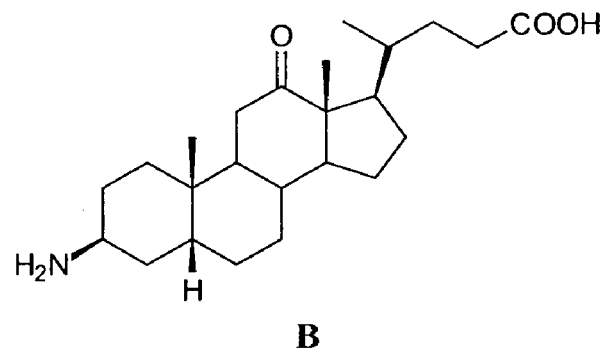
FIG. 3C is a chemical structure of (3β,5β)-3-Amino-12-oxocholan-24-oic acid (B), as described in Example III.
Figure 3D:
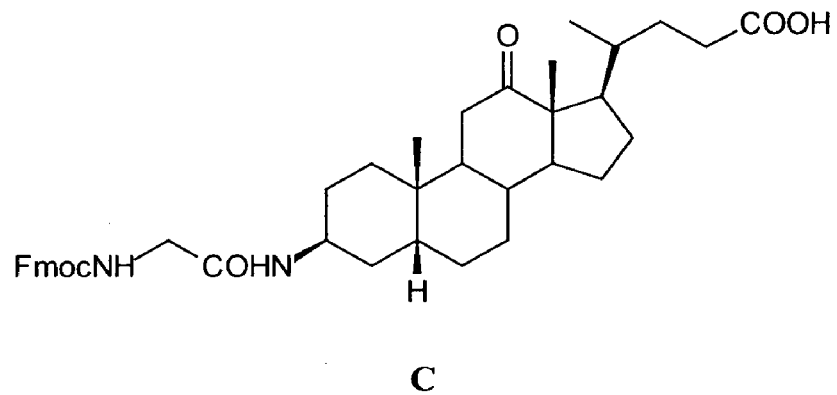
FIG. 3D is a chemical structure of (3β,5β)-3-[[(9H-Fluoren-9-ylmethoxy)amino]acetyl]amino-12-oxocholan-24-oic acid (C), as described in Example III.
Figure 3E:
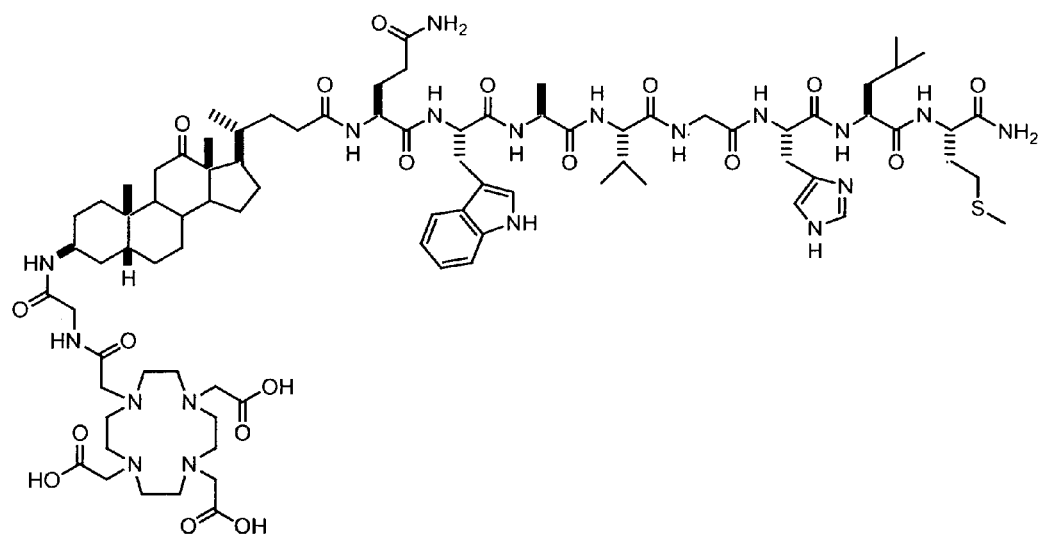
FIG. 3E is a chemical structure of N-[(3β,5β)-3-[[[[4,7,10-Tris(carboxymethyl)-1,4,7,10-tetraazacyclododec-1-yl] acetyl]amino]acetyl]amino]-12,24-dioxocholan-24-yl]-L-glutaminyl-L-tryptophyl-L-alanyl-L-valyl-glycyl-L-histidyl-L-leucyl-L-methioninamide(L67), as described in Example III.
Figure 4A:
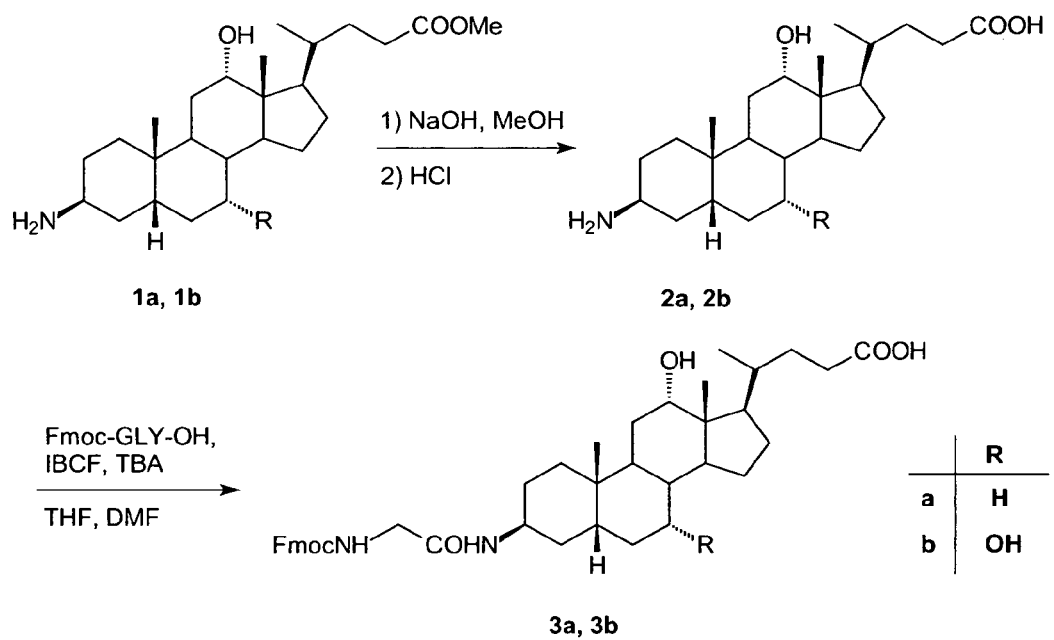
FIG. 4A is a graphical representation of a sequence of reactions to obtain intermediates (3β,5β,12α)-3-[[(9H-Fluoren-9-ylmethoxy)amino]acetyl]amino-12-hydroxy cholan-24-oic acid (3a) and (3β,5β,7α,12α)-3-[[(9H-Fluoren-9-ylmethoxy)amino]acetyl]amino-7,12-dihydroxycholan-24-oic acid (3b), as described in Example IV.
Figure 4B:
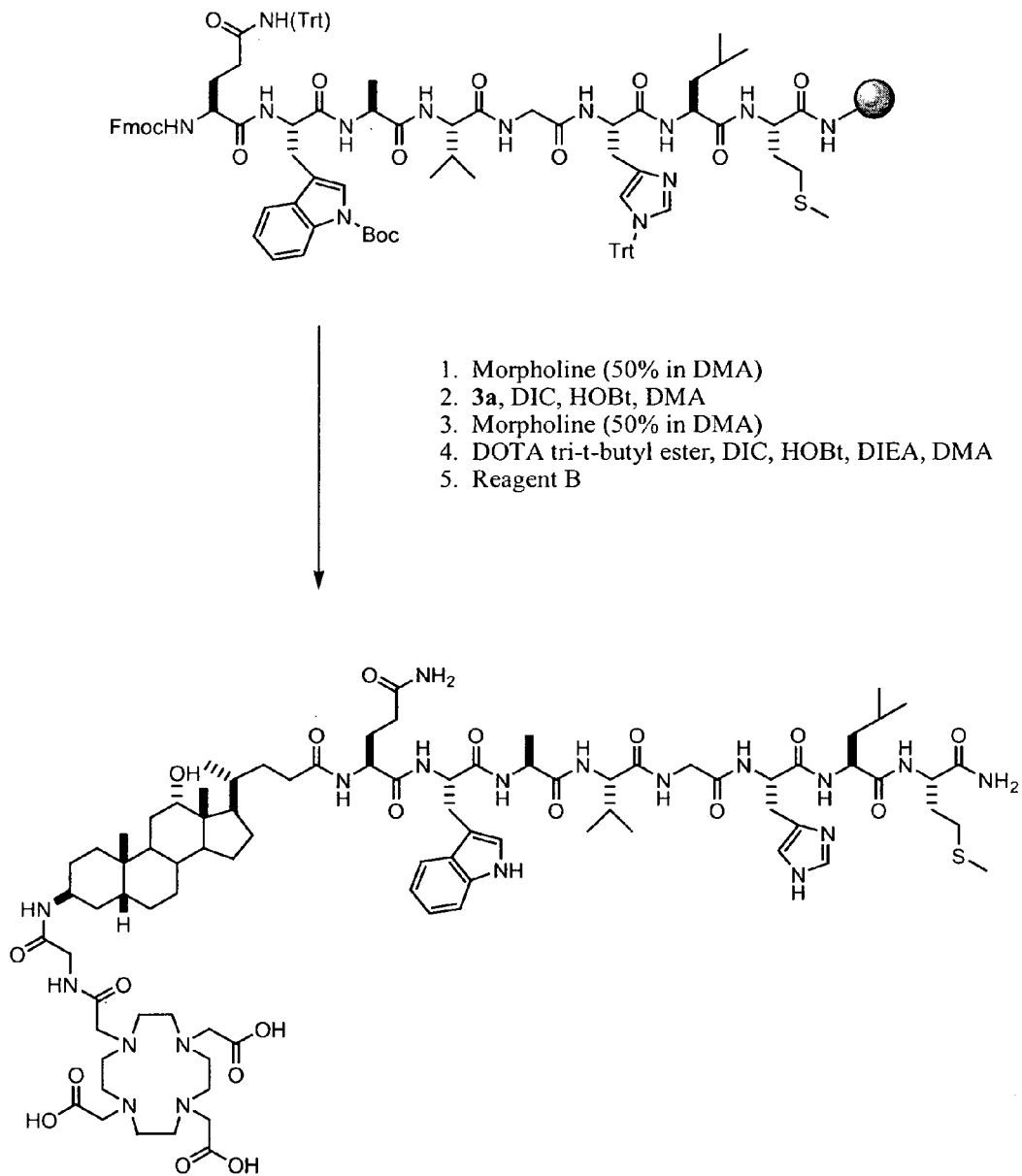
FIG. 4B is a graphical representation of the sequential reaction for the synthesis of N-[(3β,5β,12α)-3-[[[[[4,7,10-Tris(carboxymethyl)-1,4,7,10-tetraazacyclododec-1-yl] acetyl]amino]acetyl]amino]-12-hydroxy-24-oxocholan-24-yl]-L-glutaminyl-L-tryptophyl-L-alanyl-L-valyl-glycyl-L-histidyl-L-leucyl-L-methioninamide (L63), as described in Example IV.
Figure 4C:
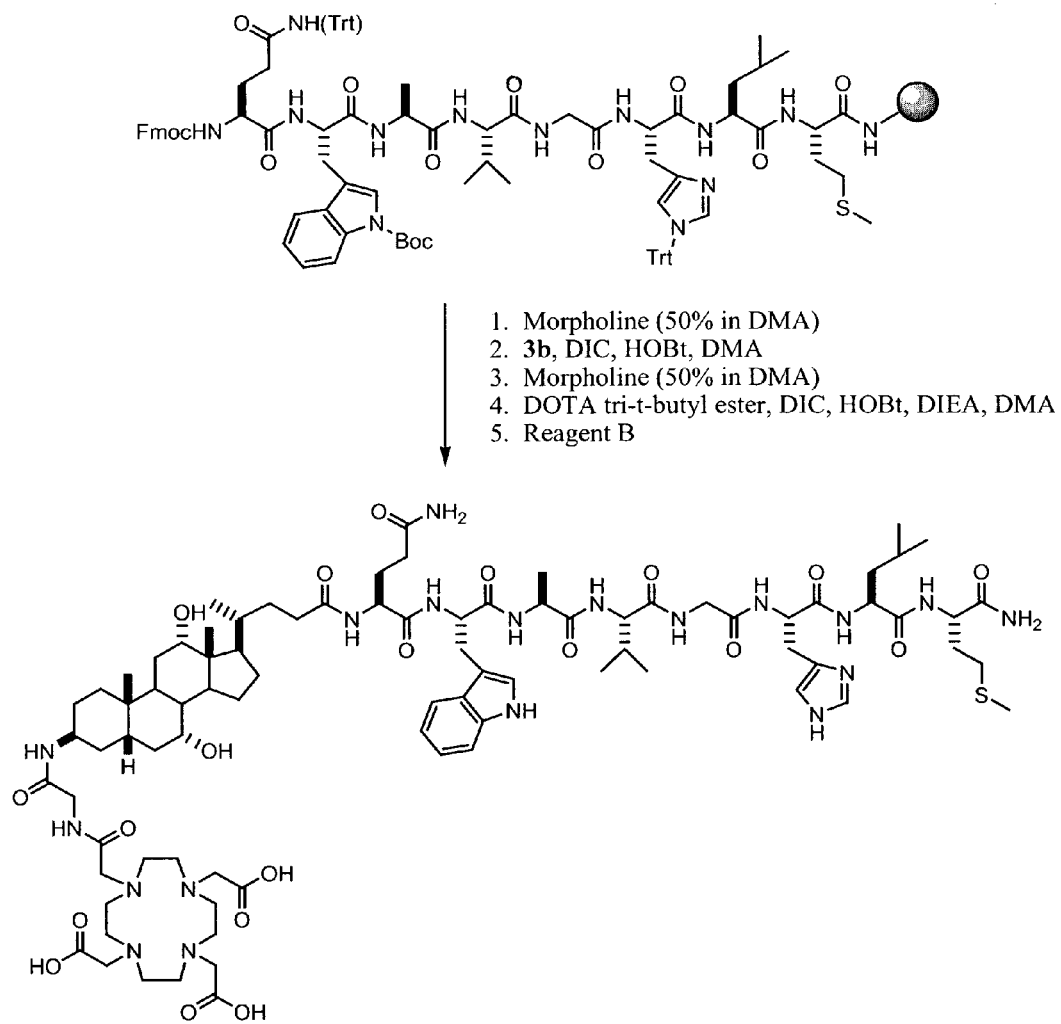
FIG. 4C is a graphical representation of the sequential reaction for the synthesis of N-[(3β,5β,7α,12α)-3-[[[[[4,7,10-Tris(carboxymethyl)-1,4,7,10-tetraazacyclo dodec-1-yl] acetyl]amino]acetyl]amino]-7,12-dihydroxy-24-oxocholan-24-yl]-L-glutaminyl-L-tryptophyl-L-alanyl-L-valyl-glycyl-L-histidyl-L-leucyl-L-methioninamide (L64), as described in Example IV.
Figure 4D:
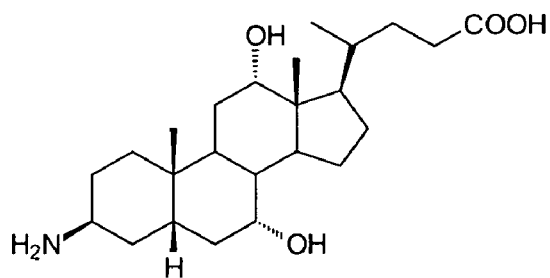
FIG. 4D is a chemical structure of (3β,5β,7α,12α)-3-amino-7,12-dihydroxycholan-24-oic acid (2b), as described in Example IV.
Figure 4E:
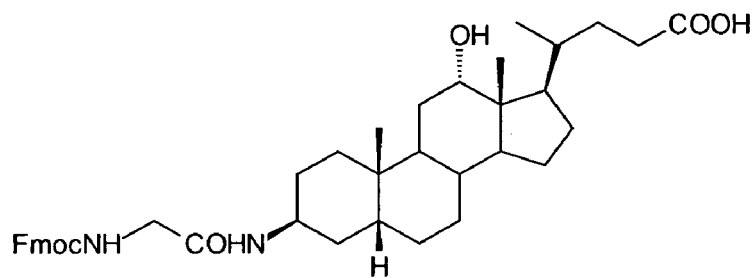
FIG. 4E is a chemical structure of (3β,5β,12α)-3-[[(9H-Fluoren-9-ylmethoxy)amino]acetyl]amino-12-hydroxycholan-24-oic acid (3a), as described in Example IV.
Figure 4F:
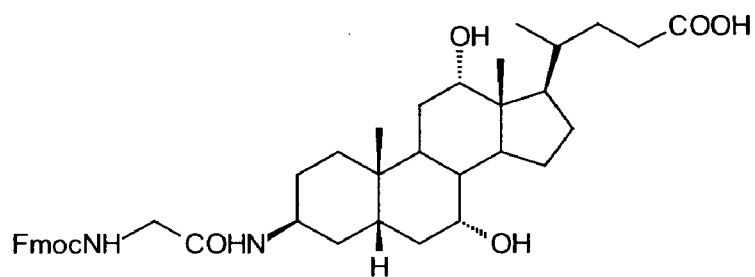
FIG. 4F is a chemical structure of (3β,5β,7α,12α)-3-[[(9H-Fluoren-9-ylmethoxy)amino]acetyl]amino-7,12-dihydroxycholan-24-oic acid (3b), as described in Example IV.
Figure 4G:
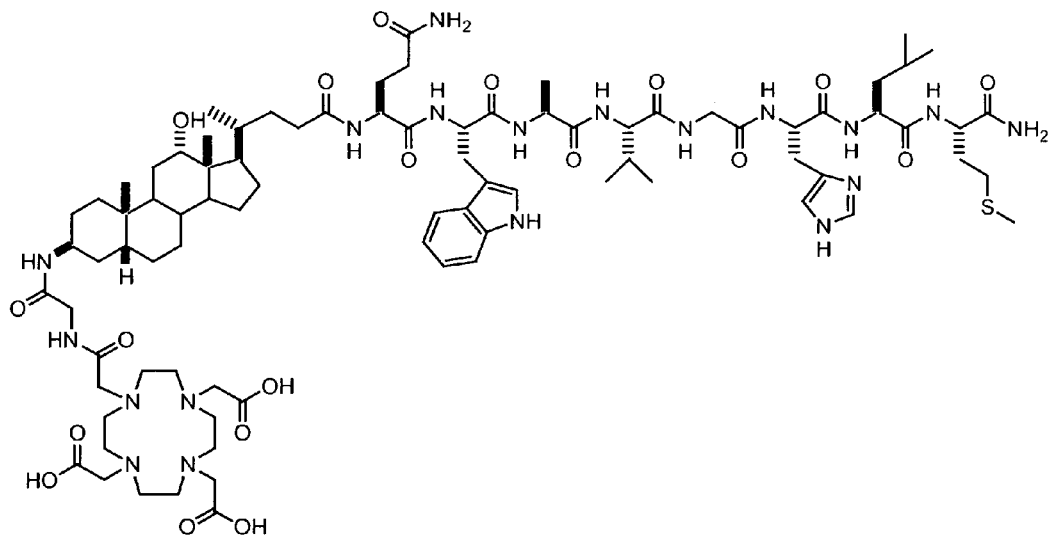
FIG. 4G is a chemical structure of N-[(3β,5β,12α)-3-[[[[[4,7,10-Tris(carboxymethyl)-1,4,7,10-tetraazacyclododec-1-yl]acetyl]amino]acetyl]amino]-12-hydroxy-24-oxocholan-24-yl]-L-glutaminyl-L-tryptophyl-L-alanyl-L-valyl-glycyl-L-histidyl-L-leucyl-L-methioninamide (L63), as described in Example IV.
Figure 4H:
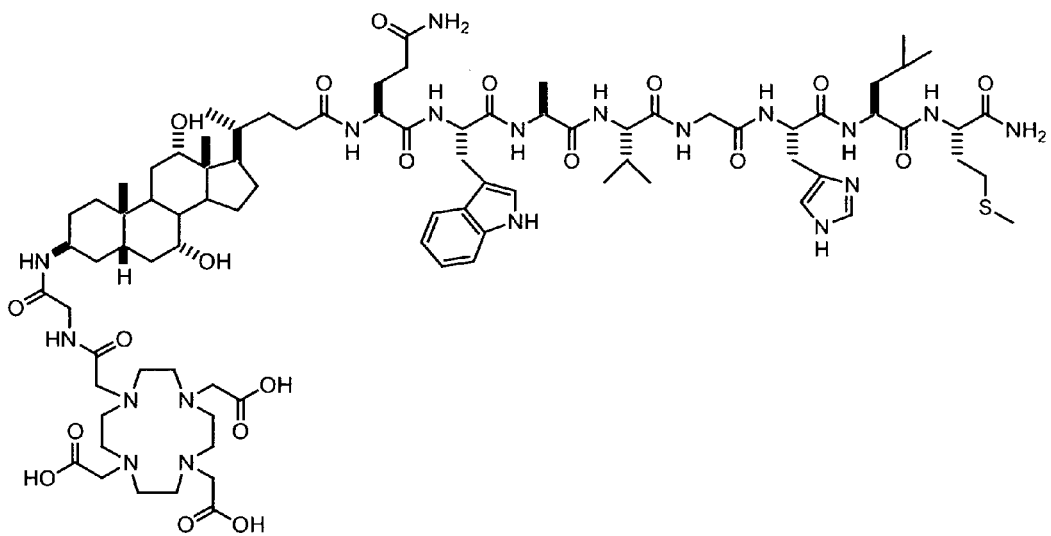
FIG. 4H is a chemical structure of N-[(3β,5β,7α,12α)-3-[[[[[4,7,10-Tris(carboxymethyl)-1,4,7,10-tetraazacyclo dodec-1-yl]acetyl]amino]acetyl]amino]-7,12-dihydroxy-24-oxocholan-24-yl]-L-glutaminyl-L-tryptophyl-L-alanyl-L-valyl-glycyl-L-histidyl-L-leucyl-L-methioninamide (L64), as described in Example IV.
Figure 5A:
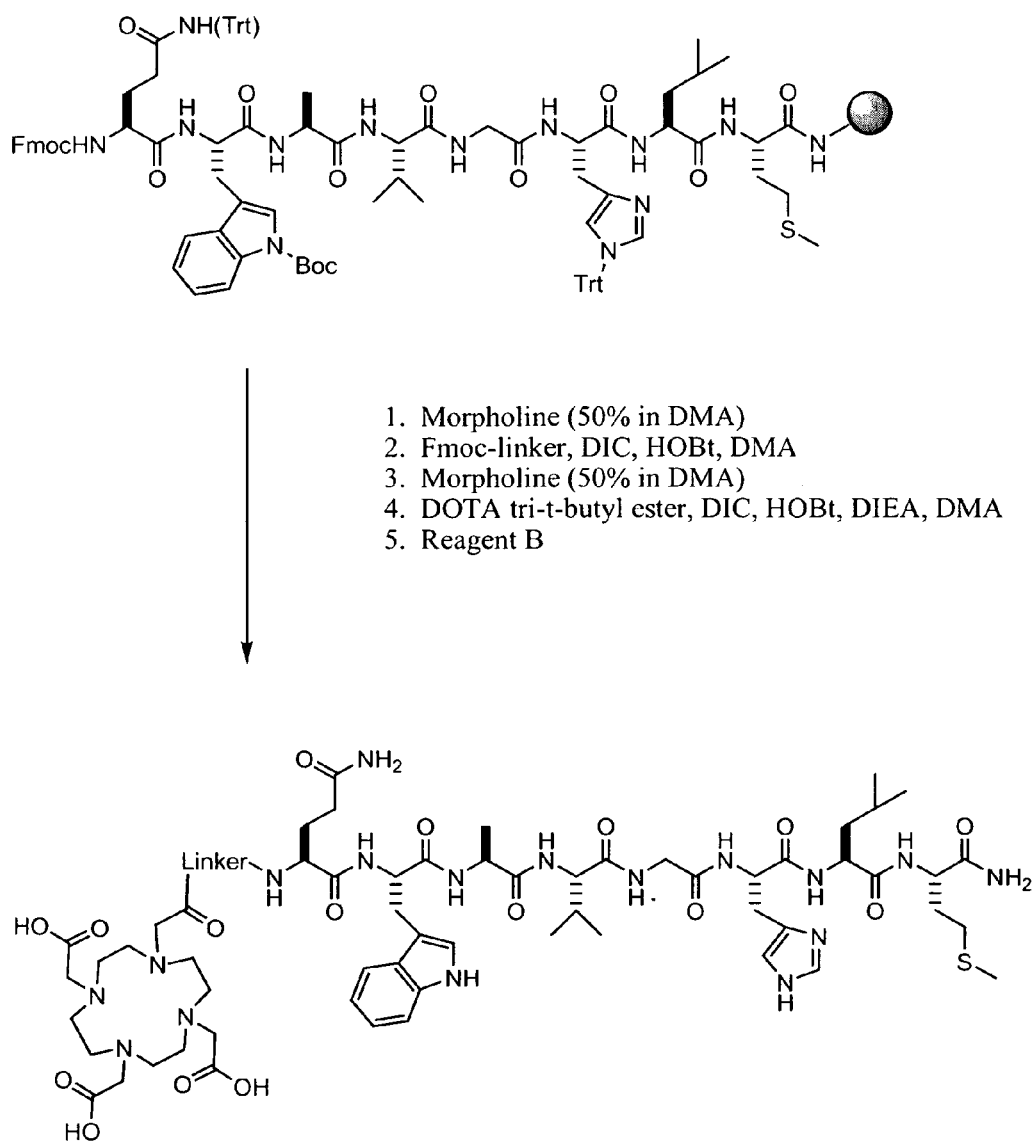
FIG. 5A is a general graphical representation of the sequential reaction for the synthesis of 4-[[[[4,7,10-Tris (carboxymethyl)-1,4,7,10-tetraazacyclododec-1-yl]acetyl] amino]methyl]benzoyl-L-glutaminyl-L-tryptophyl-L-alanyl-L-valyl-glycyl-L-histidyl-L-leucyl-L-methioninamide (L71); and Trans-4-[[[[4,7,10-tris(carboxymethyl)-1,4,7,10-tetraazacyclododec-1-yl]acetyl]amino]methyl]cyclohexyl-carbonyl-L-glutaminyl-L-tryptophyl-L-alanyl-L-valyl-gly-cyl-L-histidyl-L-leucyl-L-methioninamide (L72) as described in Example V.
Figure 5B:
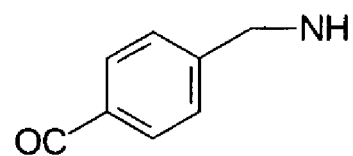
FIG. 5B is a chemical structure of the linker used in compound L71 as shown in FIG. 5A and as described in Example V.
Figure 5C:
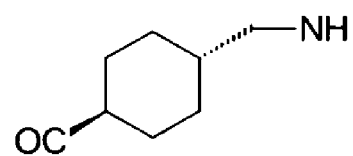
FIG. 5C is a chemical structure of the linker used in compound L72 as shown in FIG. 5B and as described in Example V.
Figure 5D:
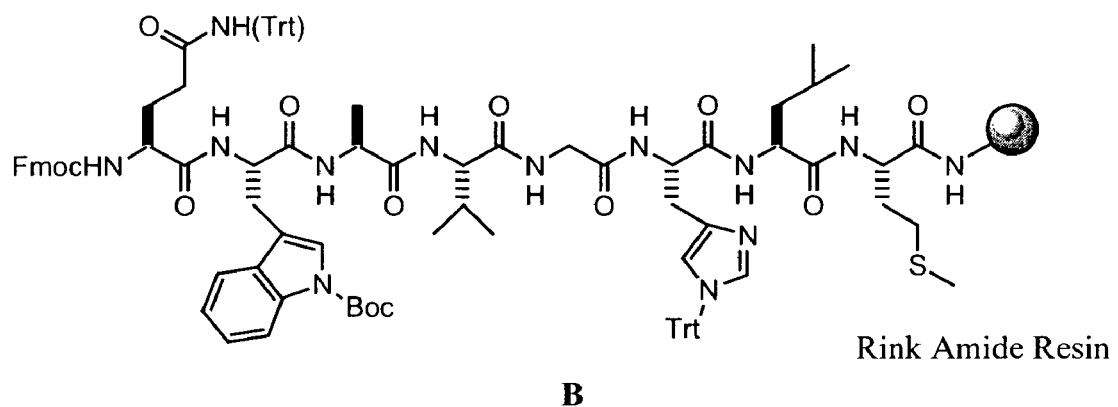
FIG. 5D is a chemical structure of Rink amide resin functionalised with bombesin[7-14] (B), as described in Example V.
Figure 5E:
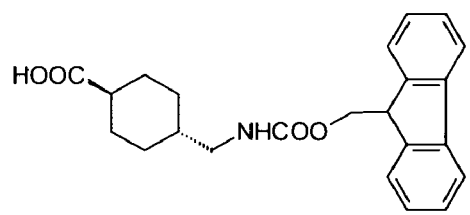
FIG. 5E is a chemical structure of Trans-4-[[[(9H-fluoren-9-ylmethoxy)carbonyl]amino]methyl]cyclohexanecarboxy-lic acid (D), as described in Example V.
Figure 6A:
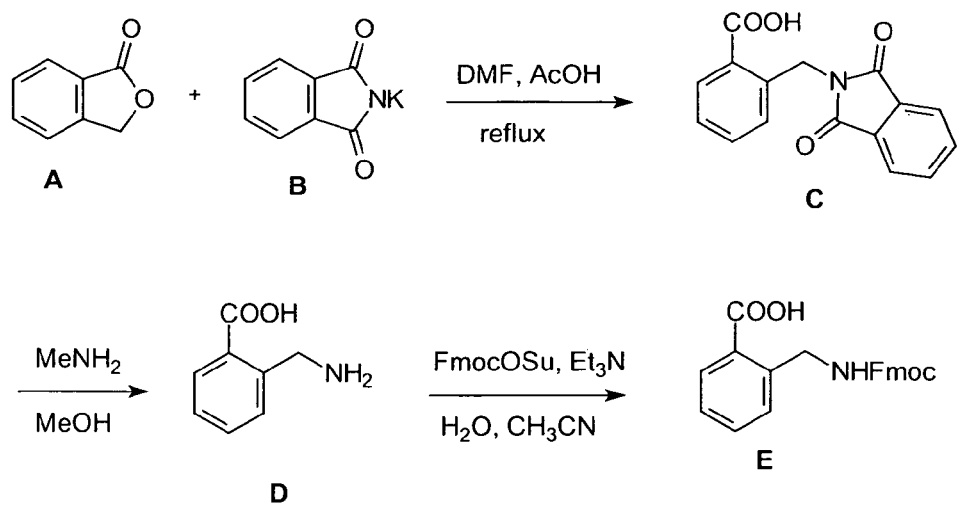
FIG. 6A is a graphical representation of a sequence of reactions for the synthesis of intermediate linker 2-[[[9H-Fluoren-9-ylmethoxy)carbonyl]amino]methyl]benzoic acid (E), as described in Example VI.
Figure 6B:
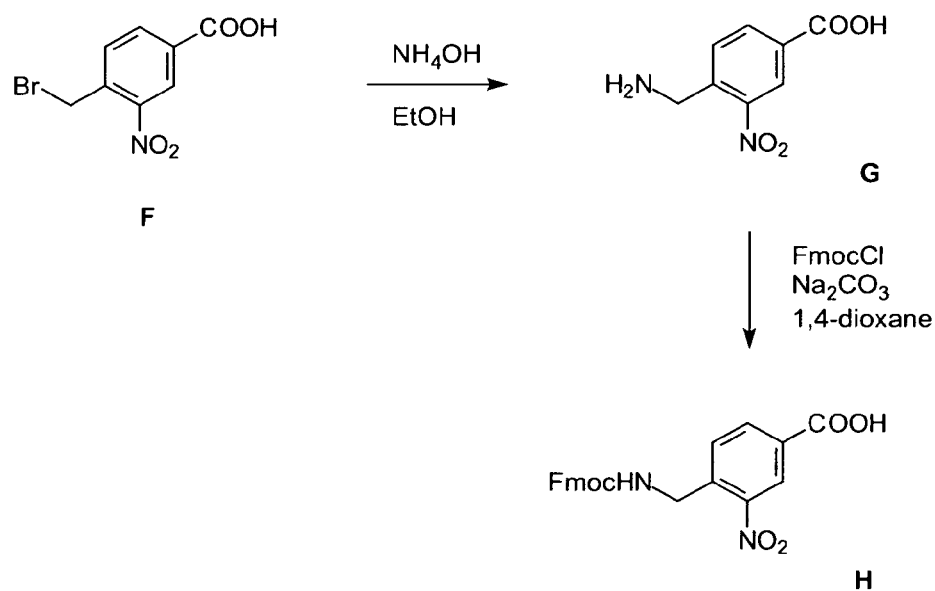
FIG. 6B is a graphical representation of a sequence of reactions for the synthesis of intermediate linker 4-[[[9H-Fluoren-9-ylmethoxy)carbonyl]amino]methyl]-3-nitrobenzoic acid (H), as described in Example VI.
Figure 6C:
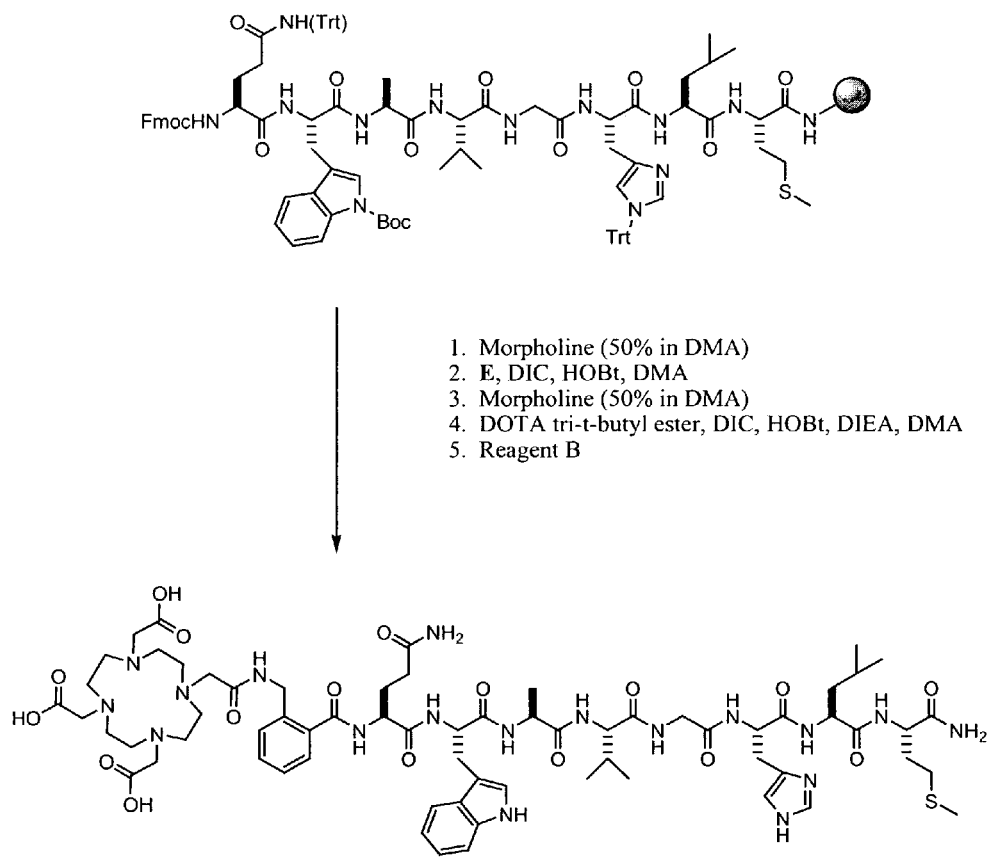
FIG. 6C is a graphical representation of the synthesis of N-[2-[[[[4,7,10-Tris(carboxymethyl)-1,4,7,10-tetraazacyclododec-1-yl]acetyl]amino]methyl]benzoyl]-L-glutaminyl-L-tryptophyl-L-alanyl-L-valyl-glycyl-L-histidyl-L-leucyl-L-methioninamide (L75), as described in Example VI.
Figure 6D:
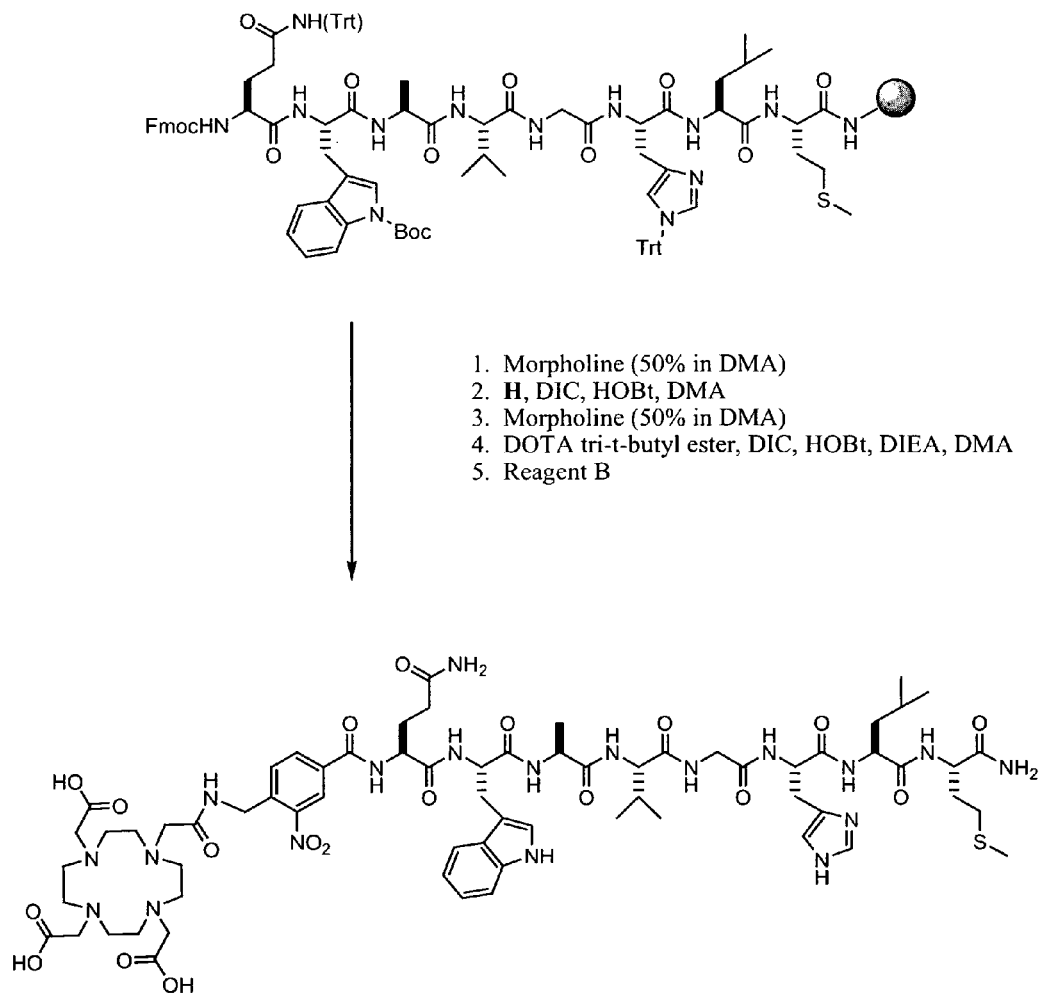
FIG. 6D is a graphical representation of the synthesis of N-[4-[[[[4,7,10-Tris(carboxymethyl)-1,4,7,10-tetraazacyclododec-1-yl]acetyl]amino]methyl]-3-nitrobenzoyl]-L-glutaminyl-L-tryptophyl-L-alanyl-L-valyl-glycyl-L-histi-dyl-L-leucyl-L-methioninamide (L76), as described in Example VI.
Figure 6J:
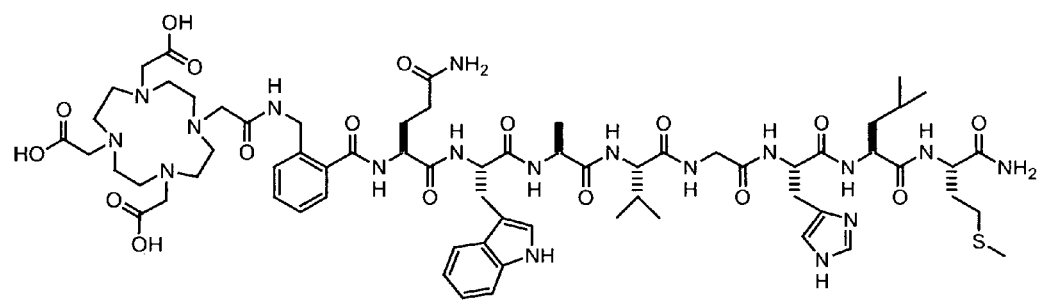
FIG. 6J is a chemical structure of N-[2-[[[[4,7,10-Tris (carboxymethyl)-1,4,7,10-tetraazacyclododec-1-yl]acetyl] amino]methyl]benzoyl]-L-glutaminyl-L-tryptophyl-L-ala-nyl-L-valyl-glycyl-L -histidyl-L-leucyl-L-methioninamide (L75), as described in Example VI.
Figure 6K:
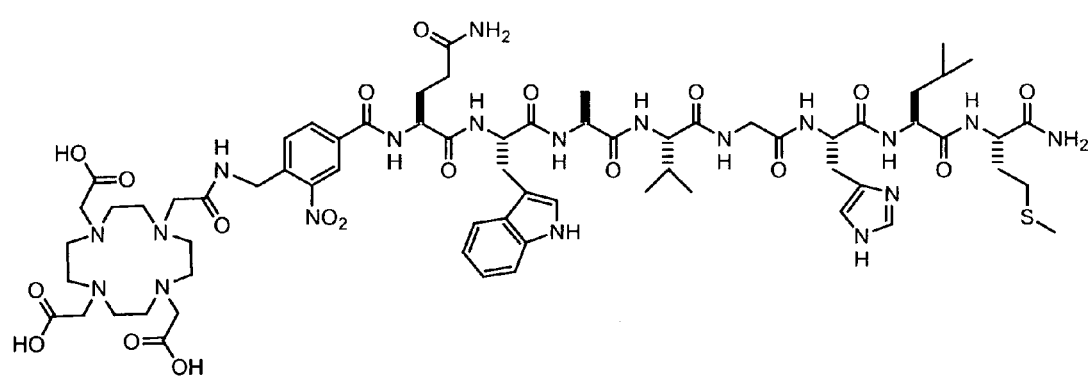
FIG. 6K is a chemical structure of N-[4-[[[[4,7,10-Tris (carboxymethyl)-1,4,7,10-tetraazacyclododec-1-yl]acetyl] amino]methyl]-3-nitrobenzoyl]-L-glutaminyl-L-tryptophyl-L-alanyl-L-valyl-glycyl-L-histidyl-L-leucyl-L-methioninamide (L76), as described in Example VI.
Figure 7A:
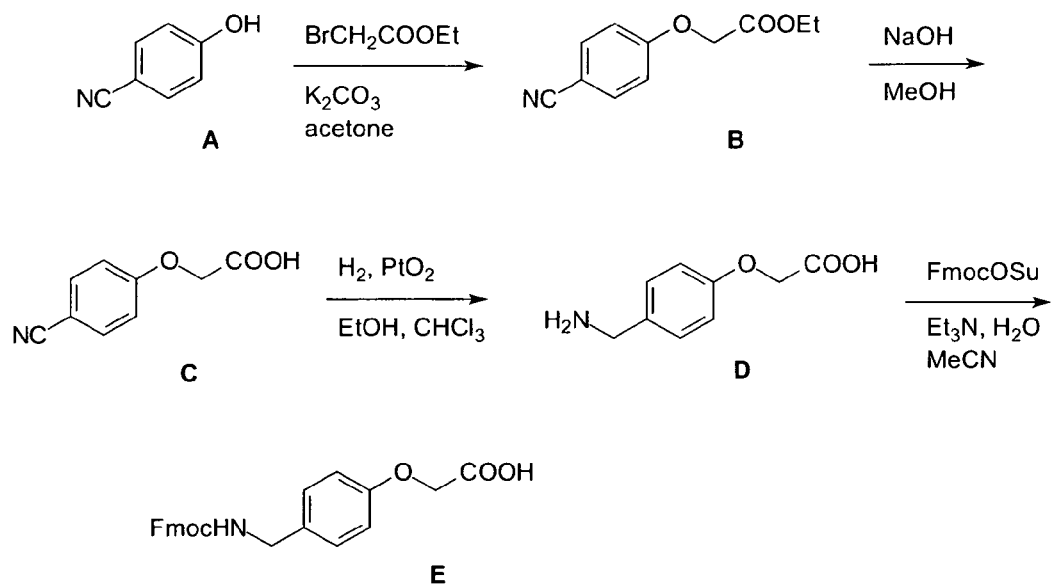
FIG. 7A is a graphical representation of a sequence of reactions for the synthesis of intermediate linker [4-[[[9H-Fluoren-9-ylmethoxy)carbonyl]amino]methyl]phenoxy] acetic acid (E), as described in Example VII.
Figure 7B:
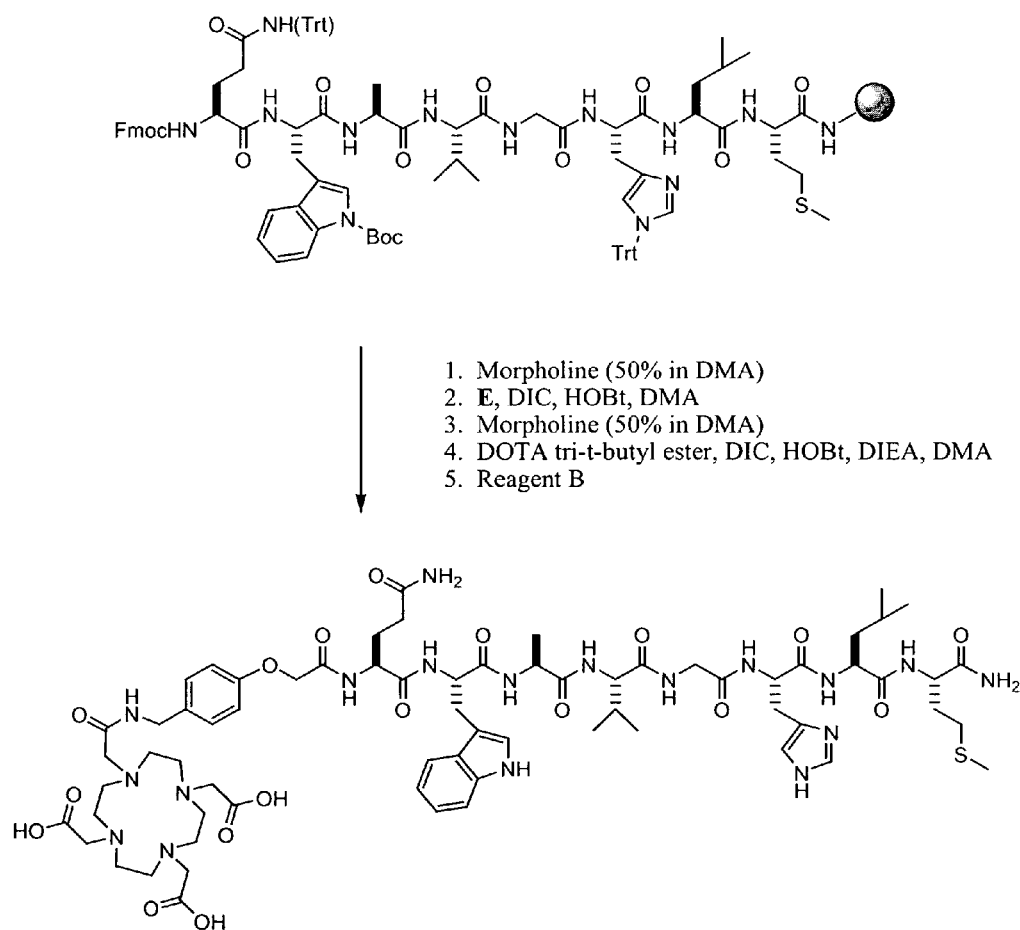
FIG. 7B is a graphical representation of the synthesis of N-[[4-[[[[4,7,10-Tris(carboxymethyl)-1,4,7,10-tetraazacyclododec-1-yl]acetyl]amino]methyl]phenoxy]acetyl]-L-glutaminyl-L-triptophyl-L-alanyl-L-valyl-glycyl-L-histidyl-L-leucyl-L-methioninamide (L124), as described in Example VII.
Figure 7C:
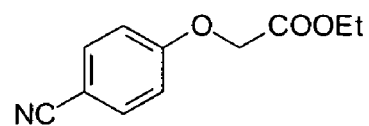
FIG. 7C is a chemical structure of (4-Cyanophenoxy) acetic acid ethyl ester (B), as described in Example VII.
Figure 7D:
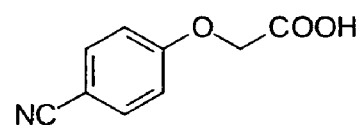
FIG. 7D is a chemical structure of (4-Cyanophenoxy) acetic acid (C), as described in Example VII.
Figure 7E:
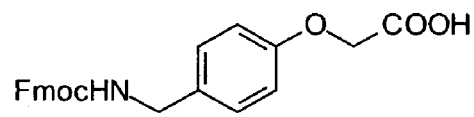
FIG. 7E is a chemical structure of [4-[[[9H-Fluoren-9-ylmethoxy)carbonyl]amino]methyl]phenoxy]acetic acid (E), as described in Example VII.
Figure 7F:
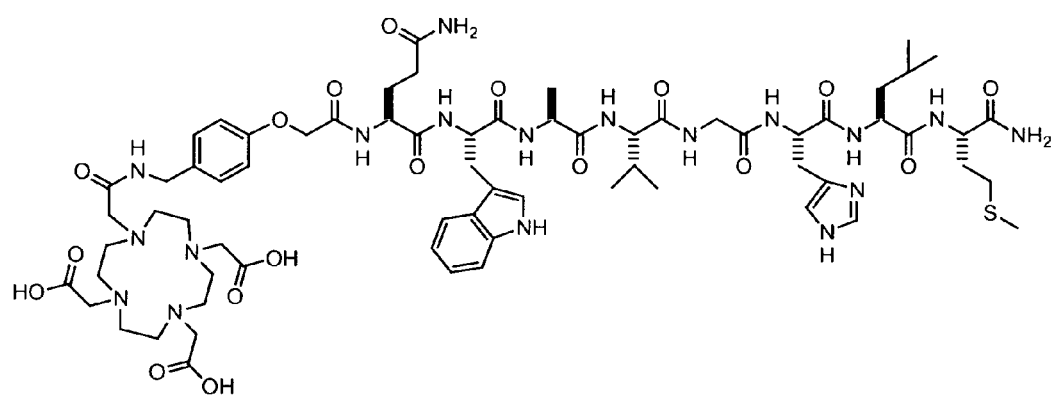
FIG. 7F is a chemical structure of N-[[4-[[[[4,7,10-Tris (carboxymethyl)-1,4,7,10-tetraazacyclododec-1-yl]acetyl] amino]methyl]phenoxy]acetyl]-L-glutaminyl-L-tryptophyl-L-alanyl-L-valyl-glycyl-L-histidyl-L-leucyl-L-methioninamide (L124), as described in Example VII.
Figure 8A:
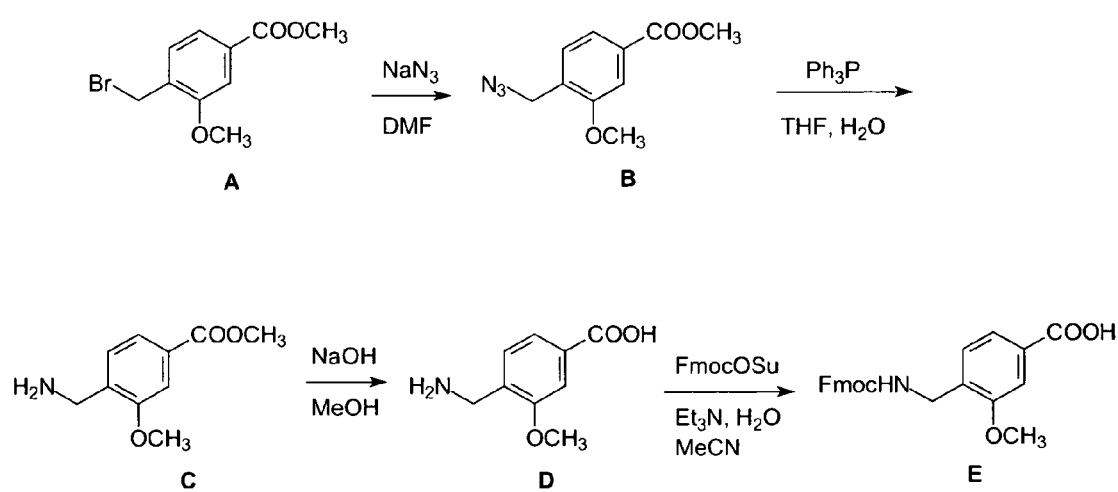
FIG. 8A is a graphical representation of a sequence of reactions for the synthesis of intermediate 4-[[[9H-Fluoren-9-ylmethoxy)carbonyl]amino]methyl]-3-methoxybenzoic acid (E), as described in Example VIII.
Figure 8B:
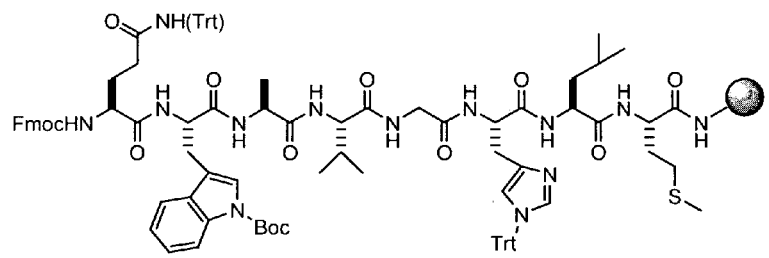
FIG. 8B is a graphical representation of the synthesis of N-[4-[[[[4,7,10-Tris(carboxymethyl)-1,4,7,10-tetraazacyclododec-1-yl]acetyl]amino]methyl]-3-methoxybenzoyl]-L-glutaminyl-L-tryptophyl-L-alanyl-L-valyl-glycyl-L-histidyl-L-leucyl-L-methioninamide, (L125), as described in Example VIII.
Figure 8B:
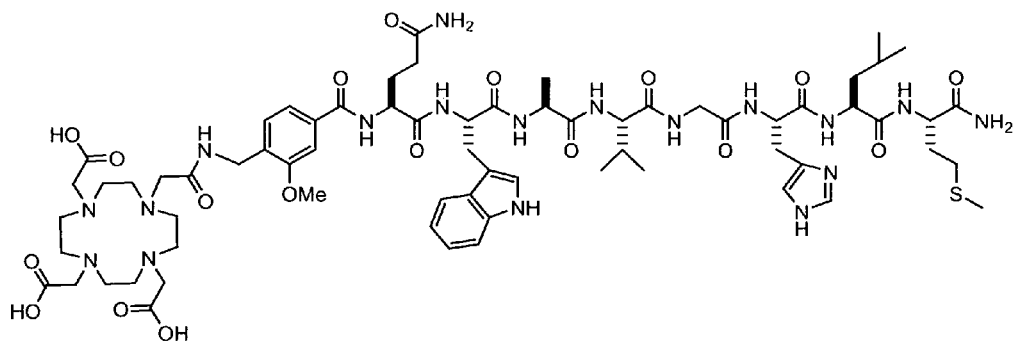
Figure 8C:
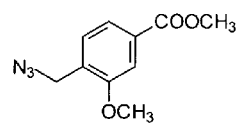
FIG. 8C is a chemical structure of 4-(Azidomethyl)-3-methoxybenzoic acid methyl ester, (B), as described in Example VIII.
Figure 8D:
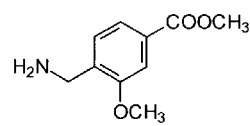
FIG. 8D is a chemical structure of 4-(Aminomethyl)-3-methoxybenzoic acid methyl ester, (C), as described in Example VIII.
Figure 8E:
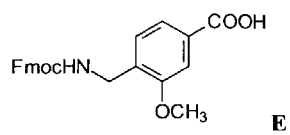
FIG. 8E is a chemical structure of 4-[[[9H-Fluoren-9-ylmethoxy)carbonyl]amino]methyl]-3-methoxybenzoic acid, (E), as described in Example VIII.
Figure 8F:
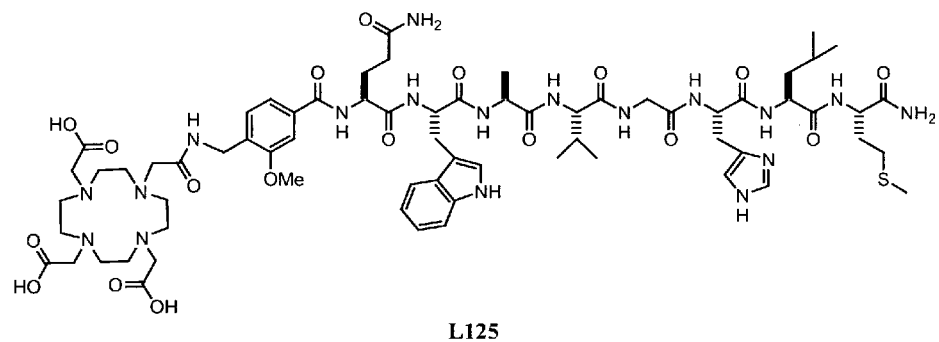
FIG. 8F is a chemical structure of N-[4-[[[[4,7,10-Tris (carboxymethyl)-1,4,7,10-tetraazacyclododec-1-yl]acetyl] amino]methyl]-3-methoxybenzoyl]-L-glutaminyl-L-tryptophyl-L-alanyl-L-valyl-glycyl-L-histidyl-L-leucyl-L-methioninamide, (L125), as described in Example VIII.

Summary: As shown in FIGS. 1A–B, L62 was prepared using the following steps: Hydrolysis of (3β,5β)-3-aminocholan-24-oic acid methyl ester A with NaOH gave the corresponding acid B, which was then reacted with Fmoc-Cl to give intermediate C. Rink amide resin functionalised with the octapeptide Gln-Trp-Ala-Val-Gly-His-Leu-Met-$NH_2$ (BBN[7-14] [SEQ ID NO:1]) was sequentially reacted with C, Fmoc-glycine and DOTA tri-t-butyl ester. After cleavage and deprotection with reagent B the crude was purified by preparative HPLC to give L62. Overall yield: 2.5%. More details are provided below:

A. Preparation of Intermediates B and C:

1. Synthesis of (3β,5β)-3-Aminocholan-24-oic acid (B)

A 1 M solution of NaOH (16.6 mL; 16.6 mmol) was added dropwise to a solution of (3β,5β)-3-aminocholan-24-oic acid methyl ester (5.0 g; 12.8 mmol) in MeOH (65 mL) at 45° C. After 3 h stirring at 45° C., the mixture was concentrated to 25 mL and $H_2O$ (40 mL) and 1 M HCl (22 mL) were added. The precipitated solid was filtered, washed with $H_2O$ (2×50 mL) and vacuum dried to give B as a white solid (5.0 g; 13.3 mmol). Yield 80%.

2. Synthesis of (3β,5β)-3-(9H-Fluoren-9-ylmethoxy)aminocholan-24-oic acid (C)

A solution of 9-fluorenylmethoxycarbonyl chloride (0.76 g; 2.93 mmol) in 1,4-dioxane (9 mL) was added dropwise to a suspension of (3β,5β)-3-aminocholan-24-oic acid B (1.0 g; 2.66 mmol) in 10% aq. $Na_2CO_3$ (16 mL) and 1,4-dioxane (9 mL) stirred at 0° C. After 6 h stirring at room temperature $H_2O$ (90 mL) was added, the aqueous phase washed with $Et_2O$ (2×90 mL) and then 2 M HCl (15 mL) was added (final pH: 1.5). The aqueous phase was extracted with EtOAc (2×100 mL), the organic phase dried over $Na_2SO_4$ and evaporated. The crude was purified by flash chromatography to give C as a white solid (1.2 g; 2.0 mmol). Yield 69%.

B. Synthesis of L62 (N-[(3β,5β)-3-[[[[[4,7,10-Tris(carboxymethyl)-1,4,7,10-tetraazacyclododec-1-yl]acetyl]amino]acetyl]amino]-cholan-24-yl]-L-glutaminyl-L-tryptophyl-L-alanyl-L-valyl-glycyl-L-histidyl-L-leucyl-L-methioninamide):

Resin D (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was shaken for 20 min then the solution was emptied and the resin washed with DMA (5×7 mL). (3β,5β)-3-(9H-Fluoren-9-ylmethoxy)aminocholan-24-oic acid C (0.72 g; 1.2 mmol), N-hydroxybenzotriazole (HOBt) (0.18 g; 1.2 mmol), N,N'-diisopropylcarbodiimide (DIC) (0.19 mL; 1.2 mmol) and DMA (7 mL) were added to the resin, the mixture shaken for 24 h at room temperature, and the solution was emptied and the resin washed with DMA (5×7 mL). The resin was then shaken with 50% morpholine in DMA (7 mL) for 10 min, the solution was emptied, fresh 50% morpholine in DMA (7 mL) was added and the mixture shaken for another 20 min. The solution was emptied and the resin washed with DMA (5×7 mL). N-α-Fmoc-glycine (0.79 g; 1.2 mmol), HOBt (0.18 g; 1.2 mmol), DIC (0.19 mL: 1.2 mmol) and DMA (7 mL) were added to the resin. The mixture was shaken for 3 h at room temperature, the solution was emptied and the resin washed with DMA (5×7 mL). The resin was then shaken with 50% morpholine in DMA (7 mL) for 10 min, the solution was emptied, fresh 50% morpholine in DMA (7 mL) was added and the mixture shaken for another 20 min. The solution was emptied and the resin washed with DMA (5×7 mL) followed by addition of 1,4,7,10-Tetraazacyclododecane-1,4,7,10-tetraacetic acid tris(1,1-dimethylethyl)ester adduct with NaCl (0.79 g; 1.2 mmol), HOBt (0.18 g; 1.2 mmol), DIC (0.19 mL: 1.2 mmol), DIEA (0.40 mL; 2.4 mmol) and DMA (7 mL) to the resin. The mixture was shaken for 24 h at room temperature, the solution was emptied and the resin washed with DMA (5×7 mL), $CH_2Cl_2$ (5×7 mL) and vacuum dried. The resin was shaken in a flask with reagent B (25 mL) for 4.5 h. The resin was filtered and the solution was evaporated under reduced pressure to afford an oily crude which was triturated with $Et_2O$ (20 mL) gave a precipitate. The precipitate was collected by centrifugation and washed with $Et_2O$ (3×20 mL), then analysed by HPLC and purified by preparative HPLC. The fractions containing the product were lyophilised to give L62 (6.6 mg; 3.8×10$^{-3}$ mmol) as a white solid. Yield 4.5%.

Example II

FIGS. 2A–F

Synthesis of L70, L73, L74, L115 and L116

Summary: The products were obtained by coupling of the octapeptide Gln-Trp-Ala-Val-Gly-His-Leu-Met-$NH_2$ (BBN [7-14] [SEQ ID NO:1]) (with appropriate side chain protection) on the Rink amide resin with different linkers, followed by functionalization with DOTA tri-t-butyl ester. After cleavage and deprotection with reagent B the final products were purified by preparative HPLC. Overall yields 3–9%.

A. Synthesis of L70:

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin was washed with DMA (5×7 mL). Fmoc-4-aminobenzoic acid (0.43 g; 1.2 mmol), HOBt (0.18 g; 1.2 mmol), DIC (0.19 mL; 1.2 mmol) and DMA (7 mL) were added to the resin, the mixture shaken for 3 h at room temperature, the solution was emptied and the resin was washed with DMA (5×7 mL). The resin was then shaken with 50% morpholine in DMA (7 mL) for 10 min, the solution was emptied, fresh 50% morpholine in DMA (7 mL) was added and the mixture was shaken for 20 min. The solution was emptied and the resin washed with DMA (5×7 mL). Fmoc-glycine (0.36 g; 1.2 mmol), N,N,N',N'-tetramethyl-O-(7-azabenzotriazol-1-yl)uronium hexafluorophosphate (HATU) (0.46 g; 1.2 mmol) and DIEA (0.40 mL; 2.4 mmol) were stirred for 15 min in DMA (7 mL) then the solution was added to the resin, the mixture shaken for 2 h at room temperature, the solution was emptied and the resin was washed with DMA (5×7 mL). The resin was then shaken with 50% morpholine in DMA (7 mL) for 10 min, the solution was emptied, fresh 50% morpholine in DMA (7 mL) was added and the mixture shaken for 20 min. The solution was emptied and the resin washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin washed with DMA (5×7 mL), $CH_2Cl_2$ (5×7 mL) and vacuum dried. The resin was shaken in a flask with reagent B (25 mL) for 4 h. The resin was filtered and the filtrate solution was evaporated under reduced pressure to afford an oily crude that was triturated with $Et_2O$ (5 mL). The precipitate was collected by centrifugation and washed with $Et_2O$ (5×5 mL), then analysed by HPLC and purified by preparative HPLC. The fractions containing the product were lyophilised to give L70 as a white fluffy solid (6.8 mg; 0.005 mmol). Yield 3%.

B. Synthesis of L73, L115 and L116:

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin washed with DMA (5×7 mL). Fmoc-linker (1.2 mmol), N-hydroxybenzotriazole (HOBt) (0.18 g; 1.2 mmol), N,N'-diisopropylcarbodiimide (DIC) (0.19 mL; 1.2 mmol) and DMA (7 mL) were added to the resin, the mixture was shaken for 3 h at room temperature, the solution was emptied and the resin was washed with DMA (5×7 mL). The resin was shaken with 50% morpholine in DMA (7 mL) for 10 min, the solution was emptied, fresh 50% morpholine in DMA (7 mL) was added and the mixture was shaken for 20 min. The solution was emptied and the resin washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin washed with DMA (5×7 mL), $CH_2Cl_2$ (5×7 mL) and vacuum dried. The resin was shaken in a flask with reagent B (25 mL) for 4 h. The resin was filtered and the solution was evaporated under reduced pressure to afford an oily crude that was triturated with $Et_2O$ (5 mL). The precipitate was collected by centrifugation and washed with $Et_2O$ (5×5 mL), then analysed by HPLC and purified by preparative HPLC. The fractions containing the product were lyophilised.

D. Synthesis of L74:

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin was washed with DMA (5×7 mL). Fmoc-isonipecotic acid (0.42 g; 1.2 mmol), HOBt (0.18 g; 1.2 mmol), DIC (0.19 mL; 1.2 mmol) and DMA (7 mL) were added to the resin, the mixture was shaken for 3 h at room temperature, the solution was emptied and the resin was washed with DMA (5×7 mL). The resin was shaken with 50% morpholine in DMA (7 mL) for 10 min, the solution was emptied, fresh 50% morpholine in DMA (7 mL) was added and the mixture was shaken for 20 min. The solution was emptied and the resin was washed with DMA (5×7 mL). Fmoc-glycine (0.36 g; 1.2 mmol), HOBt (0.18 g; 1.2 mmol), DIC (0.19 mL; 1.2 mmol) and DMA (7 mL) were added to the resin, the mixture was shaken for 3 h at room temperature, the solution was emptied and the resin washed with DMA (5×7 mL). The resin was then shaken with 50% morpholine in DMA (7 mL) for 10 min, the solution was emptied, fresh 50% morpholine in DMA (7 mL) was added and the mixture shaken for 20 minutes. The solution was emptied and the resin was washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin was washed with DMA (5×7 mL), $CH_2Cl_2$ (5×7 mL) and vacuum dried. The resin was shaken in a flask with reagent B (25 mL) for 4 h. The resin was filtered and the solution was evaporated under reduced pressure to afford an oily crude that was triturated with $Et_2O$ (5 mL). The precipitate was collected by centrifugation and washed with $Et_2O$ (5×5 mL), then analysed by HPLC and purified by HPPLC. The fractions containing the product were lyophilised to give L74 as a white fluffy solid (18.0 mg; 0.012 mmol). Yield 8%.

Example III

FIGS. 3A–E

Synthesis of L67

Summary: Hydrolysis of (3β,5β)-3-amino-12-oxocholan-24-oic acid methyl ester A with NaOH gave the corresponding acid B, which was then reacted with Fmoc-Glycine to give intermediate C. Rink amide resin functionalised with the octapeptide Gln-Trp-Ala-Val-Gly-His-Leu-Met-$NH_2$ (BBN[7-14] [SEQ ID NO:1]) was sequentially reacted with C, and DOTA tri-t-butyl ester. After cleavage and deprotection with reagent B the crude was purified by preparative HPLC to give L67. Overall yield: 5.2%.

A. Synthesis (3β,5β)-3-Amino-12-oxocholan-24-oic acid, (B)

A 1 M solution of NaOH (6.6 mL; 6.6 mmol) was added dropwise to a solution of (3β,5β)-3-amino-12-oxocholan-24-oic acid methyl ester A (2.1 g; 5.1 mmol) in MeOH (15 mL) at 45° C. After 3 h stirring at 45° C., the mixture was concentrated to 25 mL then $H_2O$ (25 mL) and 1 M HCl (8 mL) were added. The precipitated solid was filtered, washed with $H_2O$ (2×30 mL) and vacuum dried to give B as a white solid (1.7 g; 4.4 mmol). Yield 88%.

B. Synthesis of (3β,5β)-3-[[(9H-Fluoren-9-ylmethoxy)amino]acetyl]amino-12-oxocholan-24-oic acid (C).

Tributylamine (0.7 mL; 3.1 mmol) was added dropwise to a solution of N-α-Fmoc-glycine (0.9 g; 3.1 mmol) in THF (25 mL) stirred at 0° C. Isobutyl chloroformate (0.4 mL; 3.1 mmol) was subsequently added and, after 10 min, a suspension of tributylamine (0.6 mL; 2.6 mmol) and (3β,5β)-3-amino-12-oxocholan-24-oic acid B (1.0 g; 2.6 mmol) in DMF (30 mL) was added dropwise, over 1 h, into the cooled solution. The mixture was allowed to warm up and after 6 h the solution was concentrated to 40 mL, then $H_2O$ (50 mL) and 1 N HCl (10 mL) were added (final pH: 1.5). The precipitated solid was filtered, washed with $H_2O$ (2×50 mL), vacuum dried and purified by flash chromatography to give C as a white solid (1.1 g; 1.7 mmol). Yield 66%.

C. Synthesis of L67 (N-[(3β,5β)-3-[[[[[4,7,10-Tris(carboxymethyl)-1,4,7,10-tetraazacyclododec-1-yl]acetyl]amino]acetyl]amino]-12,24-dioxocholan-24-yl]-L-glutaminyl-L-tryptophyl-L-alanyl-L-valyl-glycyl-L-histidyl-L-leucyl-L-methioninamide).

Resin D (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin was washed with DMA (5×7 mL). (3β,5β)-3-[[(9H-Fluoren-9-ylmethoxy)amino]acetyl]amino]-12-oxocholan-24-oic acid C (0.80 g; 1.2 mmol), N-hydroxybenzotriazole (HOBt) (0.18 g; 1.2 mmol), N,N'-diisopropylcarbodiimide (DIC) (0.19 mL; 1.2 mmol) and DMA (7 mL) were added to the resin, the mixture was shaken for 24 h at room temperature, the solution was emptied and the resin was washed with DMA (5×7 mL). The resin was shaken with 50% morpholine in DMA (7 mL) for 10 min, the solution was emptied, fresh 50% morpholine in DMA (7 mL) was added and the mixture was shaken for 20 min. The solution was emptied and the resin was washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin was washed with DMA (5×7 mL), $CH_2Cl_2$ (5×7 mL) and vacuum dried. The resin was shaken in a flask with reagent B (25 mL) for 4.5 h. The resin was filtered and the solution was evaporated under reduced pressure to afford an oily crude that was triturated with $Et_2O$ (20 mL).

Example IV

FIGS. 4A–H

Synthesis of L63 and L64

Summary: Hydrolysis of (3β,5β,7α,12α)-3-amino-7,12-dihydroxycholan-24-oic acid methyl ester 1b with NaOH gave the intermediate 2b, which was then reacted with Fmoc-glycine to give 3b. Rink amide resin functionalised with the octapeptide Gln-Trp-Ala-Val-Gly-His-Leu-Met-$NH_2$ (BBN [7-14] [SEQ ID NO:1]) was reacted with 3b and then with DOTA tri-t-butyl ester. After cleavage and deprotection with reagent B the crude was purified by preparative HPLC to give L64. The same procedure was repeated starting from intermediate 2a, already available, to give L63. Overall yields: 9 and 4%, respectively.

A. Synthesis of (3β,5β,7α,12α)-3-Amino-7,12-dihydroxycholan-24-oic acid, (2b)

A 1 M solution of NaOH (130 mL; 0.13 mol) was added dropwise to a solution of (3β,5β,7α,12α)-3-amino-7, 12-dihydroxycholan-24-oic acid methyl ester 1b (42.1 g; 0.10 mol) in MeOH (300 mL) heated at 45° C. After 3 h stirring at 45° C., the mixture was concentrated to 150 mL and H$_2$O (350 mL) was added. After extraction with CH$_2$Cl$_2$ (2×100 mL) the aqueous solution was concentrated to 200 mL and 1 M HCl (150 mL) was added. The precipitated solid was filtered, washed with H$_2$O (2×100 mL) and vacuum dried to give 2b as a white solid (34.8 g; 0.08 mol). Yield 80%.

B. Synthesis of (3β,5β,12α)-3-[[(9H-Fluoren-9-ylmethoxy)amino]acetyl]amino-12-hydroxycholan-24-oic acid, (3a)

Tributylamine (4.8 mL; 20.2 mmol) was added dropwise to a solution of N-α-Fmoc-glycine (6.0 g; 20.2 mmol) in THF (120 mL) stirred at 0° C. Isobutyl chloroformate (2.6 mL; 20.2 mmol) was subsequently added and, after 10 min, a suspension of tributylamine (3.9 mL; 16.8 mmol) and (3β,5β,12α)-3-amino-12-hydroxycholan-24-oic acid 2a (6.6 g; 16.8 mmol) in DMF (120 mL) was added dropwise, over 1 h, into the cooled solution. The mixture was allowed to warm up and after 6 h the solution was concentrated to 150 mL, then H$_2$O (250 mL) and 1 N HCl (40 mL) were added (final pH: 1.5). The precipitated solid was filtered, washed with H$_2$O (2×100 mL), vacuum dried and purified by flash chromatography to give 3a as a white solid (3.5 g; 5.2 mmol). Yield 31%.

C. Synthesis of (3β,5β,7α,12α)-3-[[(9H-Fluoren-9-ylmethoxy)amino]acetyl]amino-7,12-dihydroxycholan-24-oic acid, (3b)

Tributylamine (3.2 mL; 13.5 mmol) was added dropwise to a solution of N-α-Fmoc-glycine (4.0 g; 13.5 mmol) in THF (80 mL) stirred at 0° C. Isobutyl chloroformate (1.7 mL; 13.5 mmol) was subsequently added and, after 10 min, a suspension of tributylamine (2.6 mL; 11.2 mmol) and (3β,5β,7α,12α)-3-amino-7,12-dihydroxycholan-24-oic acid 3a (4.5 g; 11.2 mmol) in DMF (80 mL) was added dropwise, over 1 h, into the cooled solution. The mixture was allowed to warm up and after 6 h the solution was concentrated to 120 mL, then H$_2$O (180 mL) and 1 N HCl (30 mL) were added (final pH: 1.5). The precipitated solid was filtered, washed with H$_2$O (2×100 mL), vacuum dried and purified by flash chromatography to give 3a as a white solid (1.9 g; 2.8 mmol). Yield 25%.

In an alternative method, (3β,5β,7α,12α)-3-[[(9H-Fluoren-9-ylmethoxy)amino]acetyl]amino-7,12-dihydroxycholan-24-oic acid, (3b) can be prepared as follows:

N-Hydroxysuccinimide (1.70 g, 14.77 mmol) and DIC (1.87 g, 14.77 mmol) were added sequentially to a stirred solution of Fmoc-Gly-OH (4.0 g, 13.45 mmol) in dichloromethane (15 mL); the resulting mixture was stirred at room temperature for 4 h. The N,N'-diisopropylurea formed was removed by filtration and the solid was washed with ether (20 mL). The volatiles were removed and the solid Fmoc-Gly-succinimidyl ester formed was washed with ether (3×20 mL). Fmoc-Gly-succinimidyl ester was then redissolved in dry DMF (15 mL) and 3-aminodeoxycholic acid (5.21 g, 12.78 mmol) was added to the clear solution. The reaction mixture was stirred at room temperature for 4 h, water (200 mL) was added and the precipitated solid was filtered, washed with water, dried and purified by silica gel chromatography (TLC (silica): (R$_f$: 0.50, silica gel, CH$_2$Cl$_2$/CH$_3$OH, 9:1) (eluant: CH$_2$Cl$_2$/CH$_3$OH (9:1) to give Fmoc-Gly-3-aminocholic acid as a colorless solid. Yield: 7.46 g (85%).

D. Synthesis of L63 (N-[(3β,5β,12α)-3-[[[[4,7,10-Tris(carboxymethyl)-1,4,7,10-tetraazacyclododec-1-yl]acetyl]amino]acetyl]amino]-12-hydroxy-24-oxocholan-24-yl]-L-glutaminyl-L-tryptophyl-L-alanyl-L-valyl-glycyl-L-histidyl-L-leucyl-L-methioninamide)

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin washed with DMA (5×7 mL). (3β,5β,12α)-3-[[(9H-Fluoren-9-ylmethoxy)amino]acetyl]amino-12-hydroxycholan-24-oic acid 3a (0.82 g; 1.2 mmol), N-hydroxybenzotriazole (HOBt) (0.18 g; 1.2 mmol), N,N'-diisopropylcarbodiimide (DIC) (0.19 mL; 1.2 mmol) and DMA (7 mL) were added to the resin, the mixture was shaken for 24 h at room temperature, the solution was emptied and the resin was washed with DMA (5×7 mL). The resin was then shaken with 50% morpholine in DMA (7 mL) for 10 min, the solution was emptied, fresh 50% morpholine in DMA (7 mL) was added and the mixture was shaken for 20 min. The solution was emptied and the resin washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin washed with DMA (5×7 mL), CH$_2$Cl$_2$ (5×7 mL) and vacuum dried. The resin was shaken in a flask with reagent B (25 mL) for 4 h. The resin was filtered and the solution was evaporated under reduced pressure to afford an oily crude that after treatment with Et$_2$O (5 mL) gave a precipitate. The precipitate was collected by centrifugation and washed with Et$_2$O (5×5 mL), then analysed and purified by HPLC. The fractions containing the product were lyophilised to give L63 as a white fluffy solid (12.8 mg; 0.0073 mmol). Yield 9%.

E. Synthesis of L64 (N-[(3β,5β,7α,12α)-3-[[[[4,7,10-Tris(carboxymethyl)-1,4,7,10-tetraazacyclododec-1-yl]acetyl]amino]acetyl]amino]-7,12-dihydroxy-24-oxocholan-24-yl]-L-glutaminyl-L-tryptophyl-L-alanyl-L-valyl-glycyl-L-histidyl-L-leucyl-L-methioninamide)

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min, the solution was emptied and the resin was washed with DMA (5×7 mL). (3β,5β,7α,12α)-3-[[(9H-Fluoren-9-ylmethoxy)amino]acetyl]amino-7,12-dihydroxycholan-24-oic acid 3b (0.81 g; 1.2 mmol), HOBt (0.18 g; 1.2 mmol), DIC (0.19 mL; 1.2 mmol) and DMA (7 mL) were added to the resin, the mixture was shaken for 24 h at room temperature, the solution was emptied and the resin was washed with DMA (5×7 mL). The resin was shaken with 50% morpholine in DMA (7 mL) for 10 min, the solution was emptied, fresh 50% morpholine in DMA (7 mL) was added and the mixture was shaken for 20 min. The solution was emptied and the resin was washed with DMA (5×7 mL). 1,4,7,10-Tetraazacyclododecane-1,4,7,10-tetraacetic acid tris(11,1-dimethylethyl) ester adduct with NaCl (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin washed with DMA (5×7 mL), $CH_2Cl_2$ (5×7 mL) and vacuum dried. The resin was shaken in a flask with reagent B (25 mL) for 4 h. The resin was filtered and the solution was evaporated under reduced pressure to afford an oily crude that was triturated with $Et_2O$ (5 mL). The precipitate was collected by centrifugation and washed with $Et_2O$ (5×5 mL). Then it was dissolved in $H_2O$ (20 mL), and $Na_2CO_3$ (0.01 g; 0.70 mmol) was added; the resulting mixture was stirred 4 h at room temperature. This solution was purified by HPLC, the fractions containing the product lyophilised to give L64 as a white fluffy solid (3.6 mg; 0.0021 mmol). Yield 4%.

Example V

FIGS. 5A–E

Synthesis of L71 and L72

Summary: The products were obtained in two steps. The first step was the solid phase synthesis of the octapeptide Gln-Trp-Ala-Val-Gly-His-Leu-Met-$NH_2$ (BBN[7-14] [SEQ ID NO:1]) (with appropriate side chain protecting groups) on the Rink amide resin. The second step was the coupling with different linkers followed by functionalization with DOTA tri-t-butyl ester. After cleavage and deprotection with reagent B the final products were purified by preparative HPLC. Overall yields 3–9%.

A. Rink Amide Resin Functionalised with Bombesin[7-14], (B)

In a solid phase peptide synthesis vessel (see enclosure No. 1) Fmoc-aminoacid (24 mmol), N-hydroxybenzotriazole (HOBt) (3.67 g; 24 mmol), and N,N'-diisopropylcarbodiimide (DIC) (3.75 mL; 24 mmol) were added sequentially to a suspension of Rink amide NovaGel™ resin (10 g; 6.0 mmol) A in DMF (45 mL). The mixture was shaken for 3 h at room temperature using a bench top shaker, then the solution was emptied and the resin was washed with DMF (5×45 mL). The resin was shaken with 25% piperidine in DMF. (45 mL) for 4 min, the solution was emptied and fresh 25% piperidine in DMF (45 mL) was added. The suspension was shaken for 10 min, then the solution was emptied and the resin was washed with DMF (5×45 mL).

This procedure was applied sequentially for the following amino acids: N-α-Fmoc-L-methionine, N-α-Fmoc-L-leucine, N-α-Fmoc-N-im-trityl-L-histidine, N-α-Fmoc-glycine, N-α-Fmoc-L-valine, N-α-Fmoc-L-alanine, N-α-Fmoc-N-in-Boc-L-tryptophan.

In the last coupling reaction N-α-Fmoc-N-γ-trityl-L-glutamine (14.6 g; 24 mmol), HOBt (3.67 g; 24 mmol), and DIC (3.75 mL; 24 mmol) were added to the resin in DMF (45 mL). The mixture was shaken for 3 h at room temperature, the solution was emptied and the resin was washed with DMF (5×45 mL), $CH_2Cl_2$ (5×45 mL) and vacuum dried.

B. Bombesin [7-14] Functionalisation and Cleavage Procedure

The resin B (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin was washed with DMA (5×7 mL). The Fmoc-linker (1.2 mmol), HOBt (0.18 g; 1.2 mmol), DIC (0.19 mL; 1.2 mmol) and DMA (7 mL) were added to the resin. The mixture was shaken for 3 h at room temperature, the solution was emptied and the resin washed with DMA (5×7 mL). The resin was then shaken with 50% morpholine in DMA (7 mL) for 10 min, the solution was emptied, fresh 50% morpholine in DMA (7 mL) was added and the mixture was shaken for 20 min. The solution was emptied and the resin was washed with DMA (5×7 mL). 1,4,7,10-Tetraazacyclododecane-1,4,7,10-tetraacetic acid tris(1,1-dimethylethyl) ester adduct with NaCl C (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature. The solution was emptied and the resin washed with DMA (5×7 mL), $CH_2Cl_2$ (5×7 mL) and vacuum dried. The resin was shaken in a flask with reagent B (25 mL) for 4 h. The resin was filtered and the filtrate was evaporated under reduced pressure to afford an oily crude that was triturated with ether (5 mL). The precipitate was collected by centrifugation and washed with ether (5×5 mL), then analyzed by analytical HPLC and purified by preparative HPLC. The fractions containing the product were lyophilized.

C. Products
1. L71 (4-[[[[4,7,10-Tris(carboxymethyl)-1,4,7,10-tetraazacyclododec-1-yl]acetyl]amino]methyl]benzoyl-L-glutaminyl-L-tryptophyl-L-alanyl-L-valyl-glycil-L-histidyl-L-leucyl-L-methioninamide)

The product was obtained as a white fluffy solid (7.3 mg; 0.005 mmol). Yield 7.5%.

2. L72 (Trans-4-[[[[4,7,10-tris(carboxymethyl)-1,4,7,10-tetraazacyclododec-1-yl]acetyl]amino]methyl]cyclohexylcarbonyl-L-glutaminyl-L-tryptophyl-L-alanyl-L-valyl-glycil-L-histidyl-L-leucyl-L-methioninamide)

The product was obtained as a white fluffy solid (7.0 mg; 0.005 mmol). Yield 4.8%.

D. Trans-4-[[[(9H-fluoren-9-ylmethoxy)carbonyl]amino]methyl]cyclohexanecarboxylic acid, (D)

A solution of N-(9-fluorenylmethoxycarbonyloxy)succinimide (4.4 g; 14.0 mmol) in 1,4-dioxane (40 mL) was added dropwise to a solution of trans-4-(aminomethyl) cyclohexanecarboxylic acid (2.0 g; 12.7 mmol) in 10% $Na_2CO_3$ (30 mL) cooled to 0° C. The mixture was then allowed to warm to ambient temperature and after 1 h stirring at room temperature was treated with 1 N HCl (32 mL) until the final pH was 2. The resulting solution was extracted with n-BuOH (100 mL); the volatiles were removed and the crude residue was purified by flash chromatography to give D as a white solid (1.6 g; 4.2 mmol). Yield 33%.

Example VI

FIGS. 6A–K

Synthesis of L75 and L76

Summary: The two products were obtained by coupling of the octapeptide Gln-Trp-Ala-Val-Gly-His-Leu-Met-NH2 (BBN[7-14] [SEQ ID NO:1]) on the Rink amide resin with the two linkers E and H, followed by functionalization with DOTA tri-t-butyl ester. After cleavage and deprotection with reagent B the final products were purified by preparative HPLC. Overall yields: 8.5% (L75) and 5.6% (L76).

A. 2-[(1,3-Dihydro-1,3-dioxo-2H-isoindol-2-yl)methyl] benzoic acid, (C)

The product was synthesized following the procedure reported in the literature (Bornstein, J; Drummon, P. E.; Bedell, S. F. Org Synth. Coll. Vol. IV 1963, 810–812).

B. 2-(Aminomethyl)benzoic acid, (D)

A 40% solution of methylamine (6.14 mL; 7.1 mmol) was added to 2-[(1,3-dihydro-1,3-dioxo-2H-isoindol-2-yl) methyl]benzoic acid C (2 g; 7.1 mmol) and then EtOH (30 mL) was added. After 5 minutes stirring at room temperature the reaction mixture was heated at 50° C. After 2.5 h, the mixture was cooled and the solvent was evaporated under reduced pressure. The crude product was suspended in 50 mL of absolute ethanol and the suspension was stirred at room temperature for 1 h. The solid was filtered and washed with EtOH to afford 2-(aminomethyl)benzoic acid D (0.87 g; 5.8 mmol). Yield 81%.

C. 2-[[(9H-Fluoren-9-ylmethoxy)carbonyl]amino]methyl]benzoic acid, (E)

The product was synthesized following the procedure reported in the literature (Sun, J-H.; Deneker, W. F. Synth. Commun. 1998, 28, 4525–4530).

D. 4-(Aminomethyl)-3-nitrobenzoic acid, (G)

4-(Bromomethyl)-3-nitrobenzoic acid (3.2 g; 12.3 mmol) was dissolved in 8% $NH_3$ in EtOH (300 mL) and the resulting solution was stirred at room temperature. After 22 h the solution was evaporated and the residue suspended in $H_2O$ (70 mL). The suspension was stirred for 15 min and filtered. The collected solid was suspended in $H_2O$ (40 mL) and dissolved by the addition of few drops of 25% aq. $NH_4OH$ (pH 12), then the pH of the solution was adjusted to 6 by addition of 6 N HCl. The precipitated solid was filtered, and washed sequentially with MeOH (3×5 mL), and $Et_2O$ (10 mL) and was vacuum dried (1.3 kPa; $P_2O_5$) to give 4-(aminomethyl)-3-nitrobenzoic acid as a pale brown solid (1.65 g; 8.4 mmol). Yield 68%.

E. 4-[[[9H-Fluoren-9-ylmethoxy)carbonyl]amino]methyl]-3-nitrobenzoic acid, (H)

4-(Aminomethyl)-3-nitrobenzoic acid G (0.8 g; 4 mmol) was dissolved in 10% aq. $Na_2CO_3$ (25 mL) and 1,4-dioxane (10 mL) and the solution was cooled to 0° C. A solution of 9-fluorenylmethyl chloroformate (Fmoc-Cl) (1.06 g; 4 mmol) in 1,4-dioxane (10 mL) was added dropwise for 20 min. After 2 h at 0–5° C. and 1 h at 10° C. the reaction mixture was filtered and the solution was acidified to pH 5 by addition of 1 N HCl. The precipitate was filtered, washed with $H_2O$ (2×2 mL) dried under vacuum (1.3 kPa; $P_2O_5$) to give 4-[[[9H-fluoren-9-ylmethoxy)carbonyl]amino]methyl]-3-nitrobenzoic acid as a white solid (1.6 g; 3.7 mmol). Yield 92%.

F. L75 (N-[2-[[[[4,7,10-Tris(carboxymethyl)-1,4,7,10-tetraazacyclododec-1-yl]acetyl]amino]methyl]benzoyl]-L-glutaminyl-L-tryptophyl-L-alanyl-L-valyl-glycyl-L-histidyl-L-leucyl-L-methioninamide)

Resin I (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin washed with DMA (5×7 mL). 2-[[[9H-Fluoren-9-ylmethoxy)carbonyl]amino]methyl]benzoic acid, E (0.45 g; 1.2 mmol), N-hydroxybenzotriazole (HOBt) (0.18 g; 1.2 mmol), N,N'-diisopropylcarbodiimide (DIC) (0.19 mL; 1.2 mmol) and DMA (7 mL) were added to the resin, the mixture shaken for 24 h at room temperature, the solution was emptied and the resin was washed with DMA (5×7 mL). The resin was then shaken with 50% morpholine in DMA (7 mL) for 10 min, the solution was emptied, fresh 50% morpholine in DMA (7 mL) was added and the mixture shaken for 20 min. The solution was emptied and the resin washed with DMA (5×7 mL). 1,4,7,10-Tetraazacyclododecane-1,4,7,10-tetraacetic acid tris(1,1-dimethylethyl) ester adduct with NaCl (DOTA tri-t-butyl ester) (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin was washed with DMA (5×7 mL), $CH_2Cl_2$ (5×7 mL) and vacuum dried. The resin was shaken in a flask with reagent B (25 mL) for 4.5 h. The resin was filtered and the filtrate was evaporated under reduced pressure to afford an oily crude that after treatment with $Et_2O$ (20 mL) gave a precipitate. The resulting precipitate was collected by centrifugation and was washed with $Et_2O$ (3×20 mL) to give L75 (190 mg; 0.13 mmol) as a white solid. Yield 44%.

G. L76 (N-[4-[[[[4,7,10-Tris(carboxymethyl)-1,4,7,10-tetraazacyclododec-1-yl]acetyl]amino]methyl]-3-nitrobenzoyl]-L-glutaminyl-L-tryptophyl-L-alanyl-L-valyl-glycyl-L-histidyl-L-leucyl-L-methioninamide)

Resin I (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin was washed with DMA (5×7 mL). 4-[[[9H-Fluoren-9-ylmethoxy)carbonyl]amino] methyl]-3-nitrobenzoic acid, H (0.50 g; 1.2 mmol), HOBt (0.18 g; 1.2 mmol), DIC (0.19 mL; 1.2 mmol) and DMA (7 mL) were added to the resin, the mixture was shaken for 24 h at room temperature, the solution was emptied and the resin was washed with DMA (5×7 mL). The resin was then shaken with 50% morpholine in DMA (7 mL) for 10 min, the solution was emptied, fresh 50% morpholine in DMA (7 mL) was added and the mixture was shaken for 20 min. The solution was emptied and the resin was washed with DMA (5×7 mL). DOTA tri-t-butyl ester (0.79 g; 1.2 mmol), HOBt (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin was washed with DMA (5×7 mL), $CH_2Cl_2$ (5×7 mL) and vacuum dried. The resin was shaken in a flask with reagent B (25 mL) for 4.5 h. The resin was filtered and the solution was evaporated under reduced pressure to afford an oily crude that was triturated with $Et_2O$ (20 mL). The precipitate was collected by centrifugation and was washed with $Et_2O$ (3×20 mL) to give a solid (141 mg) which was analysed by HPLC. A 37 mg portion of the crude was purified by preparative HPLC. The fractions containing the product were lyophilised to give L76 (10.8 mg; $7.2 \times 10^{-3}$ mmol) as a white solid. Yield 9%.

Example VII

FIGS. 7A–F

Synthesis of L124

Summary: 4-Cyanophenol A was reacted with ethyl bromoacetate and $K_2CO_3$ in acetone to give the intermediated B, which was hydrolysed with NaOH to the corresponding acid C. Successive hydrogenation of C with $H_2$ and $PtO_2$ at 355 kPa in $EtOH/CHCl_3$ gave the corresponding aminoacid D, which was directly protected with FmocOSu to give E. Rink amide resin functionalised with the octapeptide Gln-Trp-Ala-Val-Gly-His-Leu-Met-$NH_2$ (BBN[7-14] [SEQ ID NO:1]) was reacted with E and then with DOTA tri-t-butyl ester. After cleavage and deprotection with reagent B the crude was purified by preparative HPLC to give L124. Overall yield: 1.3%

A. Synthesis of (4-Cyanophenoxy)acetic acid ethyl ester, (B)

The product was synthesized following the procedure reported in the literature (Archimbault, P.; LeClerc, G.; Strosberg, A. D.; Pietri-Rouxel, F. PCT Int. Appl. WO 980005, 1998).

B. Synthesis of (4-Cyanophenoxy)acetic acid, (C)

A 1 N solution of NaOH (7.6 mL; 7.6 mmol) was added dropwise to a solution of (4-cyanophenoxy)acetic acid ethyl ester B (1.55 g; 7.6 mmol) in MeOH (15 mL). After 1 h the solution was acidified with 1 N HCl (7.6 mL; 7.6 mmol) and evaporated. The residue was taken up with water (20 mL) and extracted with $CHCl_3$ (2×30 mL). The organic phases were evaporated and the crude was purified by flash chromatography to give (4-cyanophenoxy)acetic acid C (0.97 g; 5.5 mmol) as a white solid. Yield 72%.

C. Synthesis of [4-[[[9H-Fluoren-9-ylmethoxy)carbonyl]amino]methyl]phenoxy]acetic acid, (E)

$PtO_2$ (150 mg) was added to a solution of (4-cyanophenoxy)acetic acid C (1.05 g; 5.9 mmol) in EtOH (147 mL) and $CHCl_3$ (3 mL). The suspension was stirred 30 h under a hydrogen atmosphere (355 kPa; 20° C.). The mixture was filtered through a Celite® pad and the solution evaporated under vacuum. The residue was purified by flash chromatography to give acid D (0.7 g) which was dissolved in $H_2O$ (10 mL), MeCN (2 mL) and $Et_3N$ (0.6 mL) at 0° C., then a solution of N-(9-fluorenylmethoxycarbonyloxy)succinimide (1.3 g; 3.9 mmol) in MeCN (22 mL) was added dropwise. After stirring 16 h at room temperature the reaction mixture was filtered and the volatiles were removed under vacuum. The residue was treated with 1 N HCl (10 mL) and the precipitated solid was filtered and purified by flash chromatography to give [4-[[[9H-fluoren-9-ylmethoxy)carbonyl]amino]methyl]phenoxy]acetic acid E (0.56 g; 1.4 mmol) as a white solid. Overall yield 24%.

E. Synthesis of L124 (N-[[4-[[[[4,7,10-Tris(carboxymethyl)-1,4,7,10-tetraazacyclododec-1-yl]acetyl]amino]methyl]phenoxy]acetyl]-L-glutaminyl-L-tryptophyl-L-alanyl-L-valyl-glycyl-L-histidyl-L-leucyl-L-methioninamide)

Resin F (480 mg; 0.29 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min, the solution was emptied and the resin was washed with DMA (5×7 mL). [4-[[[9H-Fluoren-9-ylmethoxy)carbonyl]amino]methyl]phenoxy]acetic acid E (480 mg; 1.19 mmol), N-hydroxybenzotriazole (HOBt) (182 mg; 1.19 mmol), N,N'-diisopropylcarbodiimide (DIC) (185 µL; 1.19 mmol) and DMA (7 mL) were added to the resin, the mixture was shaken for 24 h at room temperature, the solution was emptied and the resin was washed with DMA (5×7 mL). The resin was then shaken with 50% morpholine in DMA (6 mL) for 10 min, the solution was emptied, fresh 50% morpholine in DMA (6 mL) was added and the mixture was shaken for 20 min. The solution was emptied and the resin was washed with DMA (5×7 mL). 1,4,7,10-Tetraazacyclododecane-1,4,7,10-tetraacetic acid tris(1,1-dimethylethyl) ester adduct with NaCl (750 mg; 1.19 mmol), HOBt (182 mg; 1.19 mmol), DIEA (404 µL; 2.36 mmol), DIC (185 µL; 1.19 mmol) and DMA (6 mL) were added to the resin. The mixture was shaken for 24 h at room temperature, the solution was emptied, the resin was washed with DMA (2×7 mL), $CH_2Cl_2$ (5×7 mL) and vacuum dried. The resin was shaken in a flask with Reagent B (25 mL) for 4 h. The resin was filtered and the filtrate was evaporated under reduced pressure to afford an oily crude that was triturated with $Et_2O$ (5 mL). The precipitate was collected by centrifugation and washed with $Et_2O$ (5×5 mL) to give a solid (148 mg) which was analysed by HPLC. A 65 mg portion of the crude was purified by preparative HPLC. The fractions containing the product were lyophilised to give L127 as a white solid (15 mg; 0.01 mmol). Yield 7.9%.

Example VIII

FIGS. 8A–F

Synthesis of L125

Summary: 4-(Bromomethyl)-3-methoxybenzoic acid methyl ester A was reacted with $NaN_3$ in DMF to give the intermediate azide B, which was then reduced with $Ph_3P$ and $H_2O$ to amine C. Hydrolysis of C with NaOH gave acid D, which was directly protected with FmocOSu to give E. Rink amide resin functionalised with the octapeptide Gln-Trp-Ala-Val-Gly-His-Leu-Met-$NH_2$ (BBN[7-14] [SEQ ID NO:1]) was reacted with E and then with DOTA tri-t-butyl ester. After cleavage and deprotection with reagent B the crude was purified by preparative HPLC to give L125. Overall yield: 0.2%.

A. Synthesis of 4-(Azidomethyl)-3-methoxybenzoic acid methyl ester, (B)

A solution of 4-(bromomethyl)-3-methoxybenzoic acid methyl ester (8 g; 31 mmol) and $NaN_3$ (2 g; 31 mmol) in DMF (90 mL) was stirred overnight at room temperature. The volatiles were removed under vacuum and the crude product was dissolved in EtOAc (50 mL). The solution was washed with water (2×50 mL) and dried. The volatiles were evaporated to provide 4-(azidomethyl)-3-methoxybenzoic acid methyl ester (6.68 g; 30 mmol). Yield 97%.

B. 4-(Aminomethyl)-3-methoxybenzoic acid methyl ester, (C)

Triphenylphosphine (6.06 g; 23 mmol) was added to a solution of (4-azidomethyl)-3-methoxybenzoic acid methyl ester B (5 g; 22 mmol) in THF (50 mL): hydrogen evolution and formation of a white solid was observed. The mixture was stirred under nitrogen at room temperature. After 24 h more triphenylphosphine (0.6 g; 2.3 mmol) was added. After 24 h the azide was consumed and H$_2$O (10 mL) was added. After 4 h the white solid disappeared. The mixture was heated at 45° C. for 3 h and was stirred overnight at room temperature. The solution was evaporated to dryness and the crude was purified by flash chromatography to give 4-(aminomethyl)-3-methoxybenzoic acid methyl ester C (1.2 g; 6.1 mmol). Yield 28%.

C. 4-[[[9H-Fluoren-9-ylmethoxy)carbonyl]amino]methyl]-3-methoxybenzoic acid, (E)

A 1 N solution of NaOH (6.15 mL; 6.14 mmol) was added dropwise to a solution of 4-(aminomethyl)-3-methoxybenzoic acid methyl ester C (1.2 g; 6.14 mmol) in MeOH (25 mL) heated at 40° C. After stirring 8 h at 45° C. the solution was stirred over night at room temperature. A 1 N solution of NaOH (0.6 mL; 0.6 mmol) was added and the mixture heated at 40° C. for 4 h. The solution was concentrated, acidified with 1 N HCl (8 mL; 8 mmol), extracted with EtOAc (2×10 mL) then the aqueous layer was concentrated to 15 mL. This solution (pH 4.5) was cooled at 0° C. and Et$_3$N (936 µL; 6.75 mmol) was added (pH 11). A solution of N-(9-fluorenylmethoxycarbonyloxy)succinimide (3.04 g; 9 mmol) in MeCN (30 mL) was added dropwise (final pH 9) and a white solid precipitated. After stirring 1 h at room temperature the solid was filtered, suspended in 1N HCl (15 mL) and the suspension was stirred for 30 min. The solid was filtered to provide 4-[[[9H-fluoren-9-ylmethoxy)carbonyl]amino]methyl]-3-methoxybenzoic acid E as a white solid (275 mg; 0.7 mmol).

The filtrate was evaporated under vacuum and the resulting white residue was suspended in 1N HCl (20 mL) and stirred for 30 minutes. The solid was filtered and purified by flash chromatography to give more acid E (198 mg; 0.5 mmol). Overall yield 20%.

D. L125 (N-[4-[[[[4,7,10-Tris(carboxymethyl)-1,4,7,10-tetraazacyclododec-1-yl]acetyl]amino]methyl]-3-methoxybenzoyl]-L-glutaminyl-L-tryptophyl-L-alanyl-L-valyl-glycyl-L-histidyl-L-leucyl-L-methioninamide)

Resin F (410 mg; 0.24 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin was washed with DMA (5×7 mL). 4-[[[9H-Fluoren-9-ylmethoxy)carbonyl]amino]methyl]-3-methoxybenzoic acid E (398 mg; 0.98 mmol), N-hydroxybenzotriazole (HOBt) (151 mg; 0.98 mmol), N,N'-diisopropylcarbodiimide (DIC) (154 µL; 0.98 mmol) and DMA (6 mL) were added to the resin; the mixture was shaken for 24 h at room temperature, the solution was emptied and the resin was washed with DMA (5×7 mL). The resin was then shaken with 50% morpholine in DMA (6 mL) for 10 min, the solution was emptied, fresh 50% morpholine in DMA (6 mL) was added and the mixture was shaken for 20 min. The solution was emptied and the resin washed with DMA (5×7 mL). 1,4,7,10-Tetraazacyclododecane-1,4,7,10-tetraacetic acid tris(1,1-dimethylethyl) ester adduct with NaCl (618 mg; 0.98 mmol), HOBt (151 mg; 0.98 mmol), DIC (154 µL; 0.98 mmol), DIEA (333 µL; 1.96 mmol) and DMA (6 mL) were added to the resin. The mixture was shaken for 24 h at room temperature, the solution was emptied and the resin was washed with DMA (5×7 mL), CH$_2$Cl$_2$ (5×7 mL) and vacuum dried. The resin was shaken in a flask with reagent B (25 mL) for 4 h. The resin was filtered and the solution was evaporated under reduced pressure to afford an oily crude that was triturated with Et$_2$O (5 mL). The resulting precipitate was collected by centrifugation, was washed with Et$_2$O (5×5 mL), was analysed by HPLC and purified by preparative HPLC. The fractions containing the product were lyophilised to give L125 as a white solid (15.8 mg; 0.011 mmol). Yield 4.4%.

Example IX

Synthesis of Additional GRP Compounds

A. General Procedure for the Preparation of 4,4'-Aminomethylbiphenylcarboxylic acid (B2) and 3,3'-aminomethylbiphenylcarboxylic acid (B3):

1. Methyl-hydroxymethylbiphenylcarboxylates:
   Commercially available (Aldrich Chemical Co.) 4-hydroxymethylphenylboric acid or 3-hydroxymethylphenylboric acid (1.0 g, 6.58 mmol) was stirred with isopropanol (10 mL) and 2M sodium carbonate (16 mL) until the solution became homogeneous. The solution was degassed by passing nitrogen through the solution and then treated with solid methyl-3-bromobenzoate, or methyl-4-bromobenzoate (1.35 g, 6.3 mmol) followed by the Pd (0) catalyst {[(C$_6$H$_5$)$_3$P]$_4$Pd; 0.023 g, 0.003 mmol}. The reaction mixture was kept at reflux under nitrogen until the starting bromobenzoate was consumed as determined by TLC analysis (2–3 h). The reaction mixture was then diluted with 250 mL of water and extracted with ethyl acetate (3×50 mL). The organic layers were combined and washed with saturated sodium bicarbonate solution (2×50 mL) and dried (Na$_2$SO$_4$). The solvent was removed under reduced pressure and the residue was chromatographed over flash silica gel (100 g). Elution with 40% ethyl acetate in hexanes yielded the product either as a solid or oil.

Yield:
B2—0.45 g (31%); m.p.—170–171° C.
B3—0.69 g (62%); oil.
$^1$H NMR (CDCl$_3$) δ B2—3.94 (s,3H, —COOCH$_3$), 4.73 (s, 2H, —CH$_2$-Ph), 7.475 (d, 2H, J=5 Hz), 7.6 (d, 2H, J=10 Hz), 7.65 (d, 2H, J=5 Hz) and 8.09 (d, 2H, J=10 Hz).
M.S.—m/e—243.0 [M+H]
B3—3.94 (s, 3H, —COOCH$_3$), 4.76 (s, 2H, —CH$_2$-Ph), 7.50 (m, 4H), 7.62 (s, 1H), 7.77 (s, 1H), 8.00 (s, 1H) and 8.27 (s, 1H).
M.S.—m/e—243.2 [M+H]

2. Azidomethylbiphenyl Carboxylates:
   The above biphenyl alcohols (2.0 mmol) in dry dichloromethane (10 mL) were cooled in ice and treated with diphenylphosphoryl azide (2.2 mol) and DBU (2.0 mmol) and stirred under nitrogen for 24 h. The reaction mixture was diluted with water and extracted with ethyl acetate (2×25 mL). The organic layers were combined and washed successfully with 0.5 M citric acid solution (2×25 mL), water (2×25 mL) and dried (Na$_2$SO$_4$). The solution was filtered and evaporated under reduced pressure to yield the crude product. The 4,4'-isomer was crystallized from hexane/ether and the 3,3'-isomer was triturated with isopropyl ether to remove all the impurities; the product was homogeneous as determined on TLC analysis and further purification was not required.

Yield:

Methyl-4-azidomethyl-4-biphenylcaroxylate—0.245 g (46%); m.p.—106–108° C.

Methyl-4-azidomethyl-4-biphenylcaroxylate—0.36 g (59%, oil)

$^1$H NMR (CDCl$_3$) δ-4,4'-isomer—3.95 (s, 3H, —COOCH$_3$), 4.41 (s, 2H, —CH$_2$N$_3$), 7.42 (d, 2H, J=5 Hz), 7.66 (m, 4H) and 8.11 (d, 2H, J=5 Hz)

3,3'-Isomer—3.94 (s, 3H, —COOCH$_3$), 4.41 (s, 2H, —CH$_2$N$_3$), 7.26–7.6 (m, 5H), 7.76 (d, 1H, J=10 Hz), 8.02 (d, 1H, J=5 Hz) and 8.27 (s, 1H).

3. Hydrolysis of the Methyl Esters of Biphenylcarboxylates:

About 4 mmol of the methyl esters were treated with 20 mL of 2M lithium hydroxide solution and stirred until the solution was homogeneous (20–24 h). The aqueous layer was extracted with 2×50 mL of ether and the organic layer was discarded. The aqueous layer was then acidified with 0.5 M citric acid and the precipitated solid was filtered and dried. No other purification was necessary and the acids were taken to the next step.

Yield:

4,4'-isomer—0.87 g of methyl ester yielded 0.754 g of the acid (86.6%); m.p.—205–210° C.

3,3'-isomer—0.48 g of the methyl ester furnished 0.34 g of the acid (63.6%); m.p.—102–105° C.

$^1$H NMR (DMSO-d$_6$) δ: 4,4'-isomer—4.52 (s, 2H, —CH$_2$N$_3$), 7.50 (d, 2H, J=5 Hz), 7.9 (m, 4H), and 8.03 (d, 2H, J=10 Hz)

3,3'-isomer—4.54 (s, 2H, —CH$_2$N$_3$), 7.4 (d, 1H, J=10 Hz), 7.5–7.7 (m, 4H), 7.92 (ABq, 2H) and 8.19 (s, 1H).

4. Reduction of the Azides to the Amine:

This was carried out on the solid phase and the amine was never isolated. The azidocarboxylic acid was loaded on the resin using the standard peptide coupling protocols. After washing, the resin containing the azide was shaken with 20 equivalents of triphenylphosphine in THF/water (95:5) for 24 h. The solution was drained under a positive pressure of nitrogen and then washed with the standard washing procedure. The resulting amine was employed in the next coupling.

5. (3β,5β,7α,12α)-3-[{(9H-Flouren-9ylmethoxy)amino]acetyl}amino-7,12-dihydroxycholan-24-oic qcid:

Tributylamine (3.2 mL); 13.5 mmol was added dropwise to a solution of Fmoc-glycine (4.0 g, 13.5 mmol) in THF (80 mL) stirred at 0° C. Isobutylchloroformate (1.7 mL; 13.5 mmol) was subsequently added and, after 10 min, a suspension of tributylamine (2.6 mL; 11.2 mmol) and (3β,5β,7α,12α)-3-amino-7,12-dihydroxycholan-24-oic acid (4.5 g; 11.2 mmol) in DMF (80 mL) was added dropwise, over 1 h, into the cooled solution. The mixture was allowed to warm up to ambient temperature and after 6 h, the solution was concentrated to 120 mL, then water (180 mL) and 1N HCl (30 mL) were added (final pH 1.5). The precipitated solid was filtered, washed with water (2×100 mL), vacuum dried and purified by flash chromatography. Elution with chloroform/methanol (8:2) yielded the product as a colorless solid.

Yield: 1.9 g (25%). TLC: R$_f$ 0.30 (CHCl$_3$/MeOH/NH$_4$OH—6:3:1).

In vitro and In Vivo Testing of Compounds

Example X

Figure 9A:
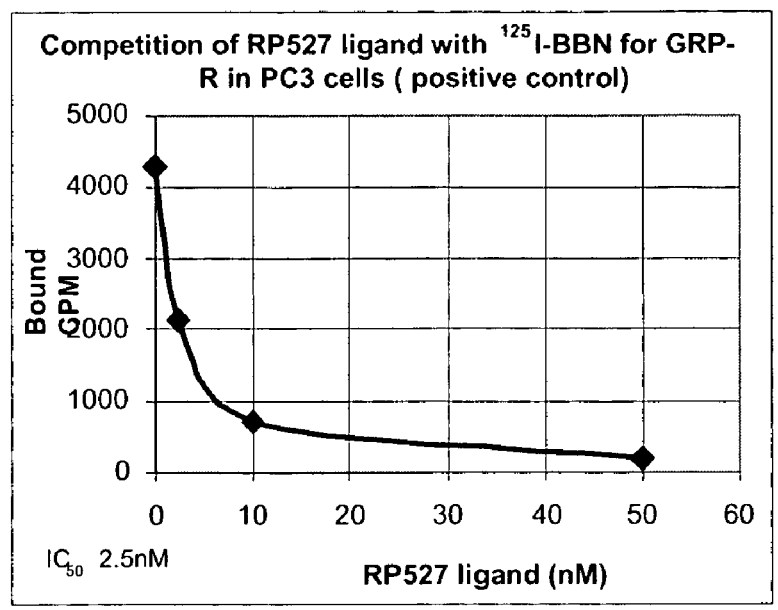
FIG. 9A and FIG. 9B are graphical representations of the binding and competition curves described in Example X.
Figure 9B:
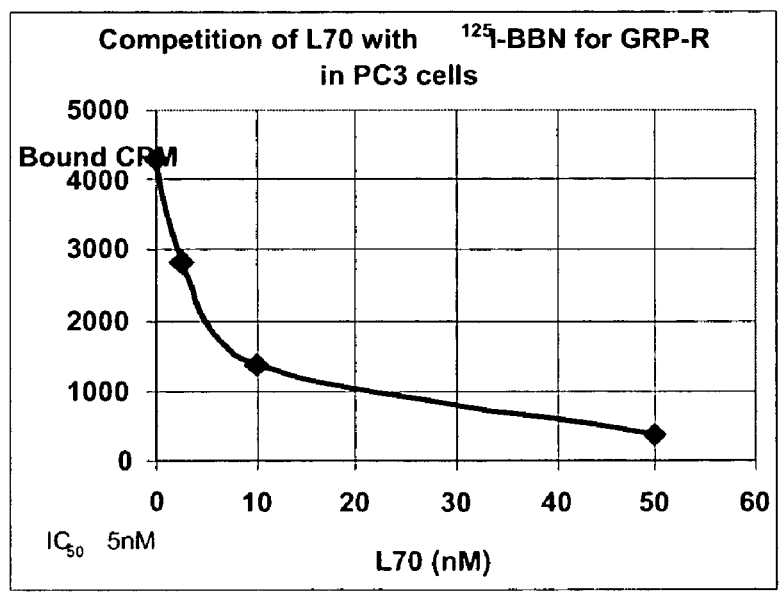

In Vitro Binding Assay for GRP Receptors in PC3 Cell Lines—FIGS. 9A–B

To identify potential lead compounds, an in vitro assay that identifies compounds with high affinity for GRP-R was used. Since the PC3 cell line, derived from human prostate cancer, is known to exhibit high expression of GRP-R on the cell surface, a radio ligand binding assay in a 96-well plate format was developed and validated to measure the binding of $^{125}$I-BBN to GRP-R R positive PC3 cells and the ability of the compounds of the invention to inhibit this binding. This assay was used to measure the IC$_{50}$ for RP527 ligand, L134 ligand (controls) and compounds of the invention which inhibit the binding of $^{125}$I-BBN to GRP-R. (RP527=N,N-dimethylglycine-Ser-Cys(Acm)-Gly-5-aminopentanoic acid-BBN (7-14) [SEQ. ID.NO: 1], which has MS=1442.6 and IC50-0.84). Van de Wiele C, Dumont F et al., Technetium-99m RP527, a GRP analogue for visualization of GRP receptor-expressing malignancies: a feasibility study. Eur. J. Nucl. Med., (2000) 27; 1694–1699.; L134=DO3A-monoamide-8-amino-octanoic acid-BBN (7-14) [SEQ. ID. NO: 1], which has MS=1467.0.

The Radioligand Binding Plate Assay was validated for BBN and BBN analogues (including commercially available BBN and L1) and also using $^{99m}$Tc RP527 as the radioligand.

A. Materials and Method:

1. Cell Culture:

PC3 (human prostate cancer cell line) were obtained from the American Type Culture Collection and cultured in RPMI 1640 in tissue culture flasks (Corning). This growth medium was supplemented with 10% heat inactivated FBS (Hyclone, SH30070.03), 10 mM HEPES (GibcoBRL, 15630-080), and antibiotic/antimycotic (GibcoBRL, 15240-062) for a final concentration of penicillin-streptomycin (100 units/mL), and fungizone (0.25 μg/mL). All cultures were maintained in a humidified atmosphere containing 5% CO$_2$/95% air at 37° C., and passaged routinely using 0.05% trypsin/EDTA (GibcoBRL 25300-054) where indicated. Cells for experiments were plated at a concentration of 2.0×10$^4$/well either in 96-well white/clear bottom microtiter plates (Falcon Optilux-I) or 96 well black/clear collagen I cellware plates (Beckton Dickinson Biocoat). Plates were used for binding studies on day 1 or 2 post-plating.

2. Binding Buffer:

RPMI 1640 supplemented with 20 mM HEPES, 0.1% BSA (w/v), 0.5 mM PMSF (AEBSF), bacitracin (50 mg/500 ml), pH 7.4.

$^{125}$I-BBN (carrier free, 2200 Ci/mmole) was obtained from Perkin-Elmer.

B. Competition Assay with $^{125}$I-BBN for GRP-R in PC3 Cells:

A 96-well plate assay was used to determine the IC$_{50}$ of various compounds of the invention to inhibit binding of $^{125}$I-BBN to human GRP-R. The following general procedure was followed:

All compounds tested were dissolved in binding buffer and appropriate dilutions were also done in binding buffer. PC3 cells (human prostate cancer cell line) for assay were plated at a concentration of 2.0×10$^4$/well either in 96-well white/clear bottomed microtiter plates (Falcon Optilux-I) or 96 well black/clear collagen I cellware plates (Beckton Dickinson Biocoat). Plates were used for binding studies on day 1 or 2 post-plating. The plates were checked for confluency (>90% confluent) prior to assay. For the assay, RP527 or L134 ligand, (controls), or compounds of the invention at concentrations ranging from $1.25 \times 10^{-9}$ M to $5 \times 10^{-9}$ M, was co-incubated with $^{125}$I-BBN (25,000 cpm/well). These studies were conducted with an assay volume of 75 µl per well. Triplicate wells were used for each data point. After the addition of the appropriate solutions, plates were incubated for 1 h at 4° C. to prevent internalization of the ligand-receptor complex. Incubation was ended by the addition of 200 µl of ice-cold incubation buffer.

Plates were washed 5 times and blotted dry. Radioactivity was detected using either the LKB CompuGamma counter or a microplate scintillation counter.

Competition binding curves for RP527 (control) and L70, a compound of the invention can be found in FIGS. 9A–B These data show that the IC50 of the RP527 control is 2.5 nM and that of L70, a compound of this invention is 5 nM. The IC50 of the L134 control was 5 nM. IC50 values for those compounds of the invention tested can be found in tables 1–3 and show that they are comparable to that of the controls and thus would be expected to have sufficient affinity for the receptor to allow uptake by receptor bearing cells in vivo.

C. Internalization & Efflux Assay:

These studies were conducted in a 96-well plate. After washing to remove serum proteins, PC3 cells were incubated with $^{125}$I-BBN, $^{177}$Lu-L134 or radiolabelled compounds of this invention for 40 min, at 37° C. Incubations were stopped by the addition of 200 µl of ice-cold binding buffer. Plates were washed twice with binding buffer. To remove surface-bound radioligand, the cells were incubated with 0.2M acetic acid (in saline), pH 2.8 for 2 min. Plates were centrifuged and the acid wash media were collected to determine the amount of radioactivity which was not internalized. The cells were collected to determine the amount of internalized $^{125}$I-BBN, and all samples were analyzed in the gamma counter. Data for the internalization assay was normalized by comparing counts obtained at the various time points with the counts obtained at the final time point (T40 min). For the efflux studies, after loading the PC3 cells with $^{125}$I-BBN or radiolabelled compounds of the invention for 40 min at 37° c., the unbound material was washed off, and the % of internalization was determined as above. The cells were then resuspended in binding buffer at 37° C. for up to 3 h At 0.5, 1, 2, or 3 h. the amount remaining internalized relative to the initial loading level was determined as above and used to calculate the percent efflux recorded in Table 4.

TABLE 4

Internalisation and efflux of I-BBN and the Lu-177 complexes of L134 (control) and compounds of this invention

|  | I-BBN | L134 | L63 | L64 | L70 |
|---|---|---|---|---|---|
| Internalisation (40 minutes) | 59 | 89 | 64 | 69 | 70 |
| Efflux (2 h) | 35 | 28 | 0 | 20 | 12 |

These data show that the compounds of this invention are internalized and retained by the PC3 cells to a similar extent to the controls.

Example XI

Preparation of Tc-labeled GRP Compounds

Peptide solutions of compounds of the invention identified in Table 5 were prepared at a concentration of 1 mg/mL in 0.1% aqueous TFA. A stannous chloride solution was prepared by dissolving $SnCl_2.2H_2O$ (20 mg/mL) in 1 N HCl. Stannous gluconate solutions containing 20 µg of $SnCl_2.2H_2O$/100 µL were prepared by adding an aliquot of the $SnCl_2$ solution (10 µL) to a sodium gluconate solution prepared by dissolving 13 mg of sodium gluconate in water. A hydroxypropyl gamma cyclodextrin [HP-γ-CD] solution was prepared by dissolving 50 mg of HP-γ-CD in 1 mL of water.

The $^{99m}$Tc labeled compounds identified below were prepared by mixing 20 µL of solution of the unlabeled compounds (20 µg), 50 µL of HP-γ-CD solution, 100 µL of Sn-gluconate solution and 20 to 50 µL of $^{99m}$Tc pertechnetate (5 to 8 mCi, Syncor). The final volume was around 200 µL and final pH was 4.5–5. The reaction mixture was heated at 100° C. for 15 to 20 min. and then analyzed by reversed phase HPLC to determine radiochemical purity (RCP). The desired product peaks were isolated by HPLC, collected into a stabilizing buffer containing 5 mg/mL ascorbic acid, 16 mg/mL HP-γ-CD and 50 mM phosphate buffer, pH 4.5, and concentrated using a speed vacuum to remove acetonitrile. The HPLC system used for analysis and purification was as follows: C18 Vydac column, 4.6×250 mm, aqueous phase: 0.1% TFA in water, organic phase: 0.085% TFA in acetonitrile. Flow rate: 1 mL/min. Isocratic elution at 20%–25% acetonitrile/0.085% TFA was used, depending on the nature of individual peptide.

Labeling results are summarized in Table 5.

TABLE 5

| Compound[1] | Sequence[2] | HPLC retention time (min) | Initial RCP[3] (%) | RCP[4] (%) immediately following purification |
|---|---|---|---|---|
| L2 | -RJQWAVGHLM | 5.47 | 89.9 | 95.6 |
| L4 | -SJQWAVGHLM | 5.92 | 65 | 97 |
| L8 | -JKQWAVGHLM | 6.72 | 86 | 94 |
| L1 | -KJQWAVGHLM | 5.43 | 88.2 | 92.6 |
| L9 | -JRQWAVGHLM | 7.28 | 91.7 | 96.2 |
| L7 | -aJQWAVGHLM | 8.47 | 88.6 | 95.9 | n.d. = not detected

[1]All compounds were conjugated with an N,N'-dimethylglycine-Ser-Cys-Gly metal chelator. The Acm protected form of the ligand was used. Hence, the ligand used to prepare the 99mTc complex of L2 was N,N'-dimethylglycine-Ser-Cys (Acm)-Gly-RJQWAVGHLM. The Acm group was removed during chelation to Tc.
[2]In the Sequence, "J" refers to 8-amino-3,6-dioxaoctanoic acid and "a" refers to D-alanine.
[3]Initial RCP measurement taken immediately after heating and prior to HPL purification.
[4]RCP determined following HPLC isolation and acetonitrile removal via speed vacuum.

Example XII

Preparation of $^{177}$Lu-L64 for Cell Binding and Biodistribution Studies

This compound was synthesized by incubating 10 μg L64 ligand (10 μL of a 1 mg/mL solution in water), 100 μL ammonium acetate buffer (0.2M, pH 5.2) and ~1–2 mCi of $^{177}$LuCl$_3$ in 0.05N HCl (MURR) at 90° C. for 15 min. Free $^{177}$Lu was scavenged by adding 20 μL of a 1% Na$_2$EDTA.2H$_2$O (Aldrich) solution in water. The resulting radiochemical purity (RCP) was ~95%. The radiolabeled product was separated from unlabeled ligand and other impurities by HPLC, using a YMC Basic C8 column [4.6×150 mm], a column temperature of 30° C. and a flow rate of 1 mL/min, with a gradient of 68% A/32% B to 66% A/34% B over 30 min., where A is citrate buffer (0.02M, pH 3.0), and B is 80% CH$_3$CN/20% CH$_3$OH. The isolated compound had an RCP of ~100% and an HPLC retention time of 23.4 minutes.

Samples for biodistribution and cell binding studies were prepared by collecting the desired HPLC peak into 1000 μL of citrate buffer (0.05 M, pH 5.3, containing 1% ascorbic acid, and 0.1% HSA). The organic eluent in the collected eluate was removed by centrifugal concentration for 30 min. For cell binding studies, the purified sample was diluted with cell-binding media to a concentration of 1.5 μCi/mL within 30 minutes of the in vitro study. For biodistribution studies, the sample was diluted with citrate buffer (0.05 M, pH 5.3, containing 1% sodium ascorbic acid and 0.1% HSA) to a final concentration of 50 μCi/mL within 30 minutes of the in vivo study.

Example XIII

Preparation of $^{177}$Lu-L64 for Radiotherapy Studies

This compound was synthesized by incubating 70 μg L64 ligand (70 μL of a 1 mg/mL solution in water), 200 μL ammonium acetate buffer (0.2M, pH 5.2) and ~30–40 mCi of $^{177}$LuCl$_3$ in 0.05N HCl (MURR) at 85° C. for 10 min. After cooling to room temperature, free $^{177}$Lu was scavenged by adding 20 μL of a 2% Na$_2$EDTA.2H$_2$O (Aldrich) solution in water. The resulting radiochemical purity (RCP) was ~95%. The radiolabeled product was separated from unlabeled ligand and other impurities by HPLC, using a 300VHP Anion Exchange column (7.5×50 mm) (Vydac) that was sequentially eluted at a flow rate of 1 mL/min with water, 50% acetonitrile/water and then 1 g/L aqueous ammonium acetate solution. The desired compound was eluted from the column with 50% CH$_3$CN and mixed with 1 mL of citrate buffer (0.05 M, pH 5.3) containing 5% ascorbic acid, 0.2% HSA, and 0.9% (v:v) benzyl alcohol. The organic part of the isolated fraction was removed by spin vacuum for 40 min, and the concentrated solution (~20–25 mCi) was adjusted within 30 minutes of the in vivo study to a concentration of 7.5 mCi/mL using citrate buffer (0.05 M, pH 5.3) containing 5% ascorbic acid, 0.2% HSA, and 0.9% (v:v) benzyl alcohol. The resulting compound had an RCP of >95%.

Example XIV

Preparation of $^{111}$In-L64

This compound was synthesized by incubating 10 μg L64 ligand (5 μL of a 2 mg/mL solution in 0.01 N HCl), 60 μL ethanol, 1.12 mCi of $^{111}$InCl$_3$ in 0.05N HCl (80 μL) and 155 μL sodium acetate buffer (0.5 M, pH 4.5) at 85° C. for 30 min. Free $^{111}$In was scavenged by adding 20 μL of a 1% Na$_2$EDTA.2H$_2$O (Aldrich) solution in water. The resulting radiochemical purity (RCP) was 87%. The radiolabeled product was separated from unlabeled ligand and other impurities by HPLC, using a Vydac C18 column, [4.6×250 mm], a column temperature of 50° C. and a flow rate of 1.5 mL/min. with a gradient of 75% A/25% B to 65% A/35% B over 20 min where A is 0.1% TFA in water, B is 0.085% TFA in acetonitrile. With this system, the retention time for $^{111}$In-L64 is 15.7 min. The isolated compound had an RCP of 96.7%.

Example XV

Preparation of $^{177}$Lu-L134 (Control)

A stock solution of peptide was prepared by dissolving L134 ligand (prepared as described in U.S. Application Publication No. 2002/0054855 and WO 02/87637, both incorporated by reference) in 0.01 N HCl to a concentration of 1 mg/mL. $^{177}$Lu-L134 was prepared by mixing the following reagents in the order shown.

| | |
|---|---|
| 0.2 M NH$_4$OAc, pH 6.8 | 100 μl |
| Peptide stock, 1 mg/mL, in 0.01 N HCl | 5 μl |
| $^{177}$LuCl$_3$ (MURR) in 0.05 M HCl | 1.2 μl (1.4 mCi) |

The reaction mixture was incubated at 85° C. for 10 min. After cooling down to room temperature in a water bath, 20 μl of a 1% EDTA solution and 20 μl of EtOH were added. The compound was analyzed by HPLC using a C18 column (VYDAC Cat # 218TP54) that was eluted at flow rate of 1 mL/min with a gradient of 21 to 25% B over 20 min, where A is 0.1% TFA/H$_2$O and B is 0.1% TFA/CH$_3$CN). $^{177}$Lu-L134 was formed in 97.1% yield (RCP) and had a retention time of ~16.1 min on this system.

Example XVI

Preparation of $^{177}$Lu-L63

This compound was prepared as described for $^{177}$Lu-L134. The compound was analyzed by HPLC using a C18 column (VYDAC Cat # 218TP54) that was eluted at flow rate of 1 mL/min with a gradient of 30–34% B over 20 min (where solvent is A. 0.1% TFA/H$_2$O and B is 0.1% TFA/CH$_3$CN). The $^{177}$Lu-L63 that formed had an RCP of 97.8% and a retention time of ~14.2 min on this system.

Example XVII

Preparation of $^{177}$Lu-L70 for Cell Binding and Biodistribution Studies

This compound was prepared following the procedures described above, but substituting L70 (the ligand of Example II). Purification was performed using a YMC Basic C8 column (4.6×150 mm), a column temperature of 30° C. and a flow rate of 1 mL/min. with a gradient of 80% A/20% B to 75% A/25% B over 40 min., where A is citrate buffer (0.02 M, pH 4.5), and B is 80% CH$_3$CN/20% CH$_3$OH. The isolated compound had an RCP of ~100% and an HPLC retention time of 25.4 min.

Example XVIII

Preparation of $^{177}$Lu-L70 for Radiotherapy Studies

This compound was prepared as described above for L64.

Example XIX

Preparation of $^{111}$In-L70 for Cell Binding and Biodistribution Studies

This compound was synthesized by incubating 10 μg L70 ligand (10 μL of a 1 mg/mL solution in 0.01 N HCl), 180 μL ammonium acetate buffer (0.2M, pH 5.3), 1.1 mCi of $^{111}$InCl$_3$ in 0.05N HCl (61 μL, Mallinckrodt) and 50 μL of saline at 85° C. for 30 min. Free $^{111}$In was scavenged by adding 20 μL of a 1% Na$_2$EDTA.2H$_2$O (Aldrich) solution in water. The resulting radiochemical purity (RCP) was 86%. The radiolabeled product was separated from unlabeled ligand and other impurities by HPLC, using a Waters XTerra C18 cartridge linked to a Vydac strong anion exchange column [7.5×50 mm], a column temperature of 30° C. and a flow rate of 1 mL/min. with the gradient listed in the Table below, where A is 0.1 mM NaOH in water, pH 10.0, B is 1 g/L ammonium acetate in water, pH 6.7 and C is acetonitrile. With this system, the retention time for $^{111}$In-L70 is 15 min while the retention time for L70 ligand is 27 to 28 min. The isolated compound had an RCP of 96%.

Samples for biodistribution and cell binding studies were prepared by collecting the desired HPLC peak into 500 μL of citrate buffer (0.05 M, pH 5.3, containing 5% ascorbic acid, 1 mg/mL L-methionine and 0.2% HSA). The organic part of the collection was removed by spin vacuum for 30 min. For cell binding studies, the purified, concentrated sample was used within 30 minutes of the in vitro study. For biodistribution studies, the sample was diluted with citrate buffer (0.05 M, pH 5.3, containing 5% sodium ascorbic acid and 0.2% HSA) to a final concentration of 10 μCi/mL within 30 minutes of the in vivo study.

| Time, min | A | B | C |
|---|---|---|---|
| 0–10 | 100% | | |
| 10–11 | 100–50% | | 0–50% |
| 11–21 | 50% | | 50% |
| 21–22 | 50–0% | 0–50% | 50% |
| 22–32 | | 50% | 50% |

Example XX

In Vivo Pharmacokinetic Studies

A. Tracer Dose Biodistribution:

Low dose pharmacokinetic studies (e.g., biodistribution studies) were performed using the below-identified compounds of the invention in xenografted, PC3 tumor-bearing nude mice ([Ncr]-Foxn1<nu>). In all studies, mice were administered 100 μL of $^{177}$Lu-labelled test compound at 200 μCi/kg, i.v., with a residence time of 1 and 24 h per group (n=3–4). Tissues were analyzed in an LKB 1282 CompuGamma counter with appropriate standards.

TABLE 6

Pharmacokinetic comparison at 1 and 24 h in PC3 tumor-bearing nude mice (200 μCi/kg; values as % ID/g) of Lu-177 labelled compounds of this invention compared to control

| Tissue | L134 control | | L63 | | L64 | | L70 | |
|---|---|---|---|---|---|---|---|---|
| | 1 hr | 24 hr | 1 hr | 24 hr | 1 hr | 24 hr | 1 hr | 24 hr |
| Blood | 0.44 | 0.03 | 7.54 | 0.05 | 1.87 | 0.02 | 0.33 | 0.03 |
| Liver | 0.38 | 0.04 | 12.15 | 0.20 | 2.89 | 0.21 | 0.77 | 0.10 |
| Kidneys | 7.65 | 1.03 | 7.22 | 0.84 | 10.95 | 1.45 | 6.01 | 2.31 |
| Tumor | 3.66 | 1.52 | 9.49 | 2.27 | 9.83 | 3.60 | 6.42 | 3.50 |
| Pancreas | 28.60 | 1.01 | 54.04 | 1.62 | 77.78 | 6.56 | 42.34 | 40.24 |

Whereas the distribution of radioactivity in the blood, liver and kidneys after injection of L64 and L70 is similar to that of the control compound, L134, the uptake in the tumor is much higher at 1 and 24 h for both L64 and L70. L63 also shows high tumour uptake although with increased blood and liver values at early times. Uptake in the mouse pancreas, a normal organ known to have GRP receptors is much higher for L64, L70 and L63 than for L134.

Example XXI

Radiotherapy Studies

Figure 10A:
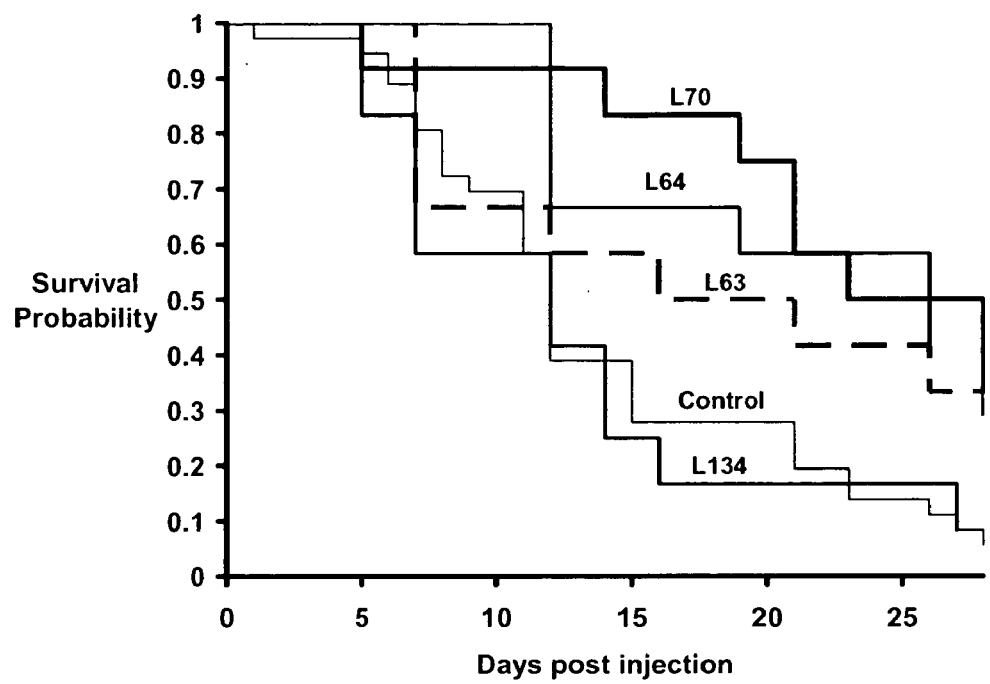
FIG. 10A is a graphical representation of the results of radiotherapy experiments described in Example XXI.

A. Short Term Efficacy Studies:

Radiotherapy studies were performed using the PC3 tumor-bearing nude mouse model. Lu-177 labelled compounds of the invention L64, L70, L63 and the treatment control compound L134 were compared to an untreated control group. (n=12 for each treatment group and n=36 for the untreated control group). For the first study, mice were administered 100 μL of $^{177}$Lu-labelled compound of the invention at 30 mCi/kg, i.v, or s.c. under sterile conditions. The subjects were housed in a barrier environment for up to 30 days. Body weight and tumor size (by caliper measurement) were collected on each subject 3 times per week for the duration of the study. Criteria for early termination included: death; loss of total body weight (TBW) equal to or greater than 20%; tumor size equal to or greater than 2 cm$^3$. Results are displayed in FIG. 10A. These results show that animals treated with L70, L64 or L63 have increased survival over the control animals given no treatment and over those animals given the same dose of L134.

Figure 10B:
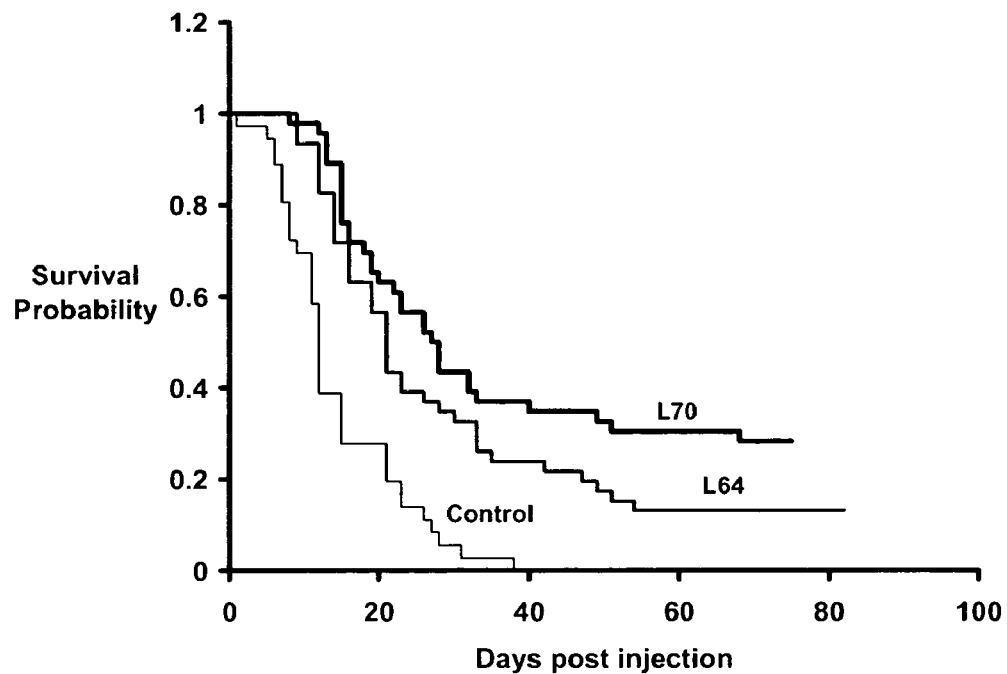
FIG. 10B is a graphical representation of the results of other radiotherapy experiments described in Example XXI.
Figure 11:
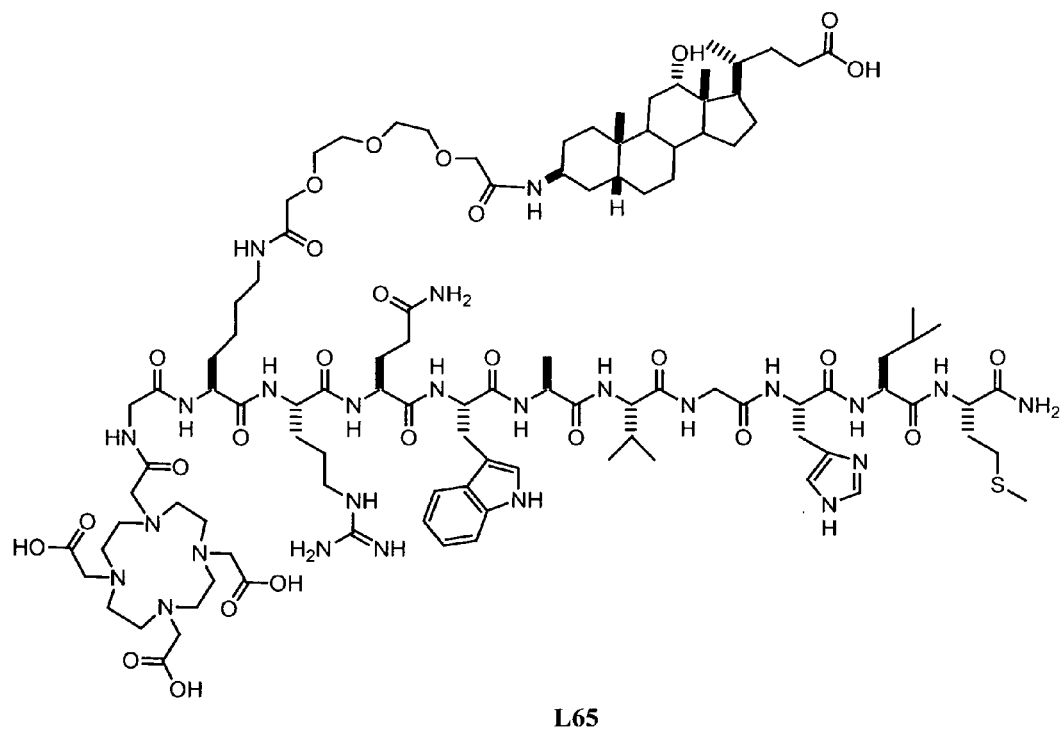
FIG. 11 is a chemical structure of DO3A-monoamide-Gly-Lys-(3,6,9)-trioxaundecane-1,11-dicarboxylic acid-3,7-dideoxy-3-aminocholic acid)-L-arginyl-L-glutaminyl-L-triptophyl-L-alanyl-L-valyl -glycyl-L-histidyl-L-leucyl-L-methioninamide (L65)
Figure 12:
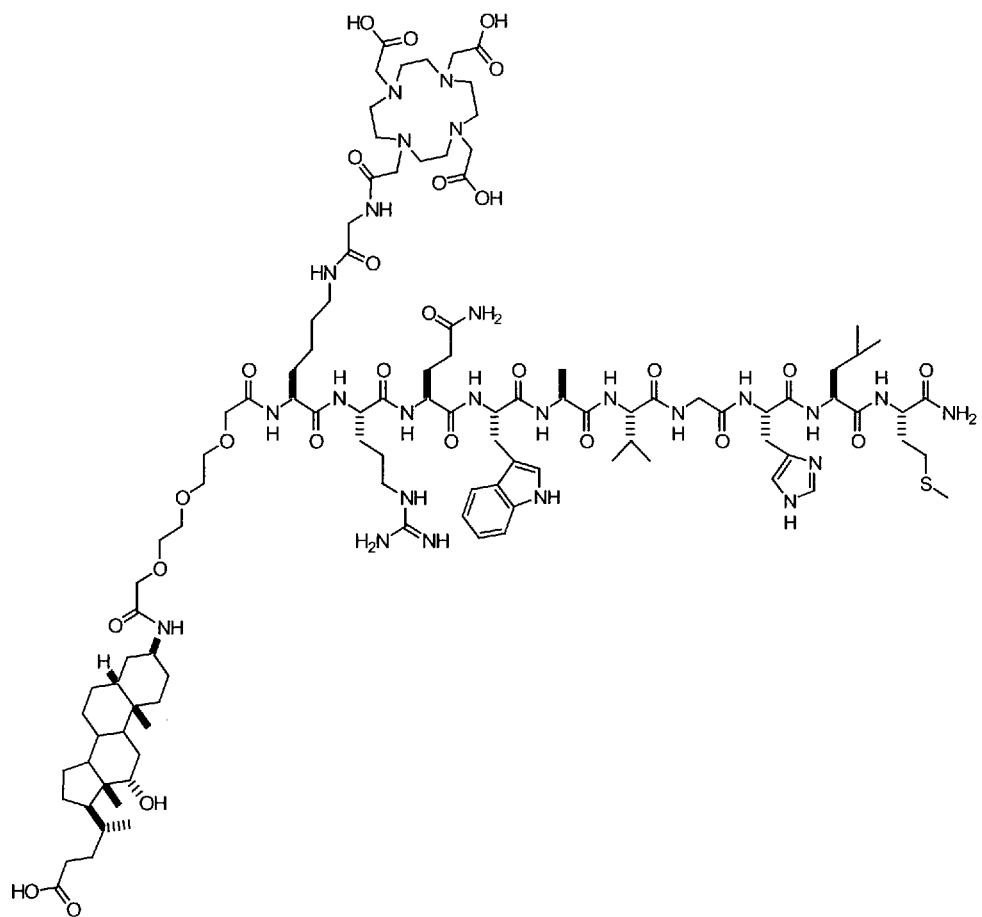
FIG. 12 is a chemical structure of N-[2-S-[[[[[12α-Hydroxy-17β-(1-methyl-3-carboxypropyl)etiocholan-3β-carbamoylmethoxyethoxyethoxyacetyl]-amino-6-[4,7,10-tris (carboxymethyl)-1,4,7,10-tetraazacyclododec-1-yl]acetyl] amino]acetyl]amino]hexanoyl-L-glutaminyl -L-tryptophyl-L-alanyl-L-valyl-glycyl-L-histidyl-L-leucyl-L-methioninamide (L66)
Figure 13A:
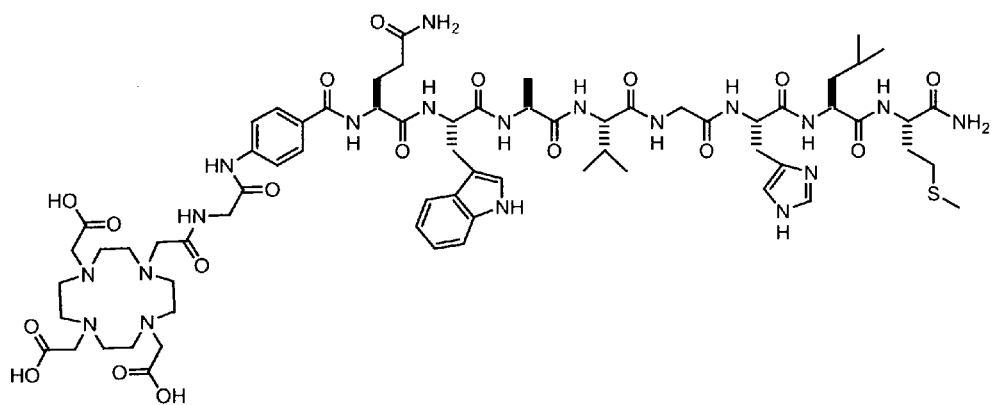
FIG. 13A is a chemical structure of N-[4-[[[[[4,7,10-Tris (carboxymethyl)-1,4,7,10-tetraazacyclododec-1-yl]acetyl] amino]acetyl]amino]benzoyl]-L-glutaminyl-L-tryptophyl-L-alanyl-L-valyl-glycyl-L-histidyl-L-leucyl-L-methioninamide (L70)
Figure 13B:
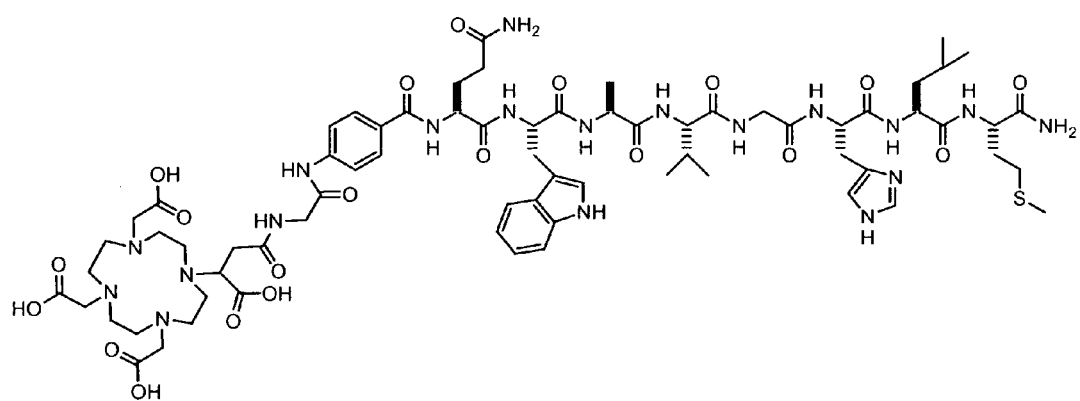
FIG. 13B is a chemical structure N-[4-[[[[[4,7,10-Tris (carboxymethyl)-1,4,7,10-tetraazacyclododec-1-yl]-3-carboxypropionyl]amino]acetyl]amino]benzoyl]-L-glutaminyl-L-tryptophyl-L-alanyl-L-valyl-glycyl-L-histidyl-L-leucyl-L-methioninamide (L114)
Figure 13C:
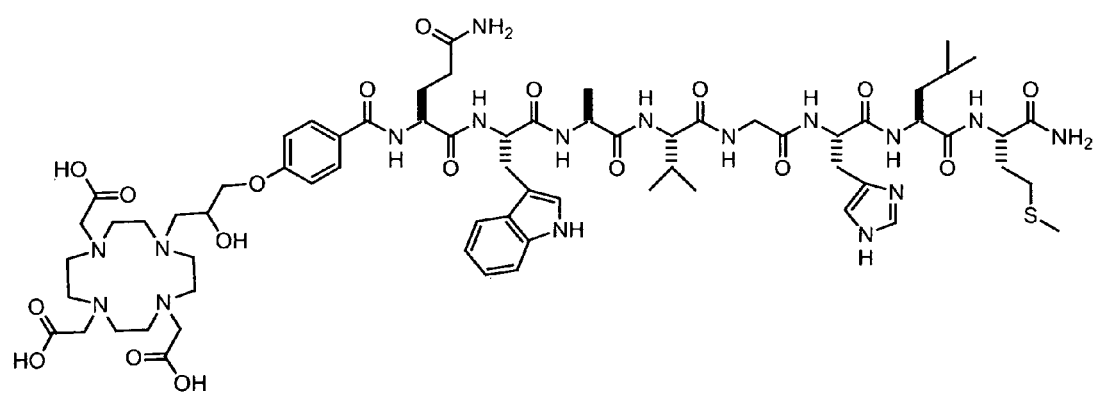
FIG. 13C is a chemical structure N-[4-[[4,7,10-Tris(carboxymethyl)-1,4,7,10-tetraazacyclododec-1-yl]-2-hydroxy-3-propoxy]benzoyl]-L-glutaminyl-L-tryptophyl-L-alanyl-L-valyl-glycyl-L-histidyl-L-leucyl-L-methioninamide (L144)
Figure 13D:
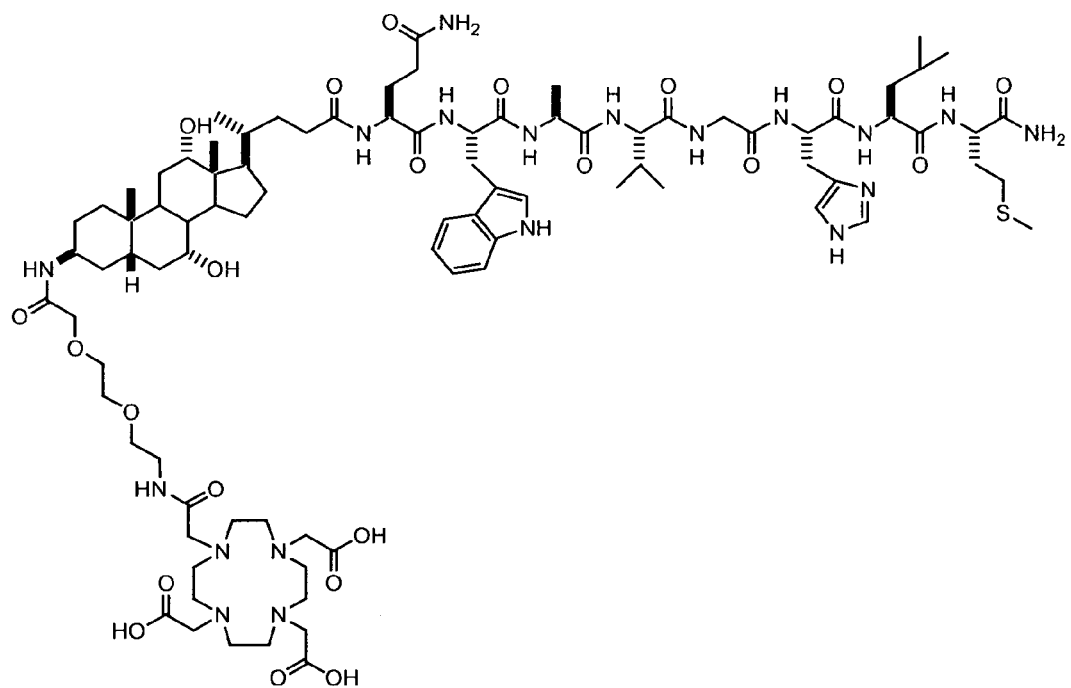
FIG. 13D is a chemical structure N-[(3β,5β,7α,12α)-3-[[[[[4,7,10-Tris(carboxymethyl)-1,4,7,10-tetraazacyclododec-1-yl]acetyl]amino]ethoxyethoxy]acetyl]amino]-7,12-dihydroxycholan-24-yl]-L-glutaminy-L-tryptophyl-L-alanyl-L-valyl-glycyl-L-histidyl-L-leucyl-L-methioninamide (L69)
Figure 13E:
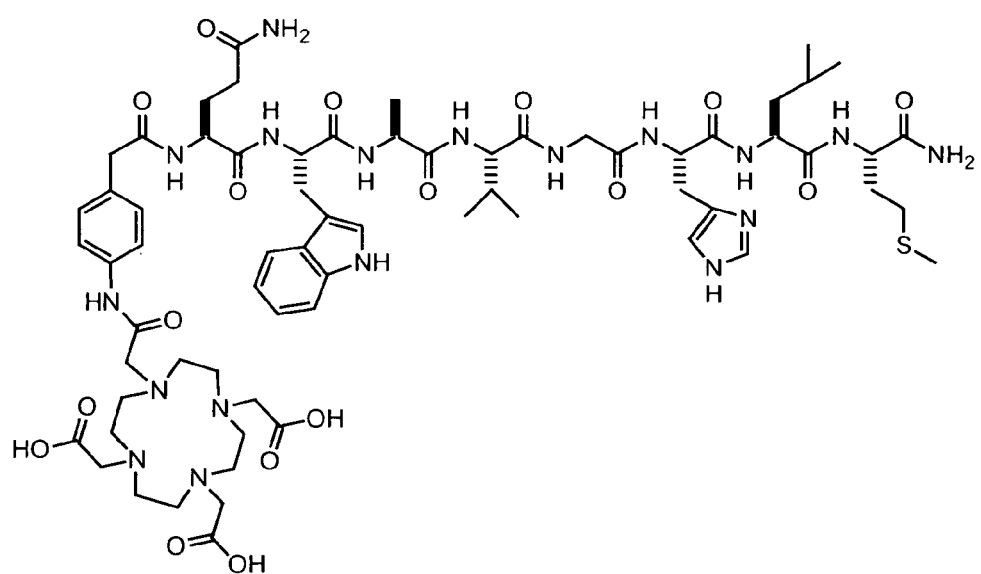
FIG. 13E is a chemical structure N-[4-[[[[[4,7,10-Tris (carboxymethyl)-1,4,7,10-tetraazacyclododec-1-yl]acetyl] amino]acetyl]amino]phenylacetyl]-L-glutaminyl-L-tryptophyl-L-alanyl-L-valyl-glycyl-L-histidyl-L-leucyl-L-methioninamide (L146).

A repeat study was performed with L64 and L70 using the same dose as before but using more animals per compound (n=46) and following them for longer. The results of the repeat study are displayed in FIG. 10B. Relative to the same controls as before (n=36), both L64 and L70 treatment give significantly increased survival (p<0.0001) with L70 being better than L64 (p0.079).

Example XXII

Alternative Preparation of L64 and L70 Using Segment Coupling

Figure 14:
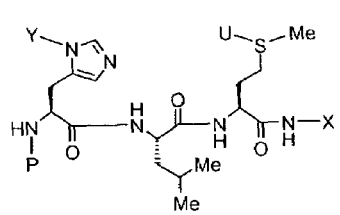
FIG. 14 dicloses chemical structures of intermediates which may be used to prepare compounds L64 and L70 as described in Example XXII.
Figure 14:
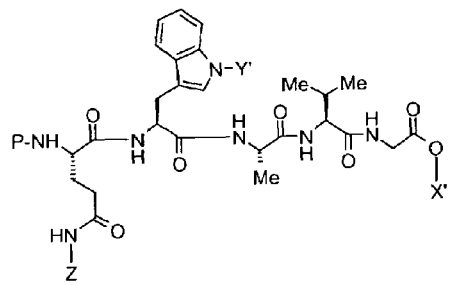
Figure 14:
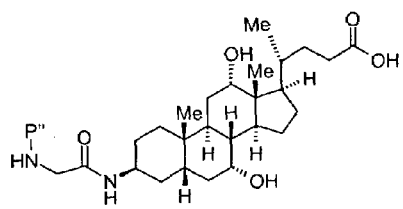
Figure 14:
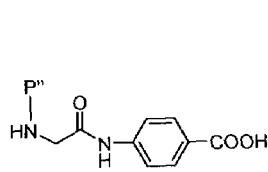
Figure 14:
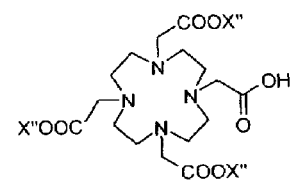

Compounds L64 and L70 can be prepared employing the collection of intermediates generally represented by A–D (FIG. 14), which themselves are prepared by standard methods known in the art of solid and solution phase peptide synthesis (Synthetic Peptides—A User's Guide 1992, Grant, G., Ed. WH. Freeman Co., NY, Chap 3 and Chap 4 pp 77–258; Chan, W. C. and White, P. D. Basic Procedures in Fmoc Solid Phase Peptide Synthesis—A Practical Approach 2002, Chan, W. C. and White, P. D. Eds Oxford University Press, New York, Chap. 3 pp 41–76; Barlos, K and Gatos, G. Convergent Peptide Synthesis in Fmoc Solid Phase Peptide Synthesis—A Practical Approach 2002, Chan, W. C. and White, P. D. Eds Oxford University Press, New York, Chap. 9 pp 216–228.) which are incorporated herein by reference.

These methods include Aloc, Boc, Fmoc or benzyloxycarbonyl-based peptide synthesis strategies or judiciously chosen combinations of those methods on solid phase or in solution. The intermediates to be employed for a given step are chosen based on the selection of appropriate protecting groups for each position in the molecule, which may be selected from the list of groups shown in FIG. 1. Those of ordinary skill in the art will also understand that intermediates, compatible with peptide synthesis methodology, comprised of alternative protecting groups can also be employed and that the listed options for protecting groups shown above serves as illustrative and not inclusive, and that such alternatives are well known in the art.

Figure 15:
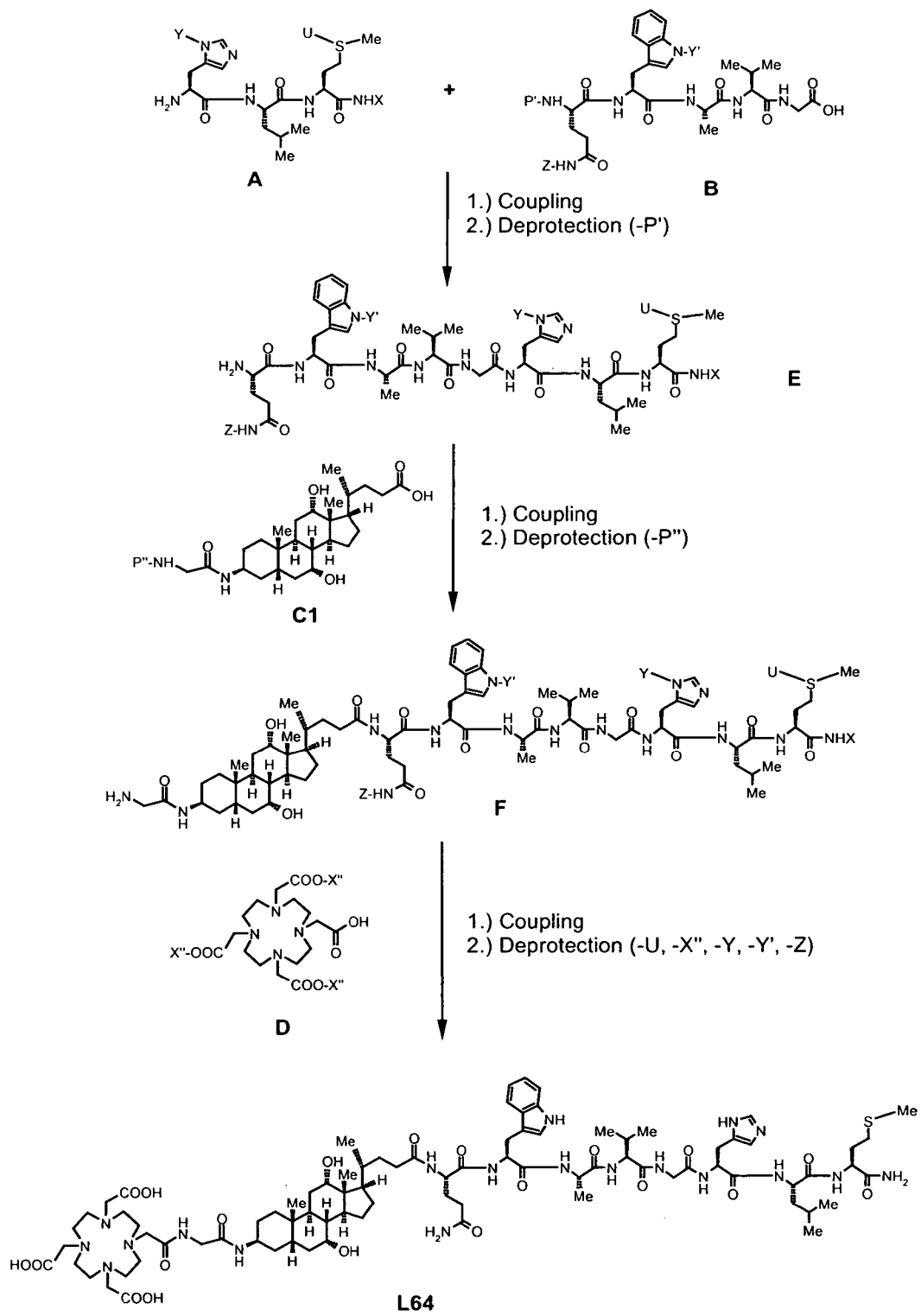
FIG. 15 is a graphical representation of the preparation of L64 using segment coupling as described in Example XXII.

This is amply illustrated in FIG. 15 which outlines the approach. Substitution of the intermediate C2 in place of C1 shown in the synthesis of L64, provides L70 when the same synthetic strategies are applied.

compound comprising DO3A-monoamide-Gly-4-aminobenzoic acid-BBN(7-14) wherein the BBN(7-14) sequence is SEQ. ID NO: 1.

5. A method of treating a patient in need of radiotherapy comprising the step of administering to a patient a radiotherapeutic agent comprising the compound of claim 1 complexed with a therapeutic radionuclide.

6. A method of preparing a radiotherapeutic agent comprising the step of adding to an injectable medium a substance comprising the compound of claim 1.

7. A compound of the general formula:

M-N-O-P-G wherein
M is a metal chelator;
N is 0, an alpha amino acid, a non-alpha amino acid with a cyclic group or other linking group;
O is an alpha amino acid or a non-alpha amino acid with a cyclic group;
P is 0, an alpha amino acid, a non-alpha amino acid with a cyclic group, or other linking group; and
G is a GRP receptor targeting peptide,
wherein at least one of N, O or P is a non-alpha amino acid with a cyclic group.

8. The compound of claim 7, wherein G is an agonist.

9. The compound of claim 7, wherein the non-alpha amino acid with a cyclic group is selected from the group consisting of:

---

---

We claim:

1. A method for preparing a diagnostic imaging agent comprising the step of adding to an injectable medium a compound comprising DO3A-monoamide-Gly-4-aminobenzoic acid-BBN(7-14) wherein the BBN(7-14) sequence is SEQ. ID NO: 1.

2. A compound DO3A-monoamide-Gly-4-aminobenzoic acid-BBN(7-14) wherein the BBN(7-14) sequence is SEQ. ID NO: 1.

3. A method of imaging comprising the steps of:
administering to a patient a diagnostic imaging agent comprising DO3A-monoamide-Gly-4-aminobenzoic acid-BBN(7-14) complexed with a diagnostic radionuclide, wherein the BBN(7-14) sequence is SEQ. ID NO: 1, and
imaging said patient.

4. A method for preparing a diagnostic imaging agent comprising the step of adding to an injectable medium a 4-aminobenzoic acid;
4-aminomethyl benzoic acid;
trans-4-aminomethylcyclohexane carboxylic acid;
4-(2-aminoethoxy)benzoic acid;
isonipecotic acid;
2-aminomethylbenzoic acid;
4-aminomethyl-3-nitrobenzoic acid;
4-(3-carboxymethyl-2-keto-1-benzimidazolyl)-piperidine;
6-(piperazin-1-yl)-4-(3H)-quinazolinone-3-piperazineacetic acid;
(2S,5 S)-5-amino-1,2,4,5,6,7-hexahydro-azepino[3,21-hi]indole-4-one-2-carboxylic acid;
(4S,7R)-4-amino-6-aza-5-oxo-9-thiabicyclo[4.3.0]nonane-7-carboxylic acid;
3-carboxymethyl-1-phenyl-1,3,8-triazaspiro[4.5]decan-4-one;
N1-piperazineacetic acid;
N-4-aminoethyl-N-1-acetic acid;

(3S)-3-amino-1-carboxymethylcaprolactam; and
(2S,6S,9)-6-amino-2-carboxymethyl-3,8-diazabicyclo-[4,3,0]-nonane-1,4-dione.

10. The compound of claim 7, wherein M is selected from the group consisting of: DTPA, DOTA, DO3A, HPDO3A, EDTA, and TETA.

11. The compound of claim 7, wherein M is selected from the group consisting of EHPG and derivatives thereof.

12. The compound of claim 11, wherein M is selected from the group consisting of 5-Cl-EHPG, 5-Br-EHPG, 5-Me-EHPG, 5-t-Bu-EHPG, and 5-sec-Bu-EHPG.

13. The compound of claim 7, wherein M is selected from the group consisting of benzodiethylenetriamine pentaacetic acid (benzo-DTPA) and derivatives thereof.

14. The compound of claim 13, wherein M is selected from the group consisting of dibenzo-DTPA, phenyl-DTPA, diphenyl-DTPA, benzyl-DTPA, and dibenzyl DTPA.

15. The compound of claim 7, wherein M is selected from the group consisting of HBED and derivatives thereof.

16. The compound of claim 7, wherein M is selected from the group consisting of benzo-DOTA, dibenzo-DOTA, and benzo-NOTA, benzo-TETA, benzo-DOTMA, and benzo-TETMA.

17. The compound of claim 7, wherein M is selected from the group consisting of derivatives of 1,3-propylenediamine-tetraacetic acid (PDTA) and triethylenetetraaminehexaacetic acid (TTHA); derivatives of 1,5,10-N,N',N''-tris(2,3-dihydroxybenzoyl)-tricatecholate (LICAM) and 1,3,5-N,N',N''-tris(2,3-dihydroxybenzoyl)aminomethylbenzene (MECAM).

18. The compound of claim 7, selected from the group consisting of

DO3A-monoamide-Gly-4-aminobenzoic acid-BBN(7-14) wherein the BBN(7-14) sequence is SEQ. ID NO: 1;

DO3A-monoamide-4-aminomethyl benzoic acid-BBN(7-14) wherein the BBN(7-14) sequence is SEQ. ID NO: 1;

DO3A-monoamide-trans-4-aminomethylcyclohexyl carboxylic acid-BBN(7-14) wherein the BBN(7-14) sequence is SEQ. ID NO: 1;

DO3A-monoamide-4-(2-aminoethoxy)benzoic acid-BBN(7-14) wherein the BBN(7-14) sequence is SEQ. ID NO: 1;

DO3A-monoamide-Gly-isonipecotic acid-BBN(7-14) wherein the BBN(7-14) sequence is SEQ. ID NO: 1;

DO3A-monoamide-2-aminomethylbenzoic acid-BBN(7-14) wherein the BBN(7-14) sequence is SEQ. ID NO: 1;

DO3A-monoamide-4-aminomethyl-3-nitrobenzoic acid-BBN(7-14) wherein the BBN(7-14) sequence is SEQ. ID NO: 1;

DO3A-monoamide-8-amino-3,6-dioxaoctanoic acid-1-naphthylalanine-BBN(7-14) wherein the BBN(7-14) sequence is SEQ. ID NO: 1;

DO3A-monoamide-4-(3-carboxymethyl-2-keto-1-benzimidazolyl-piperidine-BBN(7-14) wherein the BBN(7-14) sequence is SEQ. ID NO: 1;

DO3A-monoamide-6-(piperazin-1-yl)-4-(3H)-quinazolinone-3-acetic acid-BBN(7-14) wherein the BBN(7-14) sequence is SEQ. ID NO: 1;

DO3A-monoamide-(2S,5S)-5-amino-1,2,4,5,6,7-hexahydro-azepino[3,21-hi]indole-4-one-2-carboxylic acid-BBN(7-14) wherein the BBN(7-14) sequence is SEQ. ID NO: 1;

DO3A-monoamide-(4S,7R)-4-amino-6-aza-5-oxo-9-thiabicyclo[4.3.0]nonane-7-carboxylic acid-BBN(7-14) wherein the BBN(7-14) sequence is SEQ. ID NO: 1;

DO3A-monoamide-3-carboxymethyl-1-phenyl-1,3,8-triazaspiro[4.5]decan-4-one-BBN(7-14) wherein the BBN(7-14) sequence is SEQ. ID NO: 1;

DO3A-monoamide-N1-piperazineacetic acid-BBN(7-14) wherein the BBN(7-14) sequence is SEQ. ID NO: 1;

DO3A-monoamide-N-4-aminoethyl-N-1-piperazineacetic acid-BBN(7-14) wherein the BBN(7-14) sequence is SEQ. ID NO: 1;

DO3A-monoamide-(3S)-3-amino-1-carboxymethylcaprolactam-BBN(7-14) wherein the BBN(7-14) sequence is SEQ. ID NO: 1;

DO3A-monoamide-(2S,6S,9)-6-amino-2-carboxymethyl-3,8-diazabicyclo-[4,3,0]-nonane-1,4-dione-BBN(7-14) wherein the BBN(7-14) sequence is SEQ. ID NO: 1;

DO3A-monoamide-5-aminopentanoic acid-trans-4-aminomethylcyclohexane-1-carboxylic acid-BBN(7-14) wherein the BBN(7-14) sequence is SEQ. ID NO: 1;

DO3A-monoamide-trans-4-aminomethylcyclohexane-1-carboxylic acid-D-phenylalanine-BBN(7-14) wherein the BBN(7-14) sequence is SEQ. ID NO: 1;

DO3A-monoamide-4-aminomethylbenzoic acid-8-amino-3,6-dioxaoctanoic acid-BBN(7-14) wherein the BBN(7-14) sequence is SEQ. ID NO: 1;

DO3A-monoamide-4-benzoyl-(L)-phenylalanine-trans-4-aminomethylcyclohexane-1-carboxylic acid-BBN(7-14) wherein the BBN(7-14) sequence is SEQ. ID NO: 1;

DO3A-monoamide-trans-4-aminomethylcyclohexane-1-carboxylic acid-Arg-BBN(7-14) wherein the BBN(7-14) sequence is SEQ. ID NO: 1;

DO3A-monoamide-trans-4-aminomethylcyclohexane-1-carboxylic acid-Lys-BBN(7-14) wherein the BBN(7-14) sequence is SEQ. ID NO: 1;

DO3A-monoamide-trans-4-aminomethylcyclohexane-1-carboxylic acid-diphenylalanine-BBN(7-14) wherein the BBN(7-14) sequence is SEQ. ID NO: 1;

DO3A-monoamide-trans-4-aminomethylcyclohexane-1-carboxylic acid-1-naphthylalanine-BBN(7-14) wherein the BBN(7-14) sequence is SEQ. ID NO: 1;

DO3A-monoamide-trans-4-aminomethylcyclohexane-1-carboxylic acid-8-amino-3,6-dioxaoctanoic acid-BBN(7-14) wherein the BBN(7-14) sequence is SEQ. ID NO: 1;

DO3A-monoamide-trans-4-aminomethylcyclohexane-1-carboxylic acid-Ser-BBN(7-14) wherein the BBN(7-14) sequence is SEQ. ID NO: 1;

DO3A-monoamide-trans-4-aminomethylcyclohexane-1-carboxylic acid-2,3-diaminopropionic acid-BBN(7-14) wherein the BBN(7-14) sequence is SEQ. ID NO: 1;

DO3A-monoamide-trans-4-aminomethylcyclohexane-1-carboxylic acid-biphenylalanine-BBN(7-14) wherein the BBN(7-14) sequence is SEQ. ID NO: 1;

DO3A-monoamide-trans-4-aminomethylcyclohexane-1-carboxylic acid-(2S,5 S)-5-amino-1,2,4,5,6,7-hexahydro-azepino[3,21-hi]indole-4-one-2-carboxylic acid-BBN(7-14) wherein the BBN(7-14) sequence is SEQ. ID NO: 1;

DO3A-monoamide-trans-4-aminomethylcyclohexane-1-carboxylic acid-trans-4-aminomethylcyclohexane-1-carboxylic acid-BBN(7-14) wherein the BBN(7-14) sequence is SEQ. ID NO: 1;

DO3A-monoamide-8-amino-3,6-dioxaoctanoic acid-phenylalanine-BBN(7-14) wherein the BBN(7-14) sequence is SEQ. ID NO: 1;

DO3A-monoamide-trans-4-aminomethylcyclohexane-1-carboxylic acid-phenylalanine-BBN(7-14) wherein the BBN(7-14) sequence is SEQ. ID NO: 1;

DO3A-monoamide-8-aminooctanoic acid-trans-4-aminomethylcyclohexane-1-carboxylic acid-BBN(7-14) wherein the BBN(7-14) sequence is SEQ. ID NO: 1;

DO3A-monoamide-4'-aminomethyl-biphenyl-1-carboxylic acid-BBN(7-14) wherein the BBN(7-14) sequence is SEQ. ID NO: 1;

DO3A-monoamide-3'-aminomethyl-biphenyl-3-carboxylic acid-BBN(7-14) wherein the BBN(7-14) sequence is SEQ. ID NO: 1;

CMDOTA-Gly-4-aminobenzoic acid-BBN(7-14) wherein the BBN(7-14) sequence is SEQ. ID NO: 1;

DO3A-monoamide-4-aminomethylphenoxyacetic acid-BBN(7-14) wherein the BBN(7-14) sequence is SEQ. ID NO: 1;

DO3A-monoamide-Gly-4-aminophenylacetic acid-BBN(7-14) wherein the BBN(7-14) sequence is SEQ. ID NO: 1;

HPDO3A-4-phenoxy-BBN(7-14) wherein the BBN(7-14) sequence is SEQ. ID NO: 1;

DO3A-monoamide-3-aminomethylbenzoic acid-BBN(7-14) wherein the BBN(7-14) sequence is SEQ. ID NO: 1;

DO3A-monoamide-4-aminomethylphenylacetic acid-BBN(7-14) wherein the BBN(7-14) sequence is SEQ. ID NO: 1; and DO3A-monoamide-4-aminomethyl-3-methoxybenzoic acid-BBN(7-14) wherein the BBN(7-14) sequence is SEQ. ID NO: 1.

19. A method of imaging comprising the steps of:

administering to a patient a diagnostic imaging agent comprising the compound of claim 7 complexed with a diagnostic radionuclide, and imaging said patient.

20. A method for preparing a diagnostic imaging agent comprising the step of adding to an injectable medium a substance comprising the compound of claim 7.

21. A method of treating a patient in need of radiotherapy comprising the step of administering to a patient a radiotherapeutic agent comprising the compound of claim 7 complexed with a therapeutic radionuclide.

22. A method of preparing a radiotherapeutic agent comprising the step of adding to an injectable medium a substance comprising the compound of claim 7.

23. A method of synthesizing DO3A-monoamide-Gly-4-aminobenzoic acid-BBN(7-14) wherein the BBN(7-14) sequence is SEQ. ID NO: 1 comprising the steps of:

(a) shaking a solution in a solid phase peptide synthesis vessel or reaction block, said solution comprising a resin and at least one peptide building ingredient, (b) flushing said solution, and (c) washing said resin with DMA, wherein said at least one peptide building ingredient includes DMA, morpholine, Fmoc-4-aminobenzoic acid, HOBt, DIC, HBTU, HATU or mixtures thereof, and wherein each of steps (a), (b) and (c) are repeated until the compound DO3A-monoamide-Gly-4-aminobenzoic acid-BBN(7-14) wherein the BBN(7-14) sequence is SEQ. ID NO: 1 is obtained.

24. A method for labeling DO3A-monoamide-Gly-4-aminobenzoic acid-BBN(7-14) wherein the BBN(7-14) sequence is SEQ. ID NO: 1 comprising the steps of incubating a first solution comprising DO3A-monoamide-Gly-4-aminobenzoic acid-BBN(7-14) wherein the BBN(7-14) sequence is SEQ. ID NO: 1, ammonium acetate, a radioactive metal precursor selected from the group consisting of $^{177}$LuCl$_3$ or $^{111}$InCl$_3$, HCl, and adding to said first solution a second solution comprising Na$_2$EDTA.2H$_2$O and water to obtain a radiochemical purity greater than 95%.

* * * * *